(12) United States Patent
Polyak et al.

(10) Patent No.: US 11,666,580 B2
(45) Date of Patent: Jun. 6, 2023

(54) MECHANISM OF RESISTANCE TO BET BROMODOMAIN INHIBITORS

(71) Applicant: Dana-Farber Cancer Institute, Inc., Boston, MA (US)

(72) Inventors: Kornelia Polyak, Brookline, MA (US); Shaokun Shu, Brookline, MA (US); James E. Bradner, Weston, MA (US); Charles Yang Lin, Houston, TX (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 543 days.

(21) Appl. No.: 15/751,914

(22) PCT Filed: Aug. 10, 2016

(86) PCT No.: PCT/US2016/046318
§ 371 (c)(1),
(2) Date: Feb. 12, 2018

(87) PCT Pub. No.: WO2017/027571
PCT Pub. Date: Feb. 16, 2017

(65) Prior Publication Data
US 2020/0368248 A1 Nov. 26, 2020

Related U.S. Application Data

(60) Provisional application No. 62/203,128, filed on Aug. 10, 2015.

(51) Int. Cl.
*A61K 31/551* (2006.01)
*A61K 31/5415* (2006.01)
(Continued)

(52) U.S. Cl.
CPC .......... *A61K 31/551* (2013.01); *A61K 31/137* (2013.01); *A61K 31/5415* (2013.01);
(Continued)

(58) Field of Classification Search
CPC ................ A61K 31/551; A61K 31/137; A61K 31/5415; A61K 45/06; A61K 31/635;
(Continued)

(56) References Cited

U.S. PATENT DOCUMENTS 6,607,916 B2   8/2003   Freier et al.
8,309,582 B2   11/2012  Chen et al.
(Continued)

FOREIGN PATENT DOCUMENTS

JP   2008-156311 A   7/2008
JP   2009-028043 A   2/2009
(Continued)

OTHER PUBLICATIONS

Kumar et al., GLI2-dependent c-MYC upregulation mediates resistance of pancreatic cancer cells to the BET bromodomain inhibitor JQ1. Sci. Rep. 5, 9489; DOI:10.1038/srep09489 (2015) (Year: 2015).*

(Continued)

*Primary Examiner* — Kortney L. Klinkel
*Assistant Examiner* — Padmaja S Rao
(74) *Attorney, Agent, or Firm* — Wolf, Greenfield & Sacks, P.C.

(57) ABSTRACT

The present disclosure provides combination therapy comprising a BET inhibitor and a protein phosphatase 2A (PP2A) activator, a B-cell lymphoma-2 (Bcl-2) inhibitor, a B-cell lymphoma-extra large (Bcl-xl) inhibitor, a casein kinase 2 (CK2) inhibitor, and/or a mediator complex subunit 1 (MED1) for cancer. The combination therapy is expected to be synergistic in treating the cancer, compared to the monotherapy. Methods for identifying a subject having a cancer that is resistant to or at risk of developing resistance (Continued)

to bromodomain and extra terminal (BET) inhibitor therapy are also provided.

20 Claims, 35 Drawing Sheets

Specification includes a Sequence Listing.

(51) Int. Cl.
    *A61K 45/06* (2006.01)
    *G01N 33/574* (2006.01)
    *A61P 35/00* (2006.01)
    *A61K 31/137* (2006.01)
(52) U.S. Cl.
    CPC .............. *A61K 45/06* (2013.01); *A61P 35/00* (2018.01); *G01N 33/57415* (2013.01)
(58) Field of Classification Search
    CPC .............. A61K 31/4745; A61K 31/496; A61K 39/395; A61K 2300/00; G01N 33/57415; G01N 2800/52; G01N 33/6872; A61P 43/00; A61P 35/00; C07D 215/42; C07D 471/04; C07D 255/04; C07D 495/14
    See application file for complete search history.

(56) References Cited

U.S. PATENT DOCUMENTS

| | | | |
|---|---|---|---|
| 8,557,812 B2 | 10/2013 | Wang et al. | |
| 8,865,901 B2 | 10/2014 | Hockenbery et al. | |
| 2010/0256217 A1 | 10/2010 | Weiner et al. | |
| 2010/0267673 A1 | 10/2010 | Chen et al. | |
| 2011/0143651 A1 | 6/2011 | Marocchi et al. | |
| 2011/0207789 A1 | 8/2011 | Fang et al. | |
| 2014/0005169 A1 | 1/2014 | Albrecht et al. | |
| 2014/0028912 A1 | 1/2014 | Lenzi et al. | |
| 2014/0016297 A1 | 6/2014 | Wang et al. | |
| 2014/0162971 A1 | 6/2014 | Wang et al. | |
| 2014/0296218 A1 | 10/2014 | Young et al. | |
| 2016/0368919 A1* | 12/2016 | Casimiro-Garcia | .... A61P 37/06 |

FOREIGN PATENT DOCUMENTS

| | | |
|---|---|---|
| JP | 2009-183291 A | 8/2009 |
| WO | WO 2006/065724 A2 | 6/2006 |
| WO | WO 2007/143081 A2 | 12/2007 |
| WO | WO 2008/119109 A1 | 10/2008 |
| WO | WO 2008/127710 A2 | 10/2008 |
| WO | WO 2009/084693 A1 | 7/2009 |
| WO | WO-2009117769 A1 * 10/2009 ............... A61P 35/00 |
| WO | WO 2011/054843 A1 | 5/2011 |
| WO | WO 2011/054844 A1 | 5/2011 |
| WO | WO 2011/054846 A1 | 5/2011 |
| WO | WO 2011/054848 A1 | 5/2011 |
| WO | WO 2011/054851 A1 | 5/2011 |
| WO | WO 2011/143660 A2 | 11/2011 |
| WO | WO 2011/143669 A2 | 11/2011 |
| WO | WO 2012/071374 A1 | 5/2012 |
| WO | WO 2012/103059 A2 | 8/2012 |
| WO | WO 2013/181488 A2 | 12/2013 |
| WO | WO 2014/039994 A2 | 3/2014 |
| WO | WO 2015/018522 A1 | 2/2015 |
| WO | WO 2015/070020 A2 | 5/2015 |
| WO | WO 2015/078929 A1 | 6/2015 |
| WO | WO 2015/109286 A1 | 7/2015 |
| WO | WO 2017/027571 A8 | 2/2017 |

OTHER PUBLICATIONS

Partial European Search Report for 16835823.2 dated Mar. 21, 2019.
Extended European Search Report for 16835823.2 dated Jul. 3, 2019.
Invitation to Pay Additional Fees for PCT/US2016/046318 dated Oct. 5, 2016.
International Search Report and Written Opinion for PCT/US2016/046318 dated Dec. 16, 2016.
International Preliminary Report on Patentability for PCT/US2016/046318 dated Feb. 13, 2018.
STN Accession No. 0051983099. Sep. 22, 2015.
Alonso et al. Protein tyrosine phosphatases in the human genome. Cell. Jun. 11, 2004; 117(6):699-711.
Anders et al. Genome-wide localization of small molecules. Nat Biotechnol. Jan. 2014; 32(1): 92-6.
Arteaga et al. ERBB receptors: from oncogene discovery to basic science to mechanismbased cancer therapeutics. Cancer Cell. Mar. 17, 2014; 25(3): 282-303.
Belkina et al. BET domain co-regulators in obesity, inflammation and cancer. Nat Rev Cancer. Jul. 2012; 12(7): 465-77.
Bernardo et al. FOXA 1 is an essential determinant of ERalpha expression and mammary ductal morphogenesis. Development. Jun. 15, 2010; 137(12): 2045-54.
Bernardo et al. FOXA 1 represses the molecular phenotype of basal breast cancer cells. Oncogene. Jan. 2013; 32(5): 554-63.
Bernasconi et al., The BET bromodomain inhibitor OTX015 shows synergy with several anticancer agents in preclinical models of mantle cell lymphoma (MCL) and multiple myeloma (MM). Eur J. Cancer. Nov. 2, 2014;50(S6):184.
Bessarabova et al. Functional synergies yet distinct modulators affected by genetic alterations in common human cancers. Cancer Res. May 15, 2011; 71(10): 3471-81.
Bihani et al., Resistance to everolimus driven by epigenetic regulation of MYC in ER+ breast cancers. Oncotarget. Dec. 11, 2014; 6(4):2407-20.
Brown et al., NF-kappaB Directs Dynamic Super Enhancer Formation m Inflammation and Atherogenesis. Mal Cell. Oct. 23, 2014; 56(2): 219-31.
Cang et al., ABT-199 (venetoclax) and BCL-2 inhibitors in clinical development. J Hematol Oncol. Nov. 20, 2015; 8:129.
Chapuy et al. Discovery and characterization of super-enhancer-associated dependencies in diffuse large B cell lymphoma. Cancer Cell. Dec. 9, 2013; 24(6): 777-90.
Chou et al. Quantitative analysis of dose-effect relationships: the combined effects of multiple drugs or enzyme inhibitors. Advances in enzyme regulation. Jan. 1, 1984; 22: 27-55.
Choudhury et al. Molecular Profiling of Human Mammary Gland Links Breast Cancer Risk to a p27(+) Cell Population with Progenitor Characteristics. Cell stem cell. Jul. 3, 2013; 13(1): 117-30.
Choy et al. A cascade of irxla and irx2a controls shh expression during retinogenesis. Dev Dyn. Dec. 2010; 239(12): 3204-14.
Chung et al. Discovery and characterization of small molecule inhibitors of the BET family bromodomains. J. Med. Chem. Jun. 9, 2011; 54(11):3827-38.
Chung et al. Progress in the discovery of small-molecule inhibitors of bromodomain—histone interactions. J. Biomol Screen. Dec. 2011; 16(10):1170-85.
Cohen et al. Protein serine/threonine phosphatases; an expanding family. FEBS Lett. Aug. 1, 1990;268(2):355-9.
Delmore et al. BET bromodomain inhibition as a therapeutic strategy to target c-Myc. Cell. Sep. 16, 2011; 146(6): 904-17.
Dey et al. Brd4 marks select genes on mitotic chromatin and directs postmitotic transcription. Mal Biol Cell. Dec. 1, 2009; 20(23): 4899-909.
Disis et al., Avelumab (MSB0010718C), an anti-PD-L1 antibody, in patients with previously treated, recurrent or refractory ovarian cancer: A phase Ib, open-label expansion trial. J Clinical Oncology. May 20, 2015;33(15):5509-5509. Abstract only.
Eichhorn et al. R. Protein phosphatase 2A regulatory subunits and cancer. Biochim Biophys Acta. Jan. 1, 2009; 1795(1):1-15.
Engelman et al. MET amplification leads to gefitinib resistance in lung cancer by activating ERBB3 signaling. Science. May 18, 2007; 316(5827):1039-43.

(56) References Cited

OTHER PUBLICATIONS

Filippakopoulos et al. Benzodiazepines and benzotriazepines as protein interaction inhibitors targeting bromodomains of the BET family. Bioorg Med Chem. Mar. 15, 2012;20(6):1878-86.
Filippakopoulos et al. Selective inhibition of BET bromodomains. Nature. Dec. 2010; 468(7327):1067-73.
Gutierrez et al. Phenothiazines induce PP2A-mediated apoptosis in T cell acute lymphoblastic leukemia. J Clin Invest. Feb. 3, 2014; 124(2): 644-55.
Hayashi et al. The OCT4 pseudogene POU5F1B is amplified and promotes an aggressive phenotype in gastric cancer. Oncogene. Jan. 2013; 34(2):199-208.
Heiser et al. Subtype and pathway specific responses to anticancer compounds in breast cancer. Proc Natl Acad Sci U S A; Feb. 21, 2012; 109(8):2724-9.
Higgins et al. Targeted therapies for breast cancer. J Clin Invest. Oct. 2011; 121(1):3797-803.
Hnisz et al. Super-enhancers in the control of cell identity and disease. Cell. Nov. 7, 2013; 155(4): 934-47.
Janssens et al. Protein phosphatase 2A: a highly regulated family of serine/threonine phosphatases implicated in cell growth and signalling. Biochem J. Feb. 1, 2001; 353(Pt 3):417-39.
Jiang et al. Mammalian mediator of transcriptional regulation and its possible role as an end-point of signal transduction pathways. Proc Natl Acad Sci U S A. Jul. 21, 1998; 95(15): 8538-43.
Kumar et al. GL12-dependent c-MYC upregulation mediates resistance of pancreatic cancer cells to the BET bromodomain inhibitor JQ1. Scientific Reports. Mar. 25, 2015; 5:9489.
Langmead et al. Ultrafast and memory-efficient alignment of short DNA sequences to the human genome. Genome Biol. Mar. 2009; 10(3): R25.
Lechward et al. Protein phosphatase 2A: Variety of forms and diversity of functions. Acta Biochim Pol. Jan. 1, 2001; 48(4):921-33.
Lee et al., Synergistic effect of JQ1 and rapamycin for treatment of human osteosarcoma. International Journal of Cancer. May 1, 2015; 136:2055-64.
Lehmann et al. Identification of human triple-negative breast cancer subtypes and preclinical models for selection of targeted therapies. J Clin Invest. Jul. 1, 2011; 121(7):2750-67.
Lin et al., Transcriptional amplification in tumor cells with elevated c-Myc. Cell. Sep. 28, 2012; 151(1): 56-67.
Liu et al. Knockdown of IRX2 inhibits osteosarcoma cell proliferation and invasion by the AKT/MMP9 signaling pathway. Molecular medicine reports. Jul. 1, 2014; 10(1): 169-74.
Loven et al. Selective inhibition of tumor oncogenes by disruption of super-enhancers. Cell. Apr. 11, 2013; 153(2): 320-34.
Marotta et al. The JAK2/STAT3 signaling pathway is required for growth of CD44CD24 stem cell-like breast cancer cells in human tumors. J Clin Invest. Jul. 1, 2011; 121(7): 2723-35.
Meggio et al. One-thousand-and-one substrates of protein kinase CK2? Faseb J. Mar. 2003; 17(3): 349-68.
Mellacheruyu et al. The CRAPome: a contaminant repository for affinity purification-mass spectrometry data. Nat Methods. Aug. 2013; 10(8): 730-6.
Metzger-Filho et al. Dissecting the heterogeneity of triple-negative breast cancer. J Clin Oncol. Mar. 26, 2012; 30(15): 1879-87.
Mohammed et al. Endogenous purification reveals GREB 1 as a key estrogen receptor regulatory factor. Cell reports. Feb. 21, 2013; 3(2): 342-9.
Nagarajan et al. Bromodomain protein BRD4 is required for estrogen receptor-dependent enhancer activation and gene transcription. Cell reports. Jul. 24, 2014; 8(2): 460-9.
Ott et al. BET bromodomain inhibition targets both c-Myc and IL7R in high-risk acute lymphoblastic leukemia. Blood. Oct. 4, 2012; 120: 2843-52.

Perou et al. Molecular portraits of human breast tumours. Nature. Aug. 2000; 406(6797): 747-52. Abstract only.
Puissant et al. Targeting MYCN in neuroblastoma by BET bromodomain inhibition. Cancer Discov. Mar. 1, 2013; 3(3): 308-23.
Rahman et al. The Brd4 extraterminal domain confers transcription activation independent of pTEFb by recruiting multiple proteins, including NSD3. Mal Cell Biol. Jul. 1, 2011; 31(13): 2641-52.
Rincon et al. PP2A inhibition determines poor outcome and doxorubicin resistance in earlybreast cancer and its activation shows promising therapeutic effects. Oncotarget. Feb. 2015; 6(6): 4299-314.
Schroder et al. Two-pronged binding with bromodomain-containing protein 4 liberates positive transcription elongation factor b from inactive ribonucleoprotein complexes. J Biol Chem. Jan. 6, 2012; 287(2): 1090-9.
Semenza, HIF-1 mediates metabolic responses to intratumoral hypoxia and oncogenic mutations. J Clin Invest. Sep. 3, 2013; 123(9): 3664-71.
Shah et al. The clonal and mutational evolution spectrum of primary triple- negative breast cancers. Nature. Jun. 2012; 486(7403):395-9.
Shi et al. Disrupting the interaction of BRD4 with diacetylated Twist suppresses tumorigenesis in basal-like breast cancer. Cancer Cell. Feb. 10, 2014; 25(2): 210-25.
Shu et al. Response and resistance to BET bromodomain inhibitors in triple-negative breast cancer. Nature. Jan. 21, 2016; 529:413-7.
Smith et al. Enhancer biology and enhanceropathies. Nature structural & molecular biology. Mar. 2014; 21(3): 210-9. Abstract only.
Tawfic et al. Protein kinase CK2 signal in neoplasia. Histol. HistopathoL. Apr. 5, 2001; 16(2):573-82.
Trapnell et al. Transcript assembly and quantification by RNA-Seq reveals unannotated transcripts and isoform switching during cell differentiation. Nat Biotechnol. May 2010; 28(5): 511-5.
Trapnell et al., TopHat: discovering splice junctions with RNA-Seq. Bioinformatics. May 1, 2009; 25(9): 1105-11.
Vaz-Luis et al. Outcomes by tumor subtype and treatment pattern in women with small, node-negative breast cancer: a multi-institutional study. J Clin Oneal. Jul. 10, 2014; 32(20): 2142-50.
Virshup et al. Protein phosphatase 2A: a panoply of enzymes. Curr Opin Cell Biol. Apr. 2000; 12(2):180-5. Abstract only.
Watanabe et al. Activation and regulation of the pattern recognition receptors in obesity-induced adipose tissue inflammation and insulin resistance. Nutrients. Sep. 2013; 5(9): 3757-78.
Westermarck et al. Multiple pathways regulated by the tumor suppressor PP2A in transformation. Trends Mol Med. Apr. 1, 2008; 14(4): 152-60.
Whyte et al. Master transcription factors and mediator establish super-enhancers at key cell identity genes. Cell. Apr. 11, 2013; 153(2): 307-19.
Wu et al. Phosphoswitch triggers Brd4 chromatin binding and activator recruitment for gene-specific targeting. Mal Cell. Mar. 7, 2013; 49(5): 843-57.
Wu et al. The double bromodomain-containing chromatin adaptor Brd4 and transcriptional regulation. J Biol Chem. May 4, 2007; 282(18): 13141-5.
Yang et al. Brd4 recruits P-TEFb to chromosomes at late mitosis to promote G 1 gene expression and cell cycle progression. Mal Cell Biol. Feb. 1, 2008; 28(3): 967-76.
Yang et al. Recruitment of P-TEFb for stimulation of transcriptional elongation by the bromodomain protein Brd4. Mal Cell. Aug. 19, 2005; 19(4): 535-45.
Zhang et al. Model-based analysis of ChIP-Seq (MACS). Genome Biol. Nov. 2008; 9(9): R137.
Zuber et al. RNAi screen identifies Brd4 as a therapeutic target in acute myeloid leukemia. Nature. Oct. 2011; 478(7370): 524-8.
Ohama, Targeting PP2A inhibitors as a novel anti-cancer strategy. Folia Pharmacol. Japan. 2015;145:293-298.

* cited by examiner

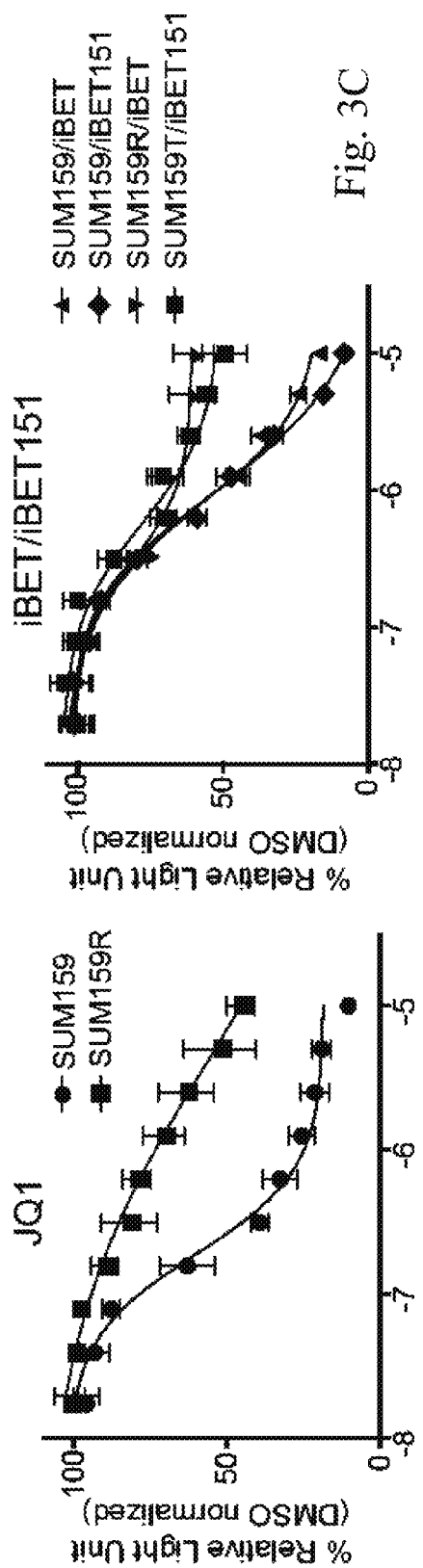
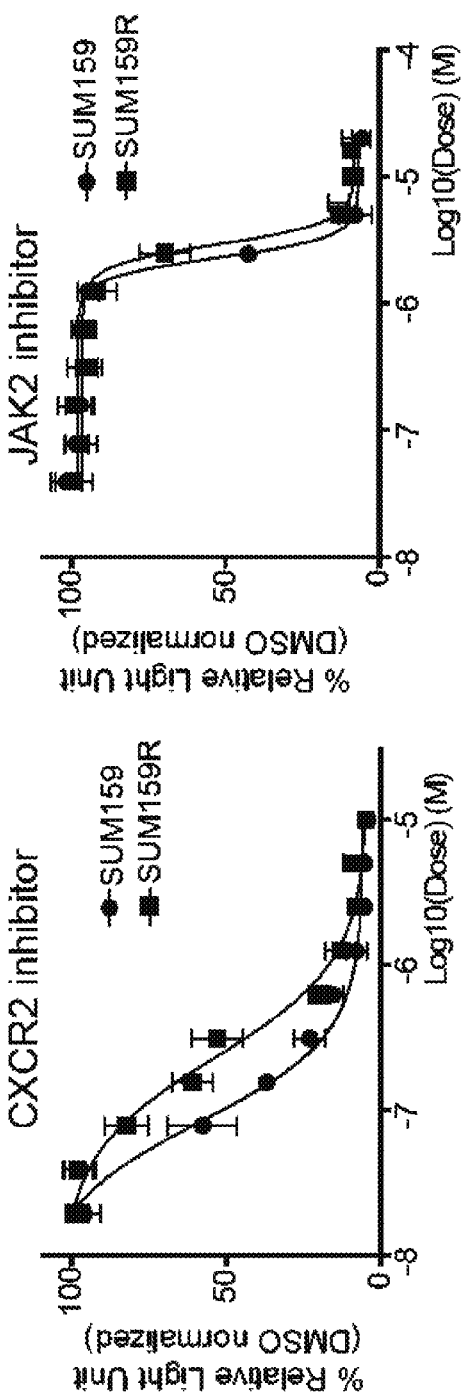
Fig. 3C
Fig. 3D

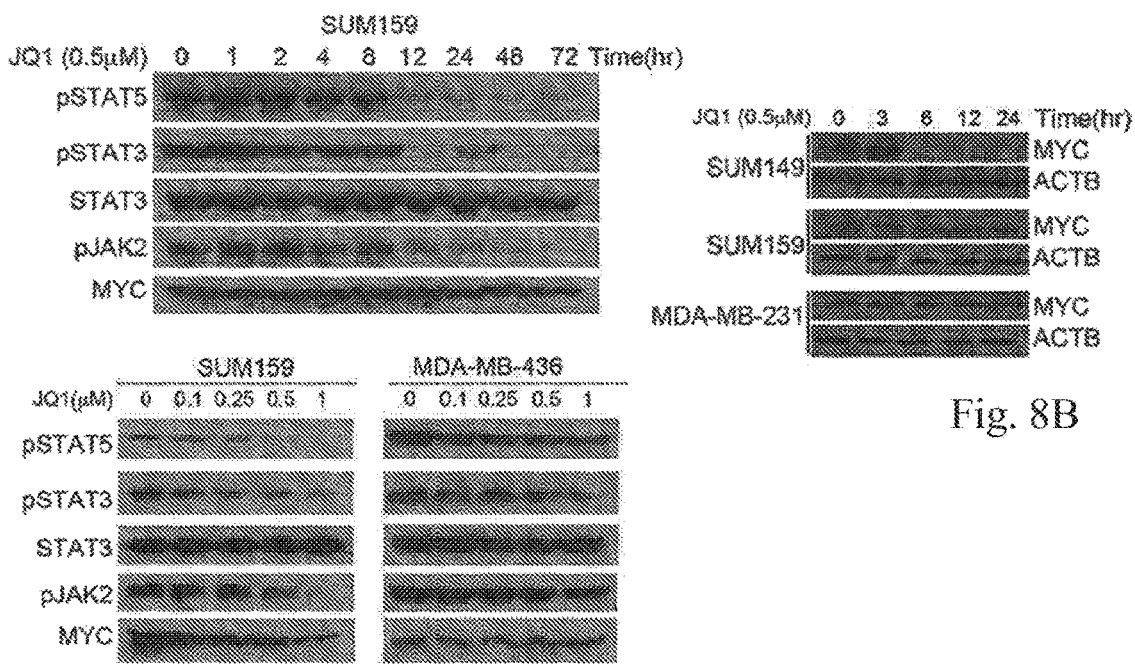
Fig. 8A
Fig. 8B
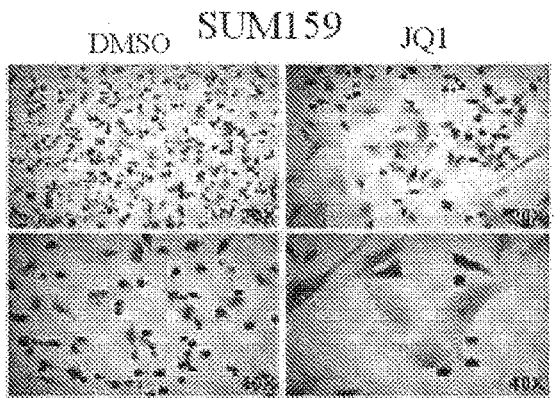
Fig. 8C
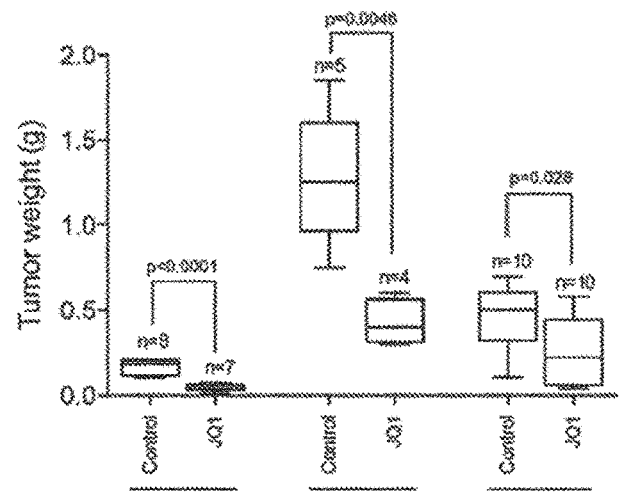
Fig. 8E
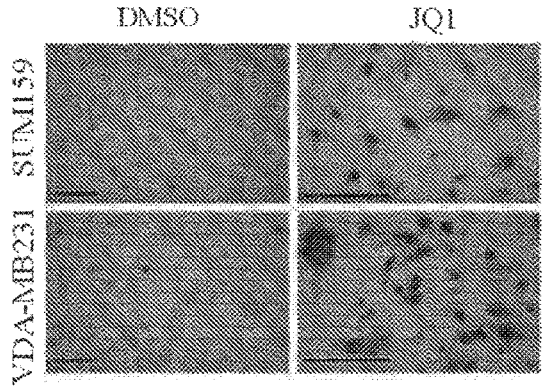
Fig. 8D

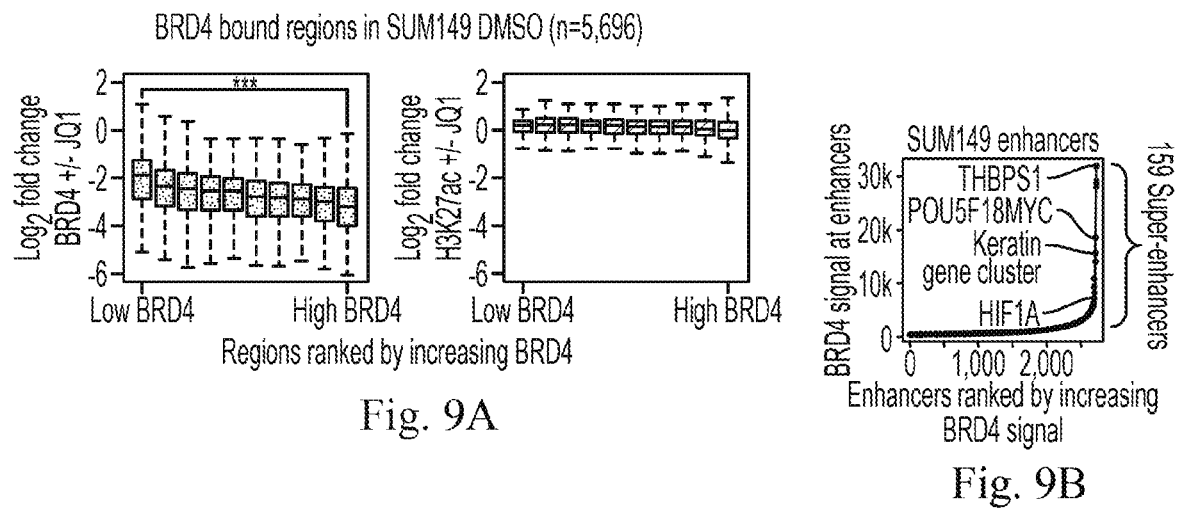
Fig. 9A
Fig. 9B
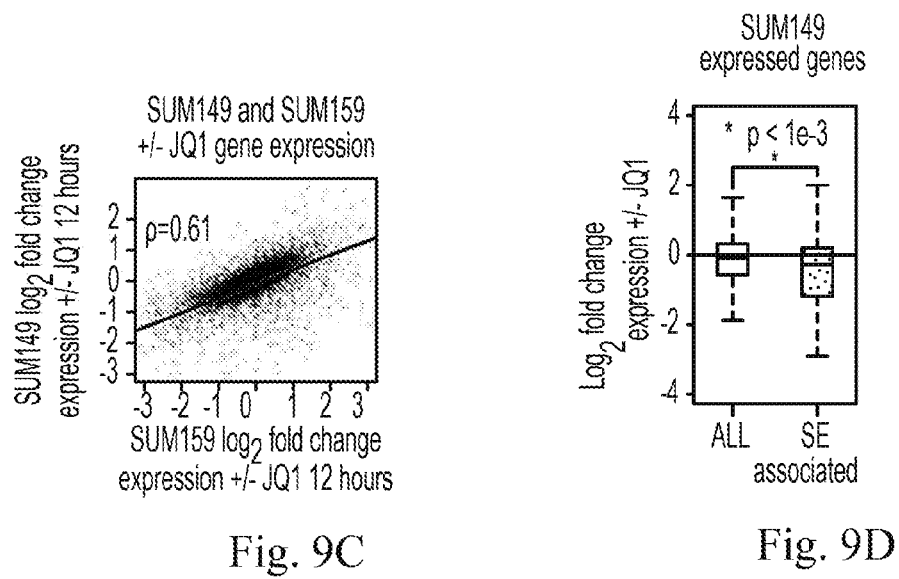
Fig. 9C
Fig. 9D

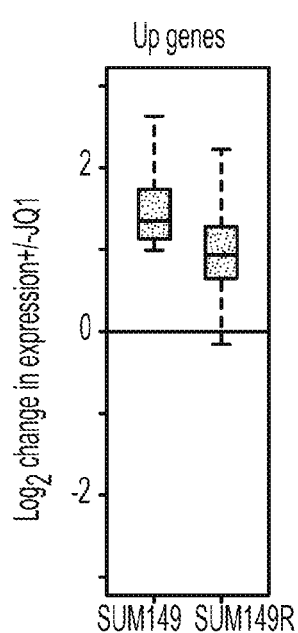
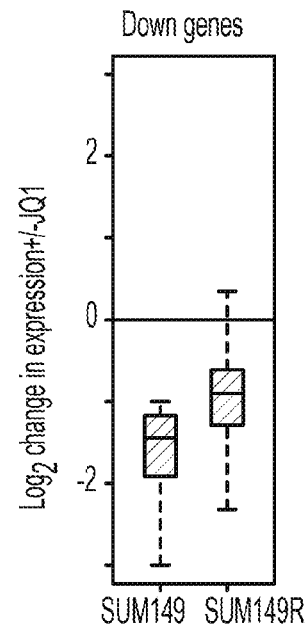
Fig. 9E    Fig. 9F
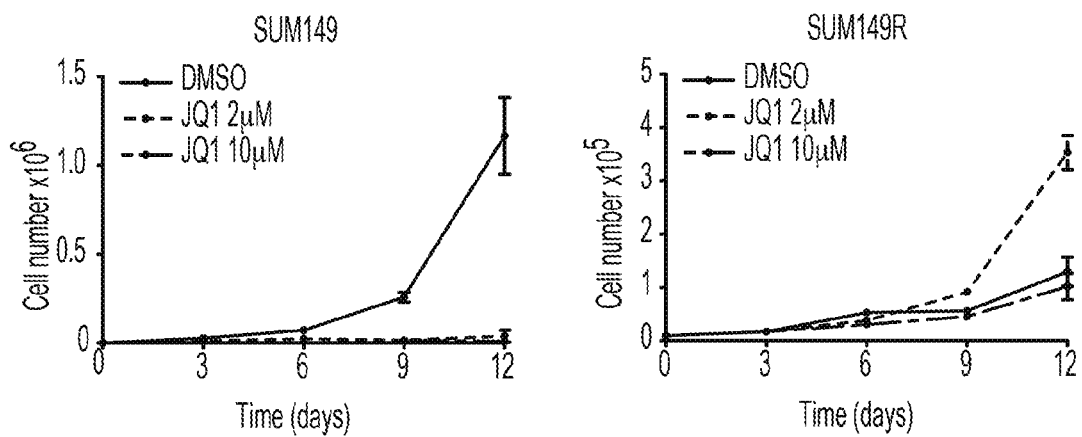
Fig. 9G

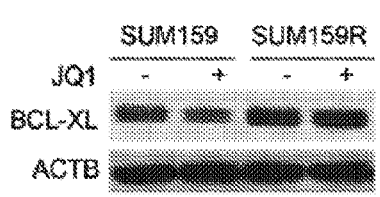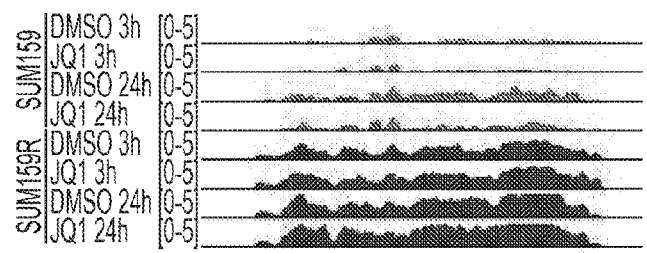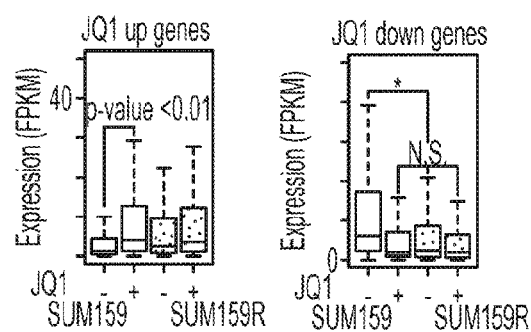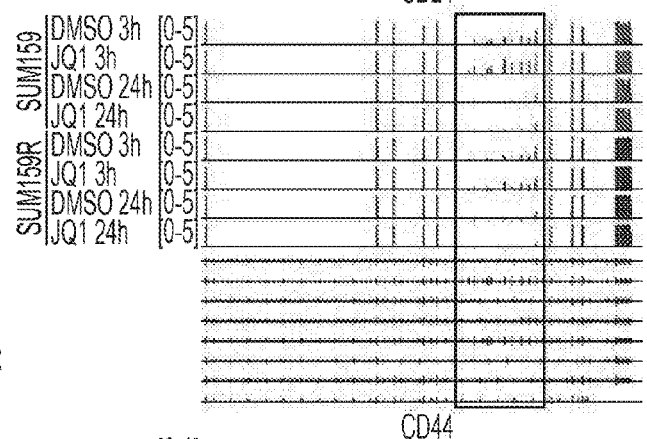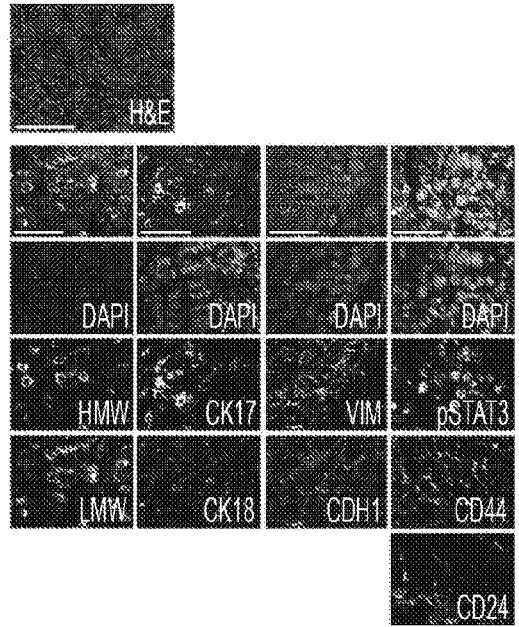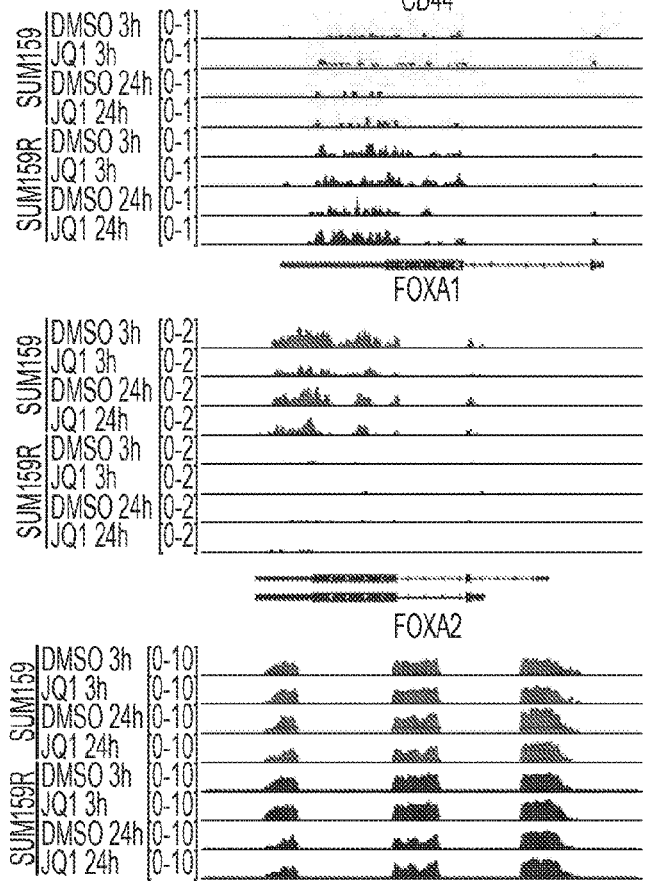
Fig. 11A
Fig. 11B
Fig. 11D
Fig. 11C

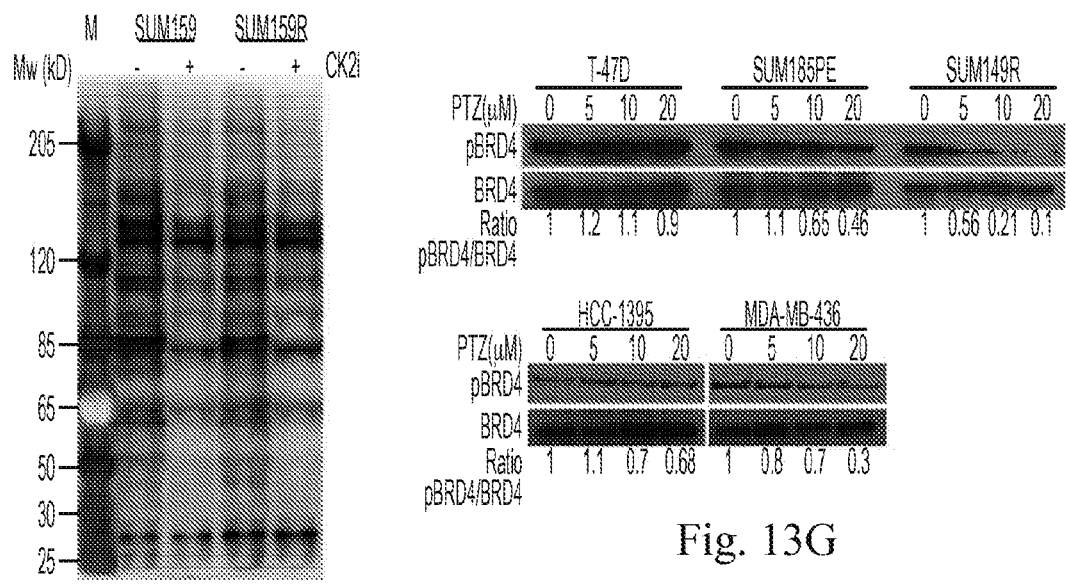
Fig. 13F
Fig. 13G
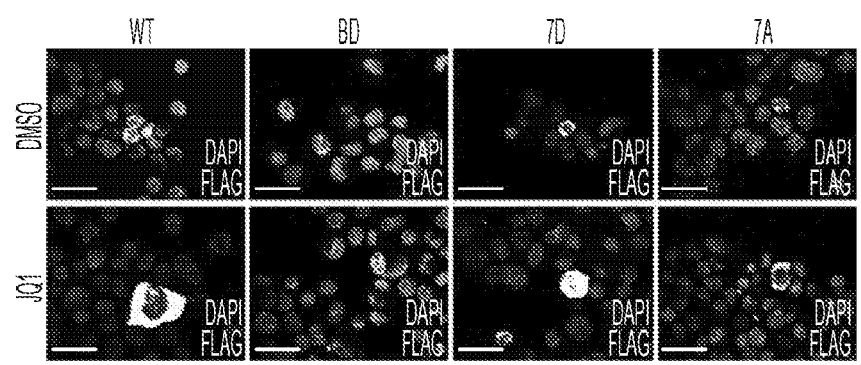
Fig. 13H

SEQUENCE LISTING

<160> NUMBER OF SEQ ID NOS: 23

<210> SEQ ID NO 1
<211> LENGTH: 25
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: modified by a ribose sugar

```
<400> SEQUENCE: 1
ggaccaaaug gcagccugau uacca                                          25

<210> SEQ ID NO 2
<211> LENGTH: 25
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: modified by a ribose sugar

<400> SEQUENCE: 2
gcaccagcug gcuguggguc cugag                                          25

<210> SEQ ID NO 3
<211> LENGTH: 25
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: modified by a ribose sugar

<400> SEQUENCE: 3
cuggcacuga cuuugccuug aacag                                          25

<210> SEQ ID NO 4
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: modified by a ribose sugar

<400> SEQUENCE: 4
ccuccagaca caauggcacu gcuta                                          25

<210> SEQ ID NO 5
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: modified by a ribose sugar

<400> SEQUENCE: 5
cagaugacau agugcuaa                                                  18

<210> SEQ ID NO 6
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: modified by a ribose sugar
```

```
<400> SEQUENCE: 6
gcuuugucaa cacgcauu                                                18

<210> SEQ ID NO 7
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: modified by a ribose sugar

<400> SEQUENCE: 7
ccauguucac caacuguu                                                18

<210> SEQ ID NO 8
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: modified by a ribose sugar

<400> SEQUENCE: 8
gcaauggcac gaaagcua                                                18

<210> SEQ ID NO 9
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: modified by a ribose sugar

<400> SEQUENCE: 9
gcucaagaca cuauggaa                                                18

<210> SEQ ID NO 10
<211> LENGTH: 18
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: modified by a ribose sugar

<400> SEQUENCE: 10
ugaucacaau caagucua                                                18

<210> SEQ ID NO 11
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 11
```
ctatgtttac aaattgttac atctacgcca agcctggaga tgacatagtc tt        52

<210> SEQ ID NO 12
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 12
gttctccaac tgctataagt acgcccctcc tgaccatgag                      40

<210> SEQ ID NO 13
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 13
cctggagatg acatagtctt a                                          21

<210> SEQ ID NO 14
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 14
ccaaccaaag tcagttcctt c                                          21

<210> SEQ ID NO 15
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 15
gccccgcccg catccagcga cgccagcagc gatgcctccg cggacagtga c         51

<210> SEQ ID NO 16
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 16
gtcactgtcc gcggaggcat cgctgctggc gtcgctggat gcgggcgggg c         51

<210> SEQ ID NO 17
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 17
tccgcggaca gtgacgctgc gactgatgac gctgaggagg agcgagcc             48

<210> SEQ ID NO 18
<211> LENGTH: 48
<212> TYPE: DNA
<213> ORGANISM: Artificial Sequence

```
<220> FEATURE:
<223> OTHER INFORMATION: Synthetic Polynucleotide

<400> SEQUENCE: 18
ggctcgctcc tcctcagcgt catcagtcgc agcgtcactg tccgcgga                    48

<210> SEQ ID NO 19
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 19
gccccgcccg attccagcga cgacagcagc gatgactccg acgacagtga c                51

<210> SEQ ID NO 20
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 20
gtcactgtcg tcggagtcat cgctgctgtc gtcgctggaa tcgggcgggg c                51

<210> SEQ ID NO 21
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 21
tccgacgaca gtgacgatga cactgatgac gatgaggagg agcgagcc                    48

<210> SEQ ID NO 22
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 22
ggctcgctcc tcctcatcgt catcagtgtc atcgtcactg tcgtcgga                    48

<210> SEQ ID NO 23
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 23
cccatgttgt tctttgttat t                                                 21
```

MECHANISM OF RESISTANCE TO BET BROMODOMAIN INHIBITORS

RELATED APPLICATIONS

This application is a national stage filing under 35 U.S.C. § 371 of International Application No. PCT/US2016/046318, filed Aug. 10, 2016, which claims priority under 35 U.S.C. § 119(e) to U.S. provisional application No. 62/203,128, filed Aug. 10, 2015, the contents of which are incorporated herein by reference in their entirety.

GOVERNMENT SUPPORT

This invention was made with government support under grant numbers CA168504, CA103867, CA120184 and CA089393 awarded by the National Institutes of Health and grant number W81XWH-13-1-0142 under the Department of Defense. The government has certain rights in the invention.

BACKGROUND OF THE INVENTION

Triple negative breast cancer (TNBC) is a major breast tumor subtype characterized by the absence of estrogen receptor (ER) and progesterone receptor (PR) expression, and the lack of human epidermal growth factor receptor 2 (HER2) amplification. TNBC patients experience a poor clinical outcome owing to a 5-year risk of recurrence that is higher than any other subtype, notably at distant sites. Cancer genome sequencing studies focusing on TNBC failed to identify novel recurrently mutated cancer-driving genes, obviating immediate opportunities for targeted therapeutic development. TNBC is also a heterogeneous disease, suggesting that one treatment may not suit all patients and that multiple new treatment strategies will be required. Hence, new therapeutic options for TNBC are urgently needed.

Bromodomain and extra terminal (BET) proteins (BRD2, BRD3 and BRD4) localize to promoter and enhancer regions via twin acetyl-lysine recognition modules (bromodomains). There, they facilitate transcriptional elongation by recruitment of the positive transcription factor elongation complex (CDK9 and Cyclin T; P-TEFb). Acetyl-lysine competitive binding by BET bromodomain inhibitors (BBI), such as JQ1, displaces BETs from chromatin resulting in selective transcriptional responses and anti-proliferative efficacy in models of hematologic malignancies and solid tumors. However, adaptive resistance disease to BET inhibitors is a common theme in the widespread literature on BBI in cancer, yet mechanistic insights are completely lacking. Thus, there is a need to find new treatments for cancers that are or may become resistant to BBI.

SUMMARY OF THE INVENTION

Some aspects of the disclosure provide a method for treating a cancer. The method comprises administering to a subject in need thereof a bromodomain and extra terminal (BET) inhibitor and a protein phosphatase 2A (PP2A) activator in an amount effective to treat the cancer.

In some embodiments, the cancer is resistant to treatment by the BET inhibitor alone.

In some embodiments, the BET inhibitor and the PP2A activator are synergistic in treating the cancer, compared to the BET inhibitor alone or the PP2A activator alone.

In some embodiments, the BET inhibitor is a bromodomain-containing protein 2 (BRD2) inhibitor, bromodomain-containing protein 3 (BRD3) inhibitor, or bromodomain-containing protein 4 (BRD4) inhibitor. In some embodiments, the BET inhibitor is a small molecule. In some embodiments, the BET inhibitor is JQ1 or a derivative thereof.

In some embodiments, the PP2A activator is a small molecule. In some embodiments, the PP2A activator is a phenothiazine compound or FTY720. In some embodiments, the phenothiazine compound is selected from the group consisting of chlorpromazine, mesoridazine, thioridazine, acetophenazine, fluphenazine, perphenazine, trifluoperazine and pharmaceutically acceptable salts and esters thereof.

In some embodiments, the BET inhibitor and the PP2A activator are administered concurrently or sequentially.

In some embodiments, the method further comprises administering to the subject a B-cell lymphoma-2 (Bcl-2) inhibitor, a B-cell lymphoma-extra large (Bcl-xl) inhibitor, a casein kinase 2 (CK2) inhibitor, and/or a mediator complex subunit 1 (MED1) inhibitor.

Some aspects of the disclosure provide a method for treating cancer, the method comprising: administering to a subject in need thereof a bromodomain and extra terminal (BET) inhibitor and a B-cell lymphoma-extra large (Bcl-xl) inhibitor in an amount effective to treat the cancer.

In some embodiments, the cancer is resistant to treatment by the BET inhibitor alone.

In some embodiments, the BET inhibitor and the Bcl-xl inhibitor are synergistic in treating the cancer, compared to the BET inhibitor alone or the Bcl-xl inhibitor alone.

In some embodiments, the BET inhibitor is a bromodomain-containing protein 2 (BRD2) inhibitor, bromodomain-containing protein 3 (BRD3) inhibitor, or bromodomain-containing protein 4 (BRD4) inhibitor. In some embodiments, the BET inhibitor is a small molecule. In some embodiments, the BET inhibitor is JQ1 or a derivative thereof.

In some embodiments, the Bcl-xl inhibitor is a small molecule. In some embodiments, the Bcl-xl inhibitor is ABT 737, ABT-263, AT101, Sabutoclax or TW-37.

In some embodiments, the BET inhibitor and the Bcl-xl inhibitor are administered concurrently or sequentially.

In some embodiments, the method further comprises administering to the subject a protein phosphatase 2A (PP2A) activator, a B-cell lymphoma-2 (Bcl-2) inhibitor, a casein kinase 2 (CK2) inhibitor, and/or a mediator complex subunit 1 (MED1) inhibitor.

Some aspects of the disclosure provide a method for treating cancer, the method comprising: administering to a subject in need thereof a bromodomain and extra terminal (BET) inhibitor and a casein kinase 2 (CK2) inhibitor in an amount effective to treat the cancer.

In some embodiments, the cancer is resistant to treatment by the BET inhibitor alone.

In some embodiments, the BET inhibitor and the CK2 inhibitor are synergistic in treating the cancer, compared to the BET inhibitor alone or the CK2 inhibitor alone.

In some embodiments, the BET inhibitor is a bromodomain-containing protein 2 (BRD2) inhibitor, bromodomain-containing protein 3 (BRD3) inhibitor, or bromodomain-containing protein 4 (BRD4) inhibitor. In some embodiments, the BET inhibitor is a small molecule. In some embodiments, the BET inhibitor is JQ1 or a derivative thereof.

In some embodiments, the CK2 inhibitor is a small molecule. In some embodiments, the CK2 inhibitor is CX-4945, DMAT, ellagic acid, or TTP22.

In some embodiments, the BET inhibitor and the CK2 inhibitor are administered concurrently or sequentially.

In some embodiments, the method further comprises administering to the subject a protein phosphatase 2A (PP2A) activator, a B-cell lymphoma-2 (Bcl-2) inhibitor, a B-cell lymphoma-extra large (Bcl-xl) inhibitor, and/or a mediator complex subunit 1 (MED1) inhibitor.

Some aspects of the disclosure provide a method for treating cancer, the method comprising: administering to a subject in need thereof a bromodomain and extra terminal (BET) inhibitor and a mediator complex subunit 1 (MED1) inhibitor in an amount effective to treat the cancer.

In some embodiments, the cancer is resistant to treatment by the BET inhibitor alone.

In some embodiments, the BET inhibitor and the MED1 inhibitor are synergistic in treating the cancer, compared to the BET inhibitor alone or the MED1 inhibitor alone.

In some embodiments, the BET inhibitor is a bromodomain-containing protein 2 (BRD2) inhibitor, bromodomain-containing protein 3 (BRD3) inhibitor, or bromodomain-containing protein 4 (BRD4) inhibitor. In some embodiments, the BET inhibitor is a small molecule. In some embodiments, the BET inhibitor is JQ1 or a derivative thereof.

In some embodiments, the MED1 inhibitor disrupts interaction between MED1 and BRD4. In some embodiments, the MED1 inhibitor is a small molecule, antibody, peptide or antisense compound.

In some embodiments, the BET inhibitor and the MED1 inhibitor are administered concurrently or sequentially.

In some embodiments, the method further comprises administering to the subject a protein phosphatase 2A (PP2A) activator, a B-cell lymphoma-2 (Bcl-2) inhibitor, a B-cell lymphoma-extra large (Bcl-xl) inhibitor, and/or a casein kinase 2 (CK2) inhibitor.

Some aspects of the disclosure provide a method to identify a subject having a cancer that is resistant to or at risk of developing resistance to bromodomain and extra terminal (BET) inhibitor therapy, the method comprising: performing an assay to determine intracellular location of bromodomain-containing protein 4 (BRD4) in a tumor sample obtained from a subject receiving BET inhibitor therapy; and identifying the subject as having a cancer that is resistant to or at risk of developing resistance to BET inhibitor therapy if the BRD4 has a nuclear localization.

In some embodiments, the subject is identified as having a cancer that is not resistant to BET inhibitor therapy if the BRD4 has a cytoplasmic localization.

In some embodiments, the method further comprises treating the subject identified as having a cancer resistant to BET inhibitor therapy by administering a BET inhibitor in combination with a protein phosphatase 2A (PP2A) activator, a B-cell lymphoma-2 (Bcl-2) inhibitor, a B-cell lymphoma-extra large (Bcl-xl) inhibitor, a casein kinase 2 (CK2) inhibitor, and/or a mediator complex subunit 1 (MED1).

In some embodiments, the assay comprises immunohistochemistry, immunofluorescence, radioimmunoassay, ELISA or FACS analysis. In some embodiments, the intracellular location of BRD4 is determined using antibodies in conjunction with immunofluorescence.

Some aspects of the disclosure provide a method to identify a subject having a cancer that is resistant to or at risk of developing resistance to bromodomain and extra terminal (BET) inhibitor therapy, the method comprising: performing an assay to determine a ratio of phosphorylated bromodomain-containing protein 4 (pBRD4) to un-phosphorylated BRD4 (BRD4) in a tumor sample obtained from a subject having a cancer; and identifying the subject as having a cancer that is resistant to or at risk of developing resistance to BET inhibitor therapy if the ratio of pBRD4 to BRD4 is increased as compared to a control ratio of pBRD4 to BRD4.

In some embodiments, the subject is identified as having a cancer that is not resistant to BET inhibitor therapy if the ratio of pBRD4 to BRD4 is decreased or is unchanged as compared to a control ratio of pBRD4 to BRD4.

In some embodiments, the method further comprises treating the subject identified as having a cancer resistant to BET inhibitor therapy by administering a BET inhibitor in combination with a protein phosphatase 2A (PP2A) activator, a B-cell lymphoma-2 (Bcl-2) inhibitor, a B-cell lymphoma-extra large (Bcl-xl) inhibitor, a casein kinase 2 (CK2) inhibitor, and/or a mediator complex subunit 1 (MED1).

In some embodiments, the assay comprises immunoblotting, immunohistochemistry, immunofluorescence, radioimmunoassay, ELISA or FACS analysis.

In some embodiments, the ratio of pBRD4 to BRD4 is determined by immunoblotting.

Some aspects of the disclosure provide a method for treating cancer, the method comprising: administering to a subject in need thereof a bromodomain and extra terminal (BET) inhibitor and a B-cell lymphoma-2 (Bcl-2) inhibitor in an amount effective to treat the cancer.

In some embodiments, the cancer is resistant to treatment by the BET inhibitor alone.

In some embodiments, the BET inhibitor and the Bcl-2 inhibitor are synergistic in treating the cancer, compared to the BET inhibitor alone or the Bcl-2 inhibitor alone.

In some embodiments, the BET inhibitor is a bromodomain-containing protein 2 (BRD2) inhibitor, bromodomain-containing protein 3 (BRD3) inhibitor, or bromodomain-containing protein 4 (BRD4) inhibitor. In some embodiments, the BET inhibitor is a small molecule. In some embodiments, the BET inhibitor is JQ1 or a derivative thereof.

In some embodiments, the Bcl-2 inhibitor is a small molecule. In some embodiments, the Bcl-2 inhibitor is ABT-199.

In some embodiments, the BET inhibitor and the Bcl-2 inhibitor are administered concurrently or sequentially.

In some embodiments, the method further comprises administering to the subject a protein phosphatase 2A (PP2A) activator, a B-cell lymphoma-extra large (Bcl-xl) inhibitor, a casein kinase 2 (CK2) inhibitor, and/or a mediator complex subunit 1 (MED1) inhibitor.

Each of the embodiments and aspects of the invention can be practiced independently or combined. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the inventions, as well as various advantages and utilities will be apparent with reference to the Detailed Description. Each aspect of the invention can encompass various embodiments as will be understood.

All documents identified in this application are incorporated in their entirety herein by reference.

BRIEF DESCRIPTION OF THE DRAWINGS

FIG. 1A, Heatmap of mean IC50s of BET inhibitors and inactive analogues (JQ1R and alprazolam) as negative controls in a panel of TNBC, HER2+, and luminal breast cancer, and immortalized basal mammary epithelial cell lines. IC50 values in a colorimetric scale: very sensitive (<0.01 μM), sensitive (=1 μM), to resistant (>20 μM). FIG. 1B, Cellular viability four days after transfection of siRNAs targeting BET bromodomain proteins. FIG. 1C, Cell cycle profile of SUM159 cells synchronized in G2/M with 100 ng/mL nocodazole followed by replating to fresh medium with DMSO or JQ1 (500 nM) added at −1 h or at 3 h after release. Cells were collected at different time points (0, 6, 12 h) after release. FIG. 1D, Immunoblot analysis of the indicated proteins in a panel of breast cell lines. FIG. 1E, Immunofluorescence of basal (high molecular weight—HMW) and luminal (low molecular weight—LMW and cytokeratin 18) cytokeratins in TNBC lines before and 3 days after JQ1 (500 nM) treatment. Scale bars show 20 μm. FIG. 1F, Box plots depict the weights of xenografts 28 and 60 days after injection of parental and TET-inducible shBRD4-expressing SUM159 cells into mammary fat pads; n indicates the number of mice/experiment. Mice were administered JQ1 (50 mg/kg, daily), vehicle only (control) for 14 days beginning at day 14 (SUM159), or doxycycline at day 21 (SUM159-shBRD4) after injection. FIG. 1G, Hematoxylin-eosine staining and immunofluorescence analysis of basal (HMW cytokeratin, cytokeratin 17, pSTAT3, and CD44) and luminal (LMW cytokeratin, cytokeratin 18, and CD24) markers in SUM159 xenografts with or without JQ1 treatment. Scale bars show 100 m for H&E and 50 μm for immunofluorescence, respectively.

FIG. 2A, Heatmap showing biotinylated JQ1 (Bio-JQ1), BRD4, and H3K27ac binding at promoter transcription start site (TSS) regions and Bio-JQ1 bound TSS distal enhancer regions (right). Each row represents a single genomic region (+/−10 kb) from either the TSS or enhancer center. Genomic occupancy is shaded by binding intensity in units of reads per million per base pair (rpm/bp) for Bio-JQ1, BRD4, and H3K27ac. FIG. 2B, Scatter plots showing the relationship between the genomic binding of BRD4 and Bio-JQ1 (left) or H3K27ac and Bio-JQ1 (right) at all Bio-JQ1 enriched bound regions. Units of genomic occupancy are in rpm/bp. A simple linear regression is drawn in black. Pearson correlation statistics are also shown. FIG. 2C, Gene tracks depicting Bio-JQ1, BRD4+DMSO, and BRD4+JQ1 in SUM159 cells at the HIF1A gene locus. The x-axis shows position along the chromosome with gene structures drawn below. The y-axis shows genomic occupancy in units of rpm/bp. The HIF1A super-enhancer is shown as a bold line. FIG. 2D, Boxplots showing the $\log_2$ fold change in BRD4+/−JQ1 (left) or H3K27ac+/−JQ1 (right) at Bio-JQ1 bound regions in SUM159. The 12,999 Bio-JQ1 regions are ranked by increasing Bio-JQ1 binding and divided into 10 separate bins (displayed from left to right). The statistical significance of the difference in the mean BRD4 $\log_2$ fold change between the weakest and strongest Bio-JQ1 bound region bins is shown (Welch's t-test *p-value <1 e-10). FIG. 2E, Ranked plots of enhancers defined in untreated SUM159 cells ranked by increasing Bio-JQ1 signal (units rpm). Enhancers are defined as regions of Bio-JQ1 binding not contained in promoters. The cutoff discriminating typical from super-enhancers is shown as a dashed gray line. Enhancers associated with TNBC characteristic genes are highlighted. FIG. 2F, Boxplots showing the $\log_2$ fold change in expression relative to DMSO control of either all active genes or super-enhancer (SE) associated upon JQ1 treatment at 3, 12, and 24 hours after treatment. The statistical significance of the difference in expression change between all active genes and super-enhancer associated genes is shown by a Welch's t-test p-value <1 e-5, *p-value <1 e-3). FIG. 2G, Top signaling pathways affected by JQ1-induced gene expression changes in SUM159 cells.

FIGS. 3A-3G. Acquired BBI resistance in TNBC. FIGS. 3A-3B, Viable cell numbers of SUM159 (FIG. 3A) and SUM159R cells (FIG. 3B) treated with different doses of JQ1. Error bars represent SD. FIGS. 3C-3D, Cellular viability of SUM159 and SUM159R cells treated with BBIs (FIG. 3C) or CXCR2 and JAK2 inhibitors (FIG. 3D). FIG. 3E, Cellular viability of SUM159, and pool and single cell clones of SUM159R cells treated with different doses of JQ1. FIG. 3F, Tumor weight of xenografts derived from SUM159 and SUM159R cells. Mice were administered JQ1 for 14 (SUM159) and 30 (SUM159R) days beginning at day 14 and 26, respectively, after injection. FIG. 3G, Cellular viability of SUM159 and SUM159R cells transfected with siRNAs targeting bromodomain proteins. Error bars represent SEM in panels FIGS. 3C-3G.

FIG. 4A, All genomic regions containing a super-enhancer (as defined by Bio-JQ1 binding) in SUM159 parental or SUM159R are shown ranked by $\log_2$ change in Bio-JQ1 genomic binding signal (parental vs. resistant). X-axis shows the $\log_2$ fold change in Bio-JQ1 signal. Change in Bio-JQ1 levels are colored by intensity of change. FIG. 4B, Boxplot showing the $\log_2$ fold change in BRD4 genomic occupancy at regions with either gained, conserved, or lost (left, center, right) Bio-JQ1 binding in resistant SUM159R vs. parental SUM159 cells. FIG. 4C, Boxplot showing the $\log_2$ fold change in expression at genes proximal to regions with either gained, conserved, or lost (left, center, right) Bio-JQ1 binding in resistant SUM159R vs. parental SUM159 cells. FIG. 4D, Gene tracks depicting Bio-JQ1, BRD4, and H3K27ac in SUM159 parental (top) or SUM159R resistant (bottom) cells at the SUM159R gained BCL-xL gene locus. The x-axis shows position along the chromosome with gene structures drawn below. The y-axis shows genomic occupancy in units of rpm/bp. The BCL-xL super-enhancer is shown as a bar. FIG. 4E, Gene tracks depicting Bio-JQ1, BRD4+/−JQ1, and H3K27ac+/−JQ1 in SUM159 parental (top) or SUM159R resistant (bottom) cells at the Bio-JQ1 bound SOD2 gene locus. The x-axis shows position along the chromosome with gene structures drawn below. The y-axis shows genomic occupancy in units of rpm/bp. The SOD2 super-enhancer is shown as a bar. FIGS. 4F-4G, Boxplots showing the log 2 fold change in BRD4 (FIG. 4F) or H3K27ac (FIG. 4G) genomic occupancy at regions bound by Bio-JQ1 in either with either parental SUM159 (left) or resistant SUM159R (right) cells. FIGS. 4H-4I, Boxplots showing the $\log_2$ fold change in expression at genes that are up (FIG. 4H) or down (FIG. 4I) regulated by JQ1 versus DMSO after 24 hours of treatment in parental SUM159 cells. $\log_2$ fold change in expression is shown for either parental SUM159 (left) or resistant SUM159R (right) cells.

FIG. 5A, Plot depicting changes in BRD4-associated proteins in SUM159 and SUM159R cells following JQ1 treatment based on SILAC RIME. The axes represent log 10 of fold change (FC). FIG. 5B, Immunoblot analysis of BRD4 immunoprecipitates (top panel) and total cell lysates (bottom panel) in SUM159 and SUM159R cells. FIG. 5C, Cellular viability of SUM159 and SUM159R cells expressing exogenous WT, BDmut, 7A and 7D mutant BRD4 with concomitant knock-down of endogenous BRD4. FIGS. 5D-5E, Sensitivity of SUM159 (FIG. 5D) and SUM159R (FIG. 5E) cells expressing exogenous WT or BDmut BRD4 to JQ1 with concomitant knock-down of endogenous BRD4.

FIG. 6A, Immunoblot analysis of phosphorylated BRD4 (pBRD4), BRD4, MED1, and BRD3 in SUM159 and SUM159R cells following treatment with the indicated doses of JQ1. FIG. 6B, Immunoblot analysis of PP2A A and C subunits, pBRD4 and BRD4 in SUM149 and SUM159 cells after knock-down of PP2A-A, PP2A-C or both subunits. FIG. 6C, Viable cell numbers of control and SUM149 and shPP2A-C expressing SUM149 cells treated with different doses of JQ1. Error bars represent SEM. FIG. 6D, Immunoblot analysis of pBRD4 and BRD4 in SUM159R cells following 3 hours treatment with different doses of phenothiazine. FIG. 6E, Viable cell numbers of SUM159R cells treated with JQ1, phenothiazine or both compounds. Error bars represent SD. FIG. 6F, Immunoblot analysis of BRD4 immunoprecipitates and total cell lysates of SUM159R cells after 3 hrs treatment with JQ1 (5 JIM) and CK2 inhibitor CX-4945 (10 µM). FIG. 6G, Immunoblot analysis of BRD4 immunoprecipitates and total cell lysates of SUM159R cells after 3 hrs treatment with JQ1 (5 µM) and phenothiazine (20 µM). FIG. 6H, Immunoblot analysis of FLAG-BRD4 immunoprecipitates and total cell lysates of SUM159 cells expressing FLAG-tagged WT or mutant (7A, 7D) BRD4 mutant proteins after 3 hrs treatment with JQ1 (5 µM). FIG. 6I, JQ1 sensitivity of SUM159 and SUM159R cells expressing exogenous WT, 7A or 7D mutant BRD4. Error bars represent SEM.

FIG. 7A, Cellular viability of SUM159 and MDA-MB-231 cells expressing TET-inducible BRD4-targeting or lacZ shRNAs. FIG. 7B, Immunoblot analysis of BET bromodomain proteins four days after siRNA transfection. FIG. 7C, Immunoblot analysis of the indicated proteins at different time points (0, 3, 6, 12 h) after release of SUM159 cells synchronized with 100 ng/ml nocodazole followed by replating to fresh medium with DMSO or JQ1 (500 nM) added at 1 hr before or 3 hrs after release. FIG. 7D, Cell cycle analysis of SUM159 cells following 72 hr treatment with JQ1 (500 nM) or downregulation of BRD4 using TET-inducible shRNAs. FIG. 7E, Annexin V staining of SUM159 cells following 72 hr treatment with JQ1 (500 nM) downregulation of BRD4 using TET-inducible shRNAs. All error bars represent SEM.

FIGS. 8A-8G. Response to BBIs in TNBCs. FIG. 8A, Immunoblot analysis of the indicated proteins at different time points following JQ1 treatment (500 nM) in SUM159 cells (top) and at different JQ1 doses for 24 h treatment in SUM159 and MDA-MB-436 cells (bottom). FIG. 8B, Immunoblot analysis of the indicated proteins at different time points following JQ1 treatment (500 nM) in SUM149, SUM159 and MDA-MB-231 cells. FIG. 8C, H&E staining of SUM159 cells after 3 days of JQ1 treatment. FIG. 8D, -Senescence β-galactosidase staining of SUM159 and MDA-MB-231 cells after 3 days of JQ1 treatment. Scale bars show 100 µm. FIG. 8E, Box plots depict the weights of xenografts 30 days after injection of MDA-MB-231 ($2\times10^6$) and IDC50X ($2\times10^5$) cells into inguinal mammary fat pads of NOG mice; n indicates the number of mice/experiment. Mice were administered JQ1 (50 mg/kg, daily) or vehicle only (control) for 14 days beginning at day 16 (MDA-MB-231) or 10 (IDC50X) after injection (after tumors reached palpable size). For EL12-58X PDX, mice were implanted with pieces of tissue measuring 1×3×3 mm into the inguinal mammary fat pads and were administered daily JQ1 (50 mg/kg) for 14 days beginning at day 21 after injection (after tumors reached palpable size). FIG. 8F, Bromodeoxyuridine (BrdU) and luminal low (Low MW CK) and basal high (High MW CK) molecular weight cytokeratin staining of EL12-58 xenograft with or without JQ1 treatment. Scale bars show 50 µm. FIG. 8G, Tumor volume of SUM159 cells expressing TET-inducible BRD4-targeting shRNAs. Mice were administered doxycycline or vehicle only (control) for 39 days beginning at day 21 after injection (after tumors reached palpable size). All error bars represent SEM.

FIGS. 9A-9G. SUM149 JQ1 response. FIG. 9A, Boxplots showing the $\log_2$ fold change in BRD4+/−JQ1 (left) or H3K27ac+/−JQ1 (right) at BRD4 bound regions in SUM149. The 5,696 BRD4 bound regions are ranked by increasing background subtracted BRD4 binding and divided into 10 separate bins (displayed from left to right). The statistical significance of the difference in the mean BRD4 $\log_2$ fold change between the weakest and strongest BRD4 bound region bins is shown (Welch's t-test ***p-value <1 e-10). FIG. 9B, Ranked plots of enhancers defined in untreated SUM149 cells ranked by increasing BRD4 signal (units rpm). Enhancers are defined as regions of BRD4 binding not contained in promoters. The cutoff discriminating typical from super-enhancers is shown as a dashed gray line. Enhancers associated with TNBC characteristic genes are highlighted. FIG. 9C, Scatter plots showing the relationship between the log 2 fold change in gene expression upon 12 hr JQ1 treatment in SUM149 (y-axis) and SUM159 (x-axis). A simple linear regression is drawn. The Pearson correlation statistic is also shown. FIG. 9D, Boxplots showing the $\log_2$ fold change in expression relative to DMSO control of either all active genes or super-enhancer (SE) associated upon 12 hr JQ1 treatment. The statistical significance of the difference in expression change between all active genes and super-enhancer associated genes is shown by a Welch's t-test *p-value <1 e-3). FIGS. 9E-9F, Boxplots showing the $\log_2$ fold change in expression at genes that are up (FIG. 9E) or down (FIG. 9F) regulated by JQ1 versus DMSO after 12 hours of treatment in parental SUM149 cells. $\log_2$ fold change in expression is shown for either parental SUM149 (left) or resistant SUM149R (right) cells. FIG. 9G, Viable cell numbers of SUM149 (left) and SUM149R (right) treated with different doses of JQ1 (2 µM, 10 µM). Error bars represent SD.

FIG. 10A, Expression of ABC transporters in SUM159 and SUM159R cells. The expression of 29 ABC transporters was analyzed based on RNA-seq data on the two cell lines. FIG. 10B, Assay for MDR (multi drug resistance) pumps in SUM159 and SUM159R cells treated with JQ1 alone or together with verapamil based on microscopic examination (left) and FACS (right) of cells labeled with fluorescent MDR substrate. FIG. 10C, Immunoprecipitation analysis of Biotinylated JQ1 (Bio-JQ1) in SUM159 and SUM159R cells with JQ1 treatment at different time points following immunoblot for the indicated proteins. FIG. 10D, Cellular viability of SUM159R cells expressing TET-inducible BRD4-targeting or lacZ shRNAs. All error bars represent SEM.

FIGS. 11A-11D. BRD4 binding in SUM159R cells. FIG. 11A, Immunoblot analysis of BCL-XL expression in SUM159 and SUM159R cells before and after JQ1 3 h treatment (500 nM). FIG. 11B, Boxplots showing expression of genes that are up or down regulated by JQ1 versus DMSO after 24 hours of treatment in parental SUM159 cells.

Expression is shown in DMSO and JQ1-treated conditions in units of FPKM for either parental SUM159 (left) or resistant SUM159R (right) cells. The statistical significance of the difference between gene expression distributions for SUM159 DMSO and JQ1 treated cells is shown (p<0.01). The difference between all other distributions are considered non significant (N.S). The statistical significance of the difference between SUM159 DMSO gene expression distribution and all other distributions is shown (*p-value <1 e-3). The difference between all other distributions are considered non significant. FIG. 11C, Examples of luminal and basal cell-specific genes, and MYC in SUM159 and SUM159R cells. RNA-seq tracks are shown. FIG. 11D, H&E staining and immunofluorescence analysis of luminal (CK18 and HMW) and basal (CK17 and LMW) cytokeratins and luminal (VIM and CD24) and basal (CDH1, CD44, and pSTAT3) cell markers in SUM159R xenografts. All error bars represent SEM. Scale bars show 100 m for H&E and 50 μm for IF, respectively.

FIGS. 12A-12B, Gene tracks depicting BRD4+DMSO and BRD4+JQ1 in multiple TNBC cells at the BCL-xL (FIG. 12A) or SOD2 (FIG. 12B) gene loci. The x-axis shows position along the chromosome with gene structures drawn below. The y-axis shows genomic occupancy in units of rpm/bp. The BCL-xL and SOD2 super-enhancers are shown as a bar at the top. FIG. 12C, Box plots showing the log 2 fold change in BRD4 occupancy+/−JQ1 for all BRD4 bound regions in each cell line for multiple TNBC. Cell lines are ordered by their JQ1 (IC50) and colored by their sensitivity. FIG. 12D, Gene tracks depicting H3K27AC occupancy at the BCL-xL locus in SUM149 parental or SUM149R resistant cells. The x-axis shows position along the chromosome with gene structures drawn below. The y-axis shows genomic occupancy in units of rpm/bp. All error bars represent SEM.

FIGS. 13A-13H. Mechanism of BBI resistance. FIG. 13A, Immunoblot analysis of BRD4 immunoprecipitates for MED1 in the indicated cell lines with or without JQ1 treatment (5 uM, 3 h). FIG. 13B, Immunoblot analysis of long (BRD4L) and short (BRD4S) forms of BRD4 after transfection of siRNAs. FIG. 13C, Immunoblot analysis of the indicated exogenously expressed FLAG-tagged BRD4 proteins in SUM159 and SUM159R cells. FIG. 13D, Immunoblot analysis of phospho-BRD4 (pBRD4) and BRD4 in SUM159 and SUM159R cells treated with the indicated doses of CK2, PI3K, and MEK inhibitors for 2 hrs. FIG. 13E, Immunoblot analysis of pBRD4, BRD4, MED1 and ACTB in the indicated cell lines with or without JQ1 treatment. FIG. 13F, Immunoblot analysis of CK2 substrates in SUM159 and SUM159R cells following CK2 inhibitor (CX-4945, 10 μM) 3 h treatment. FIG. 13G, Immunoblot analysis of pBRD4 and BRD4 in the indicated cell lines treated with different doses of phenothiazine for 6 hrs. FIG. 13H, Immunofluorescence analysis of exogenous FLAG-tagged BRD4 proteins (WT, BD, 7D and 7A) in SUM159 cells with or without JQ1 treatment (5 μM, 3 hrs). Scale bars show 20 μm.

FIGS. 14A-14C, Synergy studies of JQ1 with ABT737 (BCL-xl and BCL-2 inhibitor) (FIG. 14A), CX-4945 (CK2 inhibitor) (FIG. 14B) and Perphenazine (PP2A activator) (FIG. 14C). Points represent paired values of drug concentrations assessed for synergism. The diagonal line signifies drug additivity. Points above the line represent antagonistic drug combinations, and those below the line represent synergistic drug combinations.

DETAILED DESCRIPTION OF THE INVENTION

Figure 1A:
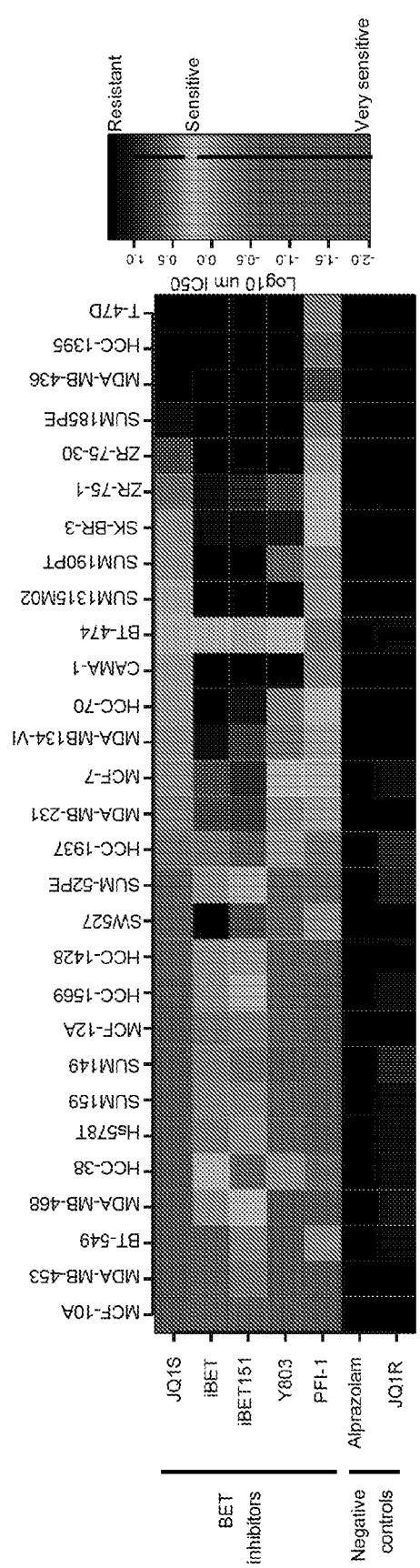
FIGS. 1A-1G. Response to BBIs in breast cancer. All error bars represent SEM.

The present disclosure provides methods to identify and treat subjects that are resistant to therapy with BET bromodomain inhibitors (BBI) or that are likely to become resistant to therapy with BBI. Some aspects of the disclosure relate to treating such cancers using combination therapy.

It has been found, in accordance with the invention, that cancers resistant to BBI remain dependent on wild-type BRD4, which supports transcription and cell proliferation in a bromodomain-independent manner. In resistant cells, BRD4 is recruited to chromatin due to its hyper-phosphorylation, attributable to decreased activity of protein phosphatase 2A (PP2A; presently identified as a principal BRD4 serine phosphatase), and increased binding to mediator complex subunit 1 (MED1). Inhibiting BRD4 phosphorylation in resistant cells using modulators of BRD4 phosphorylation, such as casein kinase II (CK2) inhibitors or PP2A activators, led to decreased MED1 abundance in BRD4 immunoprecipitation experiments, demonstrating that phosphorylated BRD4 (pBRD4) binds MED1 more efficiently than unphosphorylated BRD4.

In addition, differential super-enhancer (SE) analysis found a significant gain in the number of SEs in resistant cells that was associated with enrichment of BRD4 binding to these genomic loci and also with increased transcription of the associated genes. Among the top gained super-enhancers was an upstream and intragenic region of H3K27ac enrichment at the BCL-xL locus. Notably, BCL-xL and Bcl-2 were among the few, highly up-regulated genes in resistant cells by expression profiling, a finding that was confirmed by immunoblot and fluorescence imaging, respectively. Without wishing to be bound by any particular theory, deregulated, increased expression of these anti-apoptotic factors is expected to confer resistance to apoptosis during long-term treatment with BBI. Together, these findings provide a rationale for combination strategies to anticipate and overcome BBI resistance, such as pairing with PP2A activators, CK2 inhibitors, Bcl-2 inhibitors, BCL-xL inhibitors or MED1 inhibitors.

Significantly, substantial synergy was observed between BET bromodomain inhibitor, JQ1, and molecules targeting BCL-XL (ABT737), a CK2 inhibitor (CX-4945), a JAK2 inhibitor (INC 424), a Bcl-xl/Bcl-2 inhibitor (ABT 263), a Bcl-2 inhibitor (ABT 199), and a PP2A activator (perphenazine; PPZ), demonstrating that these drug combinations achieve higher efficacy in resistant cells.

Treatment Methods

Accordingly, aspects of the present disclosure provide a method for treating a cancer, the method comprising administering to a subject in need thereof a bromodomain and extra terminal (BET) inhibitor and a protein phosphatase 2A (PP2A) activator in an amount effective to treat the cancer.

Some aspects of the present disclosure provide a method for treating cancer, the method comprising administering to a subject in need thereof a bromodomain-containing protein inhibitor and a B-cell lymphoma-2 (Bcl-2) inhibitor in an amount effective to treat the cancer.

Some aspects of the present disclosure provide a method for treating cancer, the method comprising administering to a subject in need thereof a bromodomain-containing protein inhibitor and a B-cell lymphoma-extra large (Bcl-xl) inhibitor in an amount effective to treat the cancer.

Some aspects of the present disclosure provide a method for treating cancer, the method comprising administering to a subject in need thereof a bromodomain-containing protein inhibitor and a casein kinase 2 (CK2) inhibitor in an amount effective to treat the cancer.

Some aspects of the present disclosure provide a method for treating cancer, the method comprising administering to a subject in need thereof a bromodomain-containing protein inhibitor and a mediator complex subunit 1 (MED1) inhibitor in an amount effective to treat the cancer.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM). Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, triple negative breast cancer, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). In some embodiments, the cancer is breast cancer. In some embodiments, the cancer is triple negative breast cancer.

In some embodiments, the cancer is a resistant to treatment with a BET inhibitor. A cancer that is resistant to a BET inhibitor means that the cancer does not respond to such inhibitor, for example as evidenced by continued proliferation and increasing tumor growth and burden. In some instances, the cancer may have initially responded to treatment with such inhibitor (referred to herein as a previously administered therapy) but may have grown resistant after a time. In some instances, the cancer may have never responded to treatment with such inhibitor at all.

The terms "treatment," "treat," and "treating" refer to reversing, alleviating, delaying the onset of, or inhibiting the progress of cancer. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The terms "inhibition", "inhibiting", "inhibit," or "inhibitor" refer to the ability of a compound to reduce, slow, halt, and/or prevent activity of a particular biological process in a cell relative to vehicle. In some embodiments, "inhibit", "block", "suppress" or "prevent" means that the activity being inhibited, blocked, suppressed, or prevented is reduced by at least 5%, 10%, 15%, 20%, 25%, 30%, 35%, 40%, 45%, 50%, 55%, 60%, 65%, 70%, 75%, 80%, 85%, 90%, 95%, or 100% as compared to the activity of a control (e.g., activity in the absence of the inhibitor). In some embodiments, "inhibit", "block", "suppress" or "prevent" means that the expression of the target of the inhibitor (e.g. a bromodomain-containing protein) is reduced by at least 5%, 10%, 15%, 20%, 25%, 30%, 35%, 40%, 45%, 50%, 55%, 60%, 65%, 70%, 75%, 80%, 85%, 90%, 95%, 100% as compared to a control (e.g., the expression in the absence of the inhibitor).

An "effective amount" refers to an amount sufficient to elicit the desired biological response, i.e., treating cancer. As will be appreciated by those of ordinary skill in this art, the effective amount of the compounds described herein may vary depending on such factors as the desired biological endpoint, the pharmacokinetics of the compound, the condition being treated, the mode of administration, and the age and health of the subject. An effective amount includes, but is not limited to, that amount necessary to slow, reduce, inhibit, ameliorate or reverse one or more symptoms associated with cancer. For example, in the treatment of cancer, such terms may refer to a reduction in the size of the tumor.

Where two or more inhibitors are administered to the subject, the effective amount may be a combined effective amount. The effective amount of a first inhibitor may be different when it is used with a second and optionally a third inhibitor. When two or more inhibitors are used together, the effective amounts of each may be the same as when they are used alone.

Alternatively, the effective amounts of each may be less than the effective amounts when they are used alone because the desired effect is achieved at lower doses. Alternatively, again, the effective amount of each may be greater than the effective amounts when they are used alone because the subject is better able to tolerate one or more of the inhibitors which can then be administered at a higher dose provided such higher dose provides more therapeutic benefit.

An effective amount of a compound may vary from about 0.001 mg/kg to about 1000 mg/kg in one or more dose administrations, for one or several days (depending on the mode of administration). In certain embodiments, the effective amount varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg. One of ordinary skill in the art would be able to determine empirically an appropriate therapeutically effective amount.

As used throughout, the term "subject" or "patient" is intended to include humans and animals that are capable of suffering from or afflicted with a cancer or any disorder involving, directly or indirectly, a cancer. Examples of subjects include mammals, e.g., humans, dogs, cows, horses, pigs, sheep, goats, cats, mice, rabbits, rats, and transgenic non-human animals. In some embodiments, subjects include companion animals, e.g. dogs, cats, rabbits, and rats. In some embodiments, subjects include livestock, e.g., cows, pigs, sheep, goats, and rabbits. In some embodiments, subjects include thoroughbred or show animals, e.g. horses, pigs, cows, and rabbits. In important embodiments, the subject is a human, e.g., a human having, at risk of having, or potentially capable of having cancer.

A "subject in need of treatment" is a subject identified as having cancer, i.e., the subject has been diagnosed by a physician (e.g., using methods well known in the art) as having cancer. In some embodiments, the subject in need of treatment is a subject suspected of having or developing a cancer, such as a subject presenting one or more symptoms indicative of a cancer. The term "subject in need of treatment" further includes people who once had a cancer but whose symptoms have ameliorated. The one or more symptoms or clinical features of cancer depend on the type and location of the tumor. For example, lung tumors may cause coughing, shortness of breath, or chest pain. Tumors of the colon can cause weight loss, diarrhea, constipation, iron deficiency anemia, and blood in the stool. The following symptoms occur with most tumors: chills, fatigue, fever, loss of appetite, malaise, night sweats, and weight loss. The terms "administer," "administering," or "administration," as used herein refers to implanting, absorbing, ingesting, injecting, or inhaling the one or more therapeutic agents.

In some embodiments, the subject is further treated with one or more additional anti-neoplasia therapy. For example, the subject may undergo surgery, radiation therapy, chemotherapy, gene therapy, DNA therapy, viral therapy, RNA therapy, adjuvant therapy, immunotherapy or a combination thereof.

The compounds described herein can be administered to the subject in any order. A first therapeutic agent, such as BET inhibitor, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as a PP2A activator, a Bcl-2 inhibitor, a Bcl-xl inhibitor, a CK2 inhibitor or a MED1 inhibitor described herein, to a subject with cancer. Thus, BET inhibitors can be administered separately, sequentially or simultaneously with the second therapeutic agent, such as a PP2A activator, a Bcl-2 inhibitor, a Bcl-xl inhibitor, a CK2 inhibitor or a MED1 inhibitor described herein.

The compounds described herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds provided herein may be administered at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Bromodomain Inhibitors

Bromodomain inhibitors are known in the art. A bromodomain inhibitor is any molecule or compound that can prevent or inhibit, in part or in whole, the binding of at least one bromodomain to acetyl-lysine residues of proteins (e.g., to the acetyl-lysine residues of histones). The bromodomain inhibitor may be any molecule or compound that inhibits a bromodomain as described above, including nucleic acids such as DNA and RNA aptamers, antisense oligonucleotides, siRNA and shRNA, small peptides, antibodies or antibody fragments, and small molecules such as small chemical compounds. It is to be understood that the bromodomain inhibitor may inhibit only one bromodomain-containing protein or it may inhibit more than one or all bromodomain-containing proteins.

Examples of bromodomain inhibitors are described in JP 2009028043, JP 2009183291, WO 2011054843, WO 2011054848, WO2009/084693A1, WO2009084693, WO 2011054844, WO 2011054846, US 2012028912, Filippakopoulos et al. Bioorg Med Chem. 20(6): 1878-1886, 2012; Chung et al. J Med Chem. 54(11):3827-38, 2011; and Chung et al. J Biomol Screen. 16(10):1170-85, 2011, which are incorporated herein by reference.

In some embodiments, the bromodomain inhibitor is 1-[2-(1/-/-benzimidazol-2-ylthio)ethyl]-1,3-dihydro-3-methyl-2H-benzinidazole-2-thione (JP2008-156311), Alprazolam (Sigma-Aldrich), Midazolam (Sigma-Aldrich, GW841819X (BZD, GlaxoSmithKline), a compound in Table 1 (WO 2011054843), or any other bromodomain inhibitor compound described herein.

TABLE 1

Examples of Bromodomain inhibitors

| | Name | Structure |
|---|---|---|
| Example 1 | 1-methylethyl ((2S,4R)-1-acetyl-2-methyl-6-{4-[(methylamino)methyl]phenyl}-1,2,3,4-tetrahydro-4-quinolinyl)carbamate | 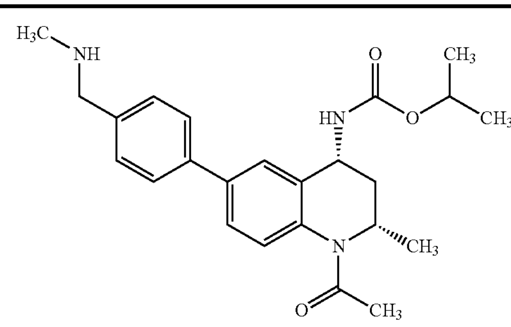 |

TABLE 1-continued

Examples of Bromodomain inhibitors

| Name | Structure |
| --- | --- |
| Example 2 2-[(4S)-6-(4-Chlorophenyl)-1-methyl-8-(methyloxy)-4H-[1,2,4]triazolo[4,3-a][1,4]benzodiazepin-4-yl]-N-ethylacetamide | |
| Example 3 7-(3,5-dimethyl-4-isoxazolyl)-8-(methoxy)-1-[(1R)-1-(2-pyridinyl)ethyl]-1,3-dihydro-2H-imidazo[4,5-c]quinolin-2-one | |
| Example 4 7-(3,5-dimethyl-4-isoxazolyl)-8-(methoxy)-1-[(1R)-1-phenylethyl]-2-(tetrahydro-2H-pyran-4-yl)-1H-imidazo[4,5-c]quinoiine | |
| Example 5 4-{(2S,4R)-1-acetyl-4-[(4-chlorophenyl)amino]-2-methyl-1,2,3,4-tetrahydro-6-quinolinyl}benzoic acid | |

TABLE 1-continued

Examples of Bromodomain inhibitors

| Name | Structure |
|---|---|
| Example 6 | N-{1-methyl-7-[4-(1-piperidinylmethyl)phenyl][1,2,4]triazolo[4,3-a]quinolin-4-yl}urea | 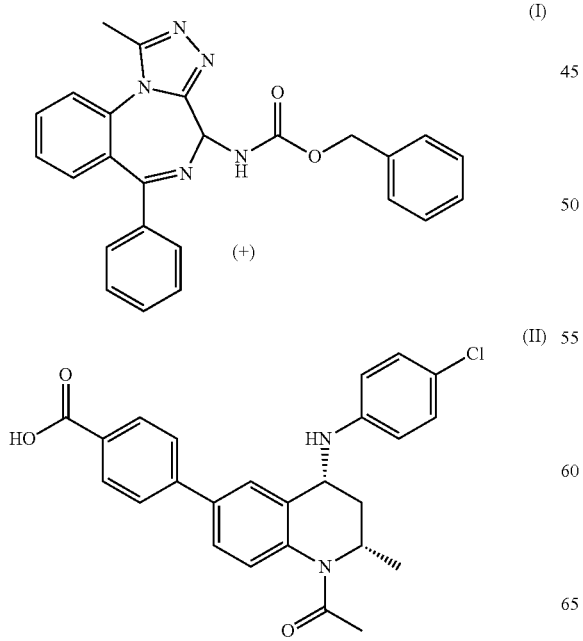 |

In some embodiments, the bromodomain inhibitor is a BET inhibitor. A BET inhibitor is any molecule or compound that can prevent or inhibit the binding of the bromodomain of at least one BET family member to acetyl-lysine residues of proteins. The BET inhibitor may be any molecule or compound that inhibits a BET as described above, including nucleic acids such as DNA and RNA aptamers, antisense oligonucleotides, siRNA and shRNA, small peptides, antibodies or antibody fragments, and small molecules such as small chemical compounds.

Examples of BET inhibitors are described in US 2011143651, WO2009/084693A1, WO 2011143669, WO 2011143660, WO 2011054851, and JP 2008156311, which are incorporated herein by reference. It is to be understood that a BET inhibitor may inhibit only one BET family member or it may inhibit more than one or all BET family members. Examples of BET inhibitors known in the art include, but are not limited to, RVX-208 (Resverlogix), PFI-1 (Structural Genomics Consortium), OTX015 (Mitsubishi Tanabe Pharma Corporation), BzT-7, GSK525762A (iBET, GlaxoSmithKline), and the compounds below (WO 2011054851, GlaxoSmithKline):

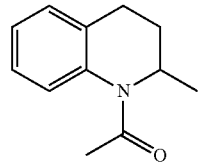

(III)

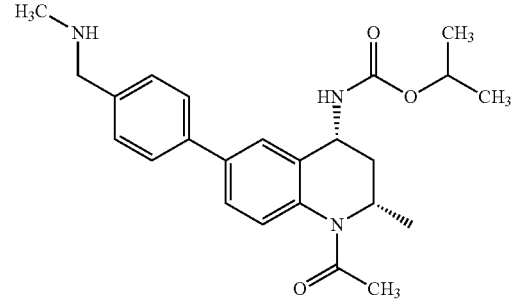 [SMILES: CNCc1ccc(-c2ccc3c(c2)[C@H](NC(=O)OC(C)C)C[C@H](C)N3C(C)=O)cc1]

(IV)

In some embodiments, the BET inhibitor is a small molecule compound (e.g., JQ1 or derivatives thereof and compounds of formulas I-XXII or any other compound described herein) that binds to the binding pocket of the first bromodomain of a BET family member (e.g., BRD1, BRD2, BRD3, BRD4, BRD7, BRDT; see WO 2011143669).

In some important embodiments, the BET inhibitor is JQ1 and has the formula below:

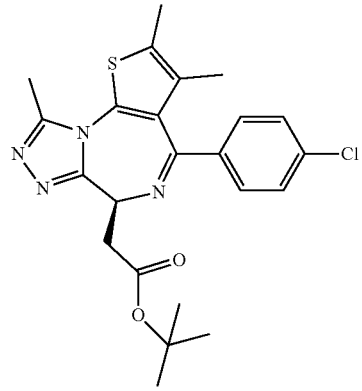

JQ1

In some embodiments, the BET inhibitor has the structures of Formulas I-XXII or any other compound as described below. These structures are known in the art (WO 2011143660, which is incorporated herein by reference).

In some embodiments, a bromodomain or BET inhibitor is a compound of Formula I:

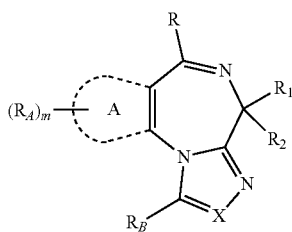

(I)

wherein X is N or $CR_5$; $R_5$ is H, alkyl, cycloalkyl, heterocycloalkyl, aryl, or heteroaryl, each of which is optionally substituted; $R_B$ is H, alkyl, hydroxylalkyl, aminoalkyl, alkoxyalkyl, haloalkyl, hydroxy, alkoxy, or —COO—R3, each of which is optionally substituted; ring A is aryl or heteroaryl; each $R_4$ is independently alkyl, cycloalkyl, heterocycloalkyl, aryl, or heteroaryl, each of which is optionally substituted; or any two $R_4$ together with the atoms to which each is attached, can form a fused aryl or heteroaryl group; R is alkyl, cycloalkyl, heterocycloalkyl, aryl, or heteroaryl; each of which is optionally substituted;

Ri is —$(CH_2)_n$-L, in which n is 0-3 and L is H, —COO—R3, —CO—R3, —CO—N($R_3R_4$), —S(O)$_2$—$R_3$, —S(O)$_2$—N($R_3R_4$), N($R_3R4$), N(R4)C(O)$R_3$, optionally substituted aryl, or optionally substituted heteroaryl;

$R_2$ is H, D (deuterium), halogen, or optionally substituted alkyl;

each $R_3$ is independently selected from the group consisting of:
(i) H, aryl, substituted aryl, heteroaryl, or substituted heteroaryl;
(ii) heterocycloalkyl or substituted heterocycloalkyl;
(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$Ci_2$ cycloalkyl, substituted —$C_3$-$Ci_2$ cycloalkyl, —$C_3$-$Ci_2$ cycloalkenyl, or substituted —$C_3$-$Ci_2$ cycloalkenyl, each of which may be optionally substituted; and
(iv) $NH_2$, N=$CR_4R_6$;
each $R_4$ is independently H, alkyl, alkyl, cycloalkyl, heterocycloalkyl, aryl, or heteroaryl,
each of which is optionally substituted;
or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;

m is 0, 1, 2, or 3;
provided that
(a) if ring A is thienyl, X is N, R is phenyl or substituted phenyl, $R_2$ is H, RB is methyl, and Ri is —$(CH_2)_n$-L, in which n is 1 and L is —CO—N($R_3R_4$), then $R_3$ and $R_4$ are not taken together with the nitrogen atom to which they are attached to form a morpholino ring;
(b) if ring A is thienyl, X is N, R is substituted phenyl, $R_2$ is H, RB is methyl, and Ri is —$(CH_2)_n$-L, in which n is 1 and L is —CO—N($R_3R_4$), and one of $R_3$ and $R_4$ is H, then the other of $R_3$ and $R_4$ is not methyl, hydroxyethyl, alkoxy, phenyl, substituted phenyl, pyridyl or substituted pyridyl; and
(c) if ring A is thienyl, X is N, R is substituted phenyl, $R_2$ is H, $R_B$ is methyl, and Ri is —$(CH_2)_n$-L, in which n is 1 and L is —COO—$R_3$, then $R_3$ is not methyl or ethyl; or a salt, solvate or hydrate thereof.

In certain embodiments, R is aryl or heteroaryl, each of which is optionally substituted.

In certain embodiments, L is H, —COO—$R_3$, —CO—N($R_3R_4$), —S(O)$_2$—$R_3$, —S(O)$_2$—N($R_3R_4$), N($R_3R_4$), N($R_4$)C(O)$R_3$ or optionally substituted aryl. In certain embodiments, each $R_3$ is independently selected from the group consisting of: H, —$C_1$-$C_8$ alkyl, which is optionally substituted, containing 0, 1, 2, or 3 heteroatoms selected from O, S, or N; or $NH_2$, N=$CR_4R_6$.

In certain embodiments, $R_2$ is H, D, halogen or methyl.
In certain embodiments, $R_B$ is alkyl, hydroxyalkyl, haloalkyl, or alkoxy; each of which is optionally substituted.
In certain embodiments, $R_B$ is methyl, ethyl, hydroxy methyl, methoxymethyl, trifluoromethyl, COOH, COOMe, COOEt, or COOCH$_2$OC(O)CH$_3$.

In certain embodiments, ring A is a 5 or 6-membered aryl or heteroaryl. In certain embodiments, ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, ring A is phenyl or thienyl.
In certain embodiments, m is 1 or 2, and at least one occurrence of $R_4$ is methyl.

In certain embodiments, each $R_4$ is independently H, an optionally substituted alkyl, or any two $R_4$ together with the atoms to which each is attached, can form an aryl.

In some embodiments, a bromodomain or BET inhibitor is a compound of Formula II:

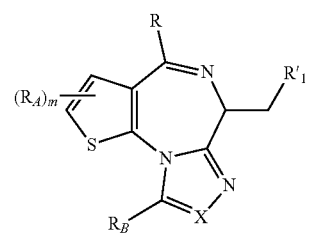

(II)

wherein X is N or $CR_5$; $R_5$ is H, alkyl, cycloalkyl, heterocycloalkyl, aryl, or heteroaryl, each of which is optionally substituted; $R_B$ is H, alkyl, hydroxylalkyl, aminoalkyl, alkoxyalkyl, haloalkyl, hydroxy, alkoxy, or —COO—$R_3$, each of which is optionally substituted;

each $R_4$ is independently alkyl, cycloalkyl, heterocycloalkyl, aryl, or
heteroaryl, each of which is optionally substituted; or any two $R_4$ together with the atoms to which each is attached, can form a fused aryl or heteroaryl group;

R is alkyl, cycloalkyl, heterocycloalkyl, aryl, or heteroaryl, each of which is optionally substituted;

R'i is H, —COO—$R_3$, —CO—$R_3$, optionally substituted aryl, or optionally substituted heteroaryl;

each $R_3$ is independently selected from the group consisting of:

(i) H, aryl, substituted aryl, heteroaryl, substituted heteroaryl;
(ii) heterocycloalkyl or substituted heterocycloalkyl;
(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl; each of which may be optionally substituted;

m is 0, 1, 2, or 3;

provided that if $R'_1$ is —COO—$R_3$, X is N, R is substituted phenyl, and $R_B$ is methyl, then $R_3$ is
not methyl or ethyl;
or a salt, solvate or hydrate thereof.

In certain embodiments, R is aryl or heteroaryl, each of which is optionally substituted. In certain embodiments, R is phenyl or pyridyl, each of which is optionally substituted. In certain embodiments, R is p-Cl-phenyl, o-Cl-phenyl, m-Cl-phenyl, p-F-phenyl, o-F-phenyl, m-F-phenyl or pyridinyl.

In certain embodiments, R'i is —COO—$R_3$, optionally substituted aryl, or optionally substituted heteroaryl; and $R_3$ is —$C_1$-$C_8$ alkyl, which contains 0, 1, 2, or 3 heteroatoms selected from O, S, or N, and which may be optionally substituted. In certain embodiments, R'i is —COO—$R_3$, and $R_3$ is methyl, ethyl, propyl, i-propyl, butyl, sec-butyl, or t-butyl; or R'i is H or optionally substituted phenyl.

In certain embodiments, $R_B$ is methyl, ethyl, hydroxymethyl, methoxymethyl, trifluoromethyl, COOH, COOMe, COOEt, COOCH$_2$OC(O)CH$_3$.

In certain embodiments, $R_B$ is methyl, ethyl, hydroxymethyl, methoxymethyl, trifluoromethyl, COOH, COOMe, COOEt, or COOCH$_2$OC(O)CH$_3$.

In certain embodiments, each $R_A$ is independently an optionally substituted alkyl, or any two $R_A$ together with the atoms to which each is attached, can form a fused aryl.

In certain embodiments, each $R_A$ is methyl.

In some embodiments, a bromodomain or BET inhibitor is a compound of formula III:

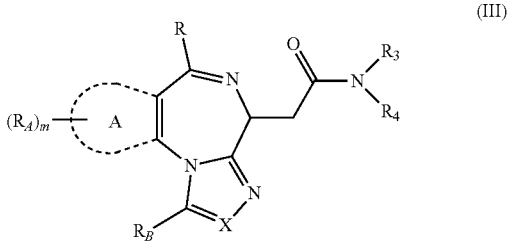

(III)

wherein
X is N or $CR_5$; $R_5$ is H, alkyl, cycloalkyl, heterocycloalkyl, aryl, or heteroaryl, each of which is optionally substituted; RB is H, alkyl, hydroxylalkyl, aminoalkyl, alkoxyalkyl, haloalkyl, hydroxy, alkoxy, or —COO—R3, each of which is optionally substituted; ring A is aryl or heteroaryl; each $R_A$ is independently alkyl, cycloalkyl, heterocycloalkyl, aryl, or heteroaryl, each of which is optionally substituted; or any two RA together with the atoms to which each is attached, can form a fused aryl or heteroaryl group;

R is alkyl, cycloalkyl, heterocycloalkyl, aryl, or heteroaryl, each of which is optionally substituted;

each $R_3$ is independently selected from the group consisting of:
(i) H, aryl, substituted aryl, heteroaryl, or substituted heteroaryl;

(ii) heterocycloalkyl or substituted heterocycloalkyl;
(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$Ci_2$ cycloalkyl, substituted —$C_3$-$Ci_2$ cycloalkyl, —$C_3$-$Ci_2$ cycloalkenyl, or substituted —$C_3$-$Ci_2$ cycloalkenyl, each of which may be optionally substituted; and
(iv) NH$_2$, N=CR$_4$R$_6$;

each $R_4$ is independently H, alkyl, alkyl, cycloalkyl, heterocycloalkyl, aryl, or heteroaryl, each of which is optionally substituted; or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;

m is 0, 1, 2, or 3;

provided that:
(a) if ring A is thienyl, X is N, R is phenyl or substituted phenyl, $R_B$ is methyl, then $R_3$ and $R_4$ are not taken together with the nitrogen atom to which they are attached to form a morpholino ring; and (b) if ring A is thienyl, X is N, R is substituted phenyl, $R_2$ is H, $R_B$ is methyl, and one of $R_3$ and $R_4$ is H, then the other of $R_3$ and $R_4$ is not methyl, hydroxyethyl, alkoxy, phenyl, substituted phenyl, pyridyl or substituted pyridyl;
or a salt, solvate or hydrate thereof.

In certain embodiments, R is aryl or heteroaryl, each of which is optionally substituted. In certain embodiments, R is phenyl or pyridyl, each of which is optionally substituted.

In certain embodiments, R is p-Cl-phenyl, o-Cl-phenyl, m-Cl-phenyl, p-F-phenyl, o-F-phenyl, m-F-phenyl or pyridinyl. In certain embodiments, $R_3$ is H, NH$_2$, or N=CR$_4$R$_6$.

In certain embodiments, each $R_4$ is independently H, alkyl, cycloalkyl, heterocycloalkyl, aryl, heteroaryl; each of which is optionally substituted.

In certain embodiments, $R_6$ is alkyl, alkenyl, cycloalkyl, cycloalkenyl, heterocycloalkyl, aryl, or heteroaryl, each of which is optionally substituted.

In some embodiments, a bromodomain or BET inhibitor is a compound of formula IV:

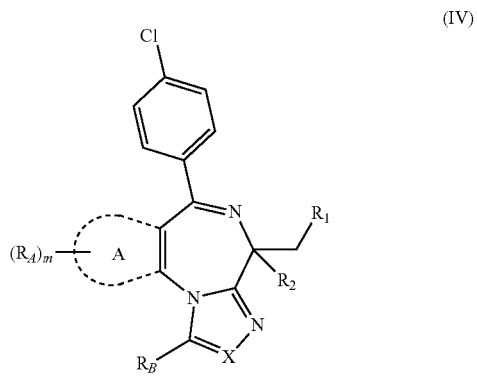

(IV)

wherein X is N or $CR_5$; $R_5$ is H, alkyl, cycloalkyl, heterocycloalkyl, aryl, or heteroaryl, each of which is optionally substituted;

$R_B$ is H, alkyl, hydroxylalkyl, aminoalkyl, alkoxyalkyl, haloalkyl, hydroxy, alkoxy, or —COO—R3, each of which is optionally substituted;

ring A is aryl or heteroaryl;

each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;

Ri is —$(CH_2)_n$-L, in which n is 0-3 and L is H, —COO—R3, —CO—R3, —CO—$N(R_3R_4)$, —$S(O)_2$—$R_3$, —$S(O)_2$—$N(R_3R_4)$, $N(R_3R4)$, $N(R4)C(O)R_3$, optionally substituted aryl, or optionally substituted heteroaryl;

$R_2$ is H, D, halogen, or optionally substituted alkyl;

each $R_3$ is independently selected from the group consisting of:

(i) H, aryl, substituted aryl, heteroaryl, or substituted heteroaryl;

(ii) heterocycloalkyl or substituted heterocycloalkyl;

(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and (iv) $NH_2$, $N=CR_4R_6$;

each $R_4$ is independently H, alkyl, alkyl, cycloalkyl, heterocycloalkyl, aryl, or heteroaryl, each of which is optionally substituted;

or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;

m is 0, 1, 2, or 3;

provided that (a) if ring A is thienyl, X is N, $R_2$ is H, RB is methyl, and Ri is —$(CH_2)_n$-L, in which n is 0 and L is —CO—$N(R_3R_4)$, then $R_3$ and $R_4$ are not taken together with the nitrogen atom to which they are attached to form a morpholino ring;

(b) if ring A is thienyl, X is N, $R_2$ is H, RB is methyl, and Ri is —$(CH_2)_n$-L, in which n is 0 and L is —CO—$N(R_3R_4)$, and one of $R_3$ and $R_4$ is H, then the other of $R_3$ and $R_4$ is not methyl, hydroxyethyl, alkoxy, phenyl, substituted phenyl, pyridyl or substituted pyridyl; and (c) if ring A is thienyl, X is N, $R_2$ is H, $R_B$ is methyl, and Ri is —$(CH_2)_n$-L, in which n is 0 and L is —COO—$R_3$, then $R_3$ is not methyl or ethyl; or a salt, solvate or hydrate thereof.

In certain embodiments, Ri is —$(CH_2)_n$-L, in which n is 0-3 and L is —COO—$R_3$, optionally substituted aryl, or optionally substituted heteroaryl; and $R_3$ is —$C_1$-$C_8$ alkyl, which contains 0, 1, 2, or 3 heteroatoms selected from O, S, or N, and which may be optionally substituted. In certain embodiments, n is 1 or 2 and L is alkyl or —COO—$R_3$, and $R_3$ is methyl, ethyl, propyl, i-propyl, butyl, sec-butyl, or t-butyl; or n is 1 or 2 and L is H or optionally substituted phenyl.

In certain embodiments, $R_2$ is H or methyl.

In certain embodiments, $R_B$ is methyl, ethyl, hydroxymethyl, methoxymethyl, trifluoromethyl, COOH, COOMe, COOEt, $COOCH_2OC(O)CH_3$.

In certain embodiments, ring A is phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, each $R_A$ is independently an optionally substituted alkyl, or any two $R_A$ together with the atoms to which each is attached, can form an aryl.

The invention also provides compounds of Formulae V-XXII, and any compound described herein.

In some embodiments, a bromodomain or BET inhibitor is:

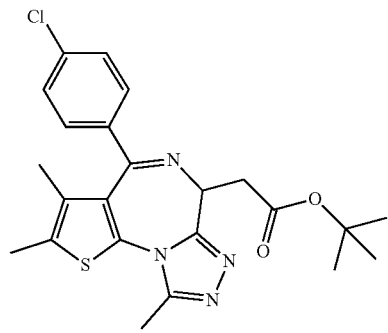 [SMILES: Cc1sc2c(c1C)C(c1ccc(Cl)cc1)=NC(CC(=O)OC(C)(C)C)c1nnc(C)n1-2]

a salt, solvate or hydrate thereof.

In certain embodiments, the compound is (+)-JQ1:

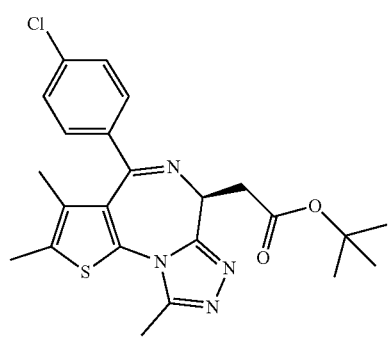 [SMILES: Cc1sc2c(c1C)C(c1ccc(Cl)cc1)=N[C@@H](CC(=O)OC(C)(C)C)c1nnc(C)n1-2]

or a salt, solvate or hydrate thereof.

In some embodiments, a bromodomain or BET inhibitor is a compound represented by the formula:
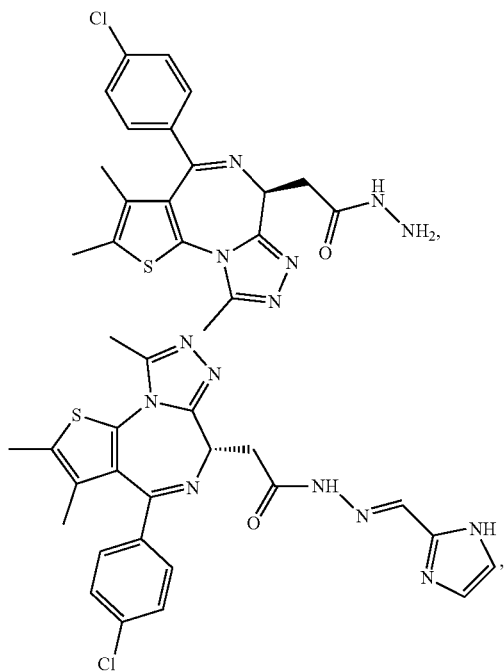
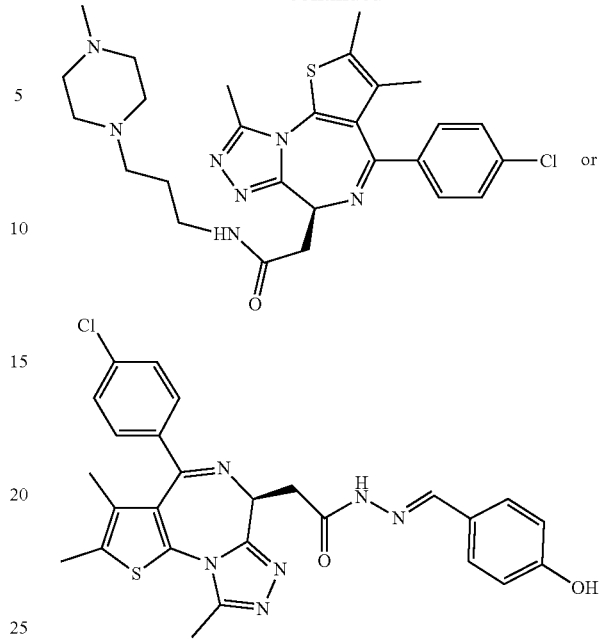
a salt, solvate or hydrate thereof.
In some embodiments, a bromodomain or BET inhibitor is a compound represented by the formula:
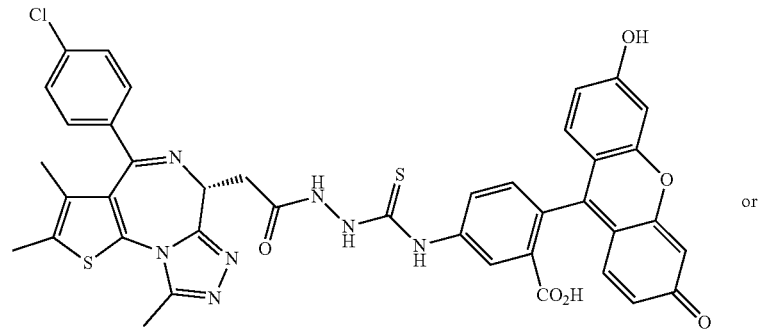
or
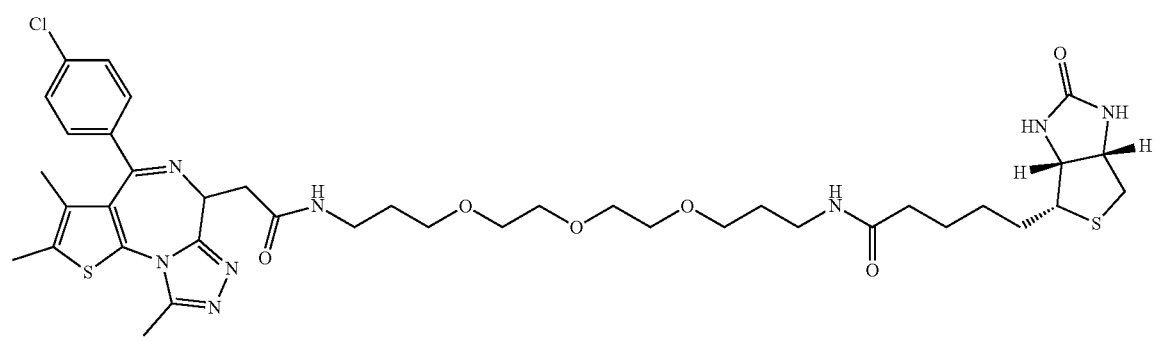
a salt, solvate or hydrate thereof.

In some embodiments, a bromodomain or BET inhibitor is a compound represented by any following formulae:
JQ1S
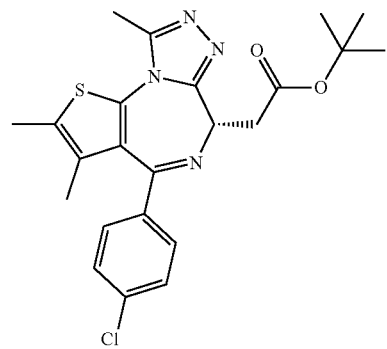
JQ6
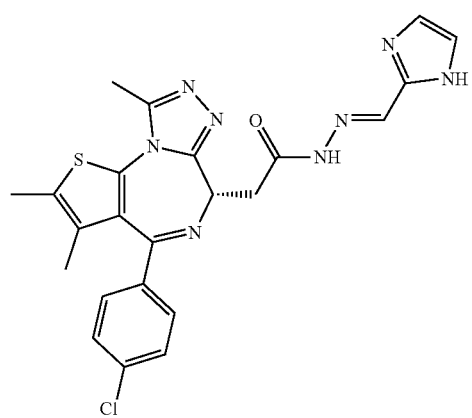
JQ11
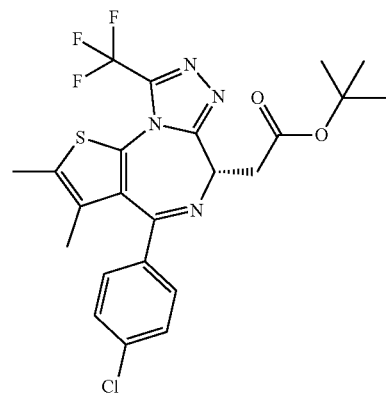
JQ1R
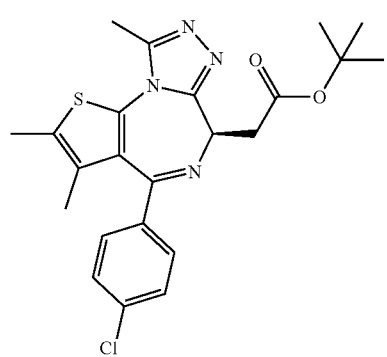
-continued
JQ13
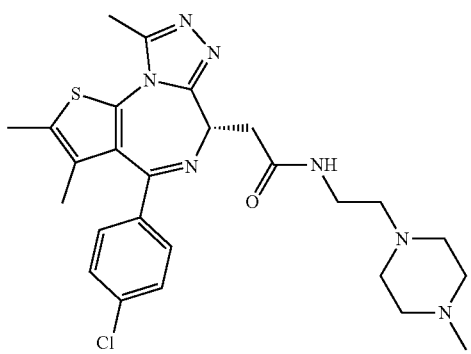
JQ21
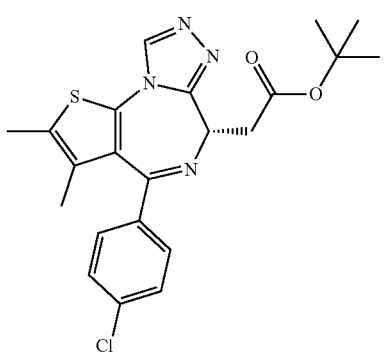
JQ20
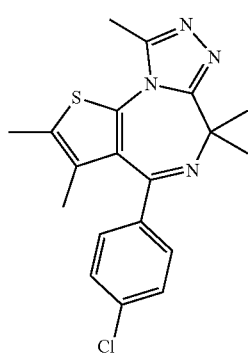
JQ19
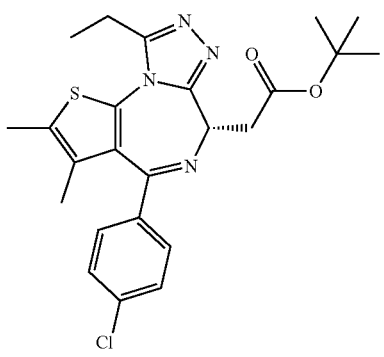

-continued
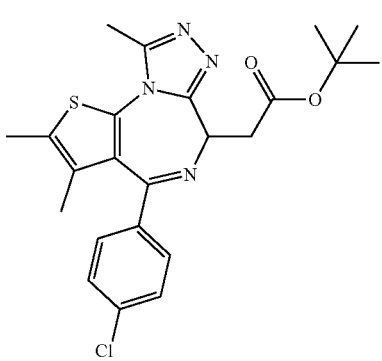
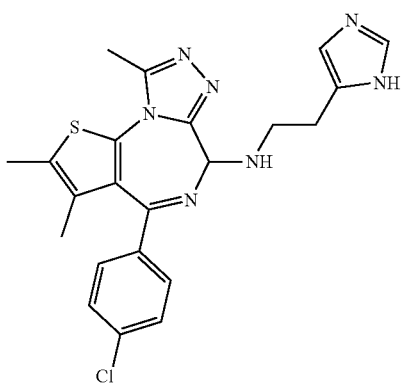
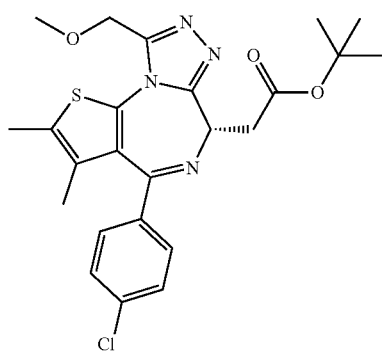
JQ18
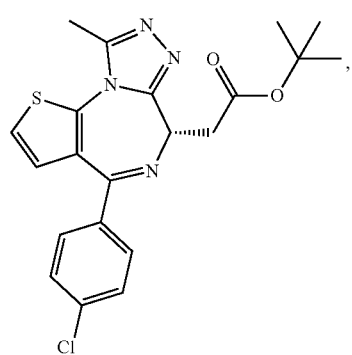
or a salt, solvate or hydrate thereof. In some embodiments, a bromodomain or BET inhibitor is a compound represented by any one of the following formulae:
JQ24B
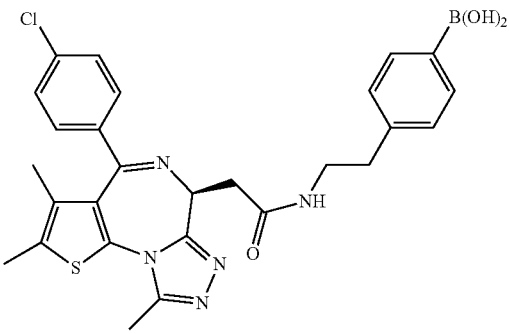
JQ8
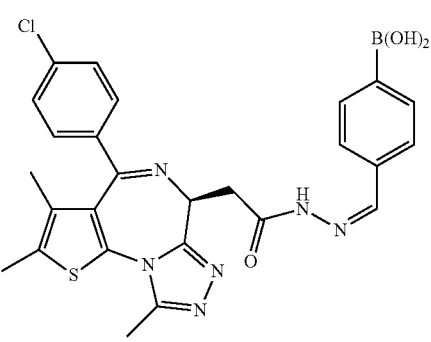
a salt, solvate or hydrate thereof. In some embodiments, a bromodomain or BET inhibitor is a compound represented by any following structures:
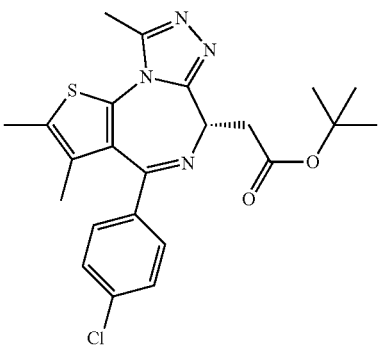
KS1
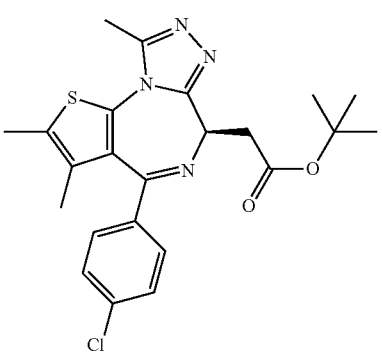

33
-continued
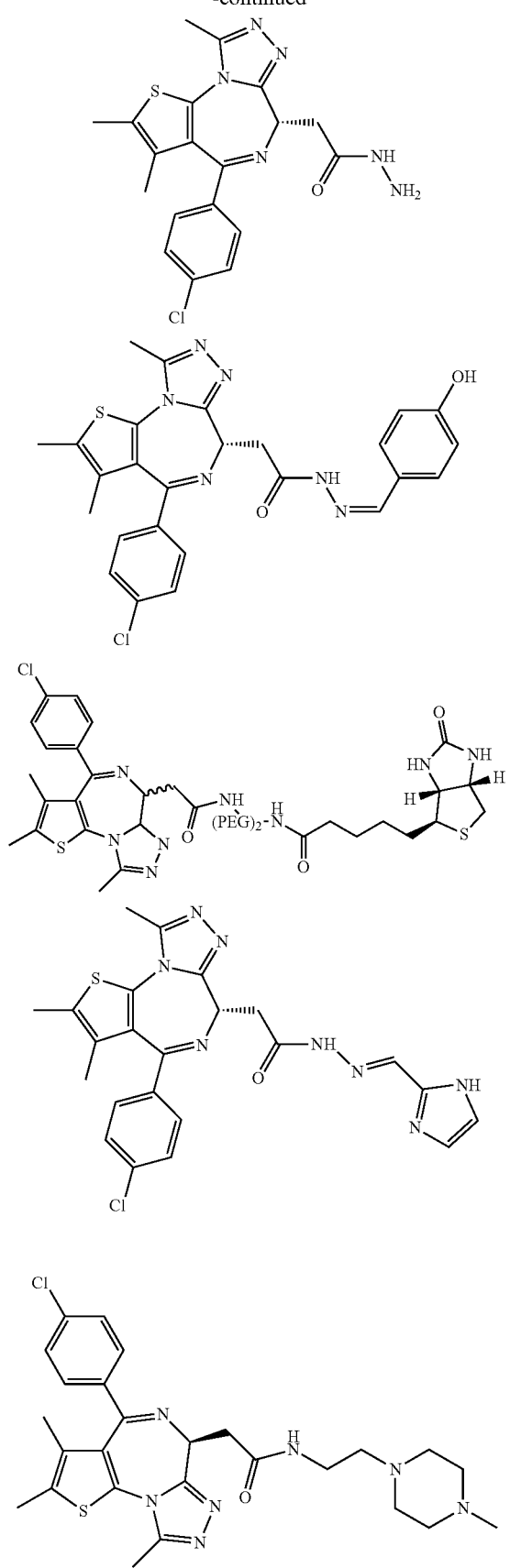
34
-continued
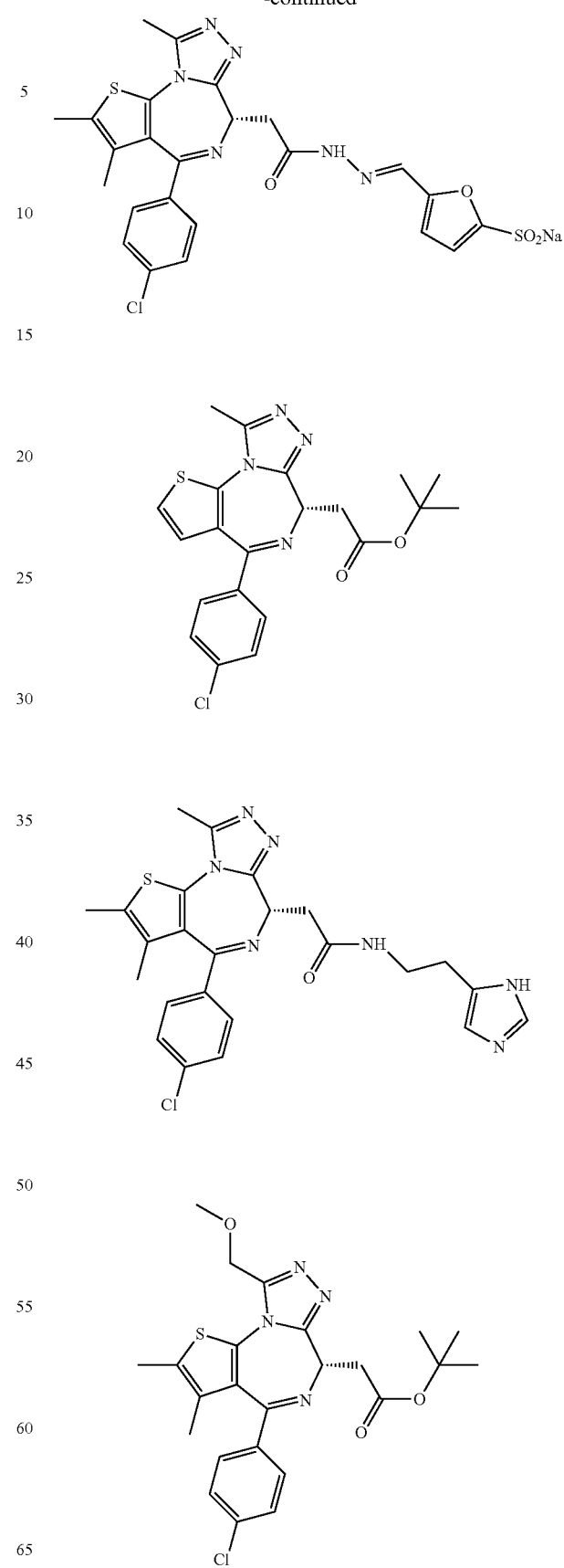

35
-continued
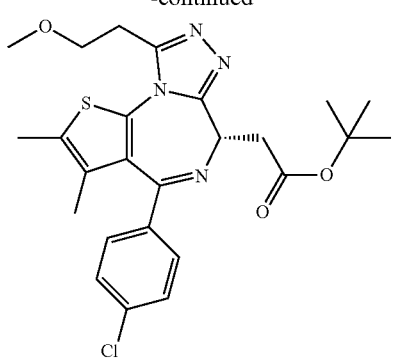
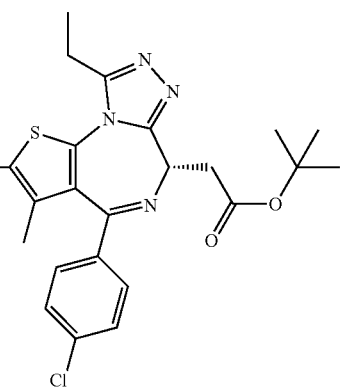
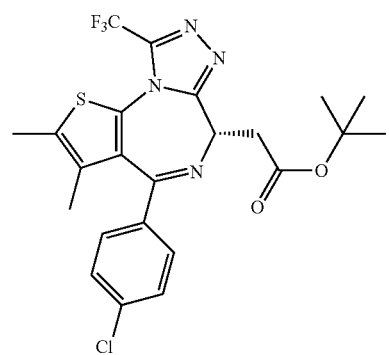
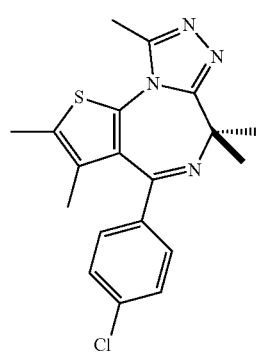
36
-continued
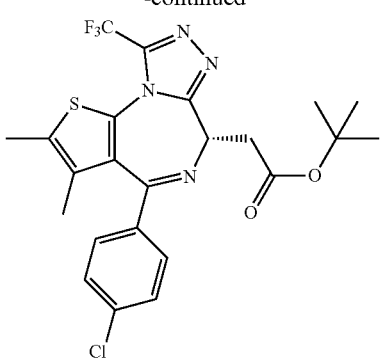
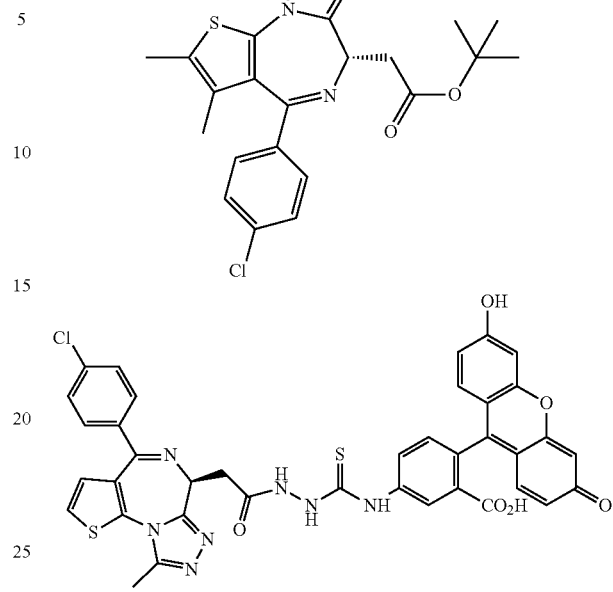
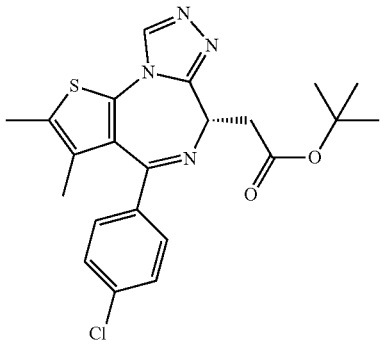
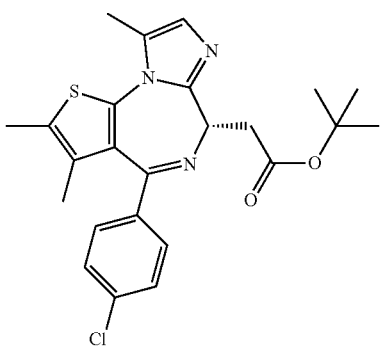
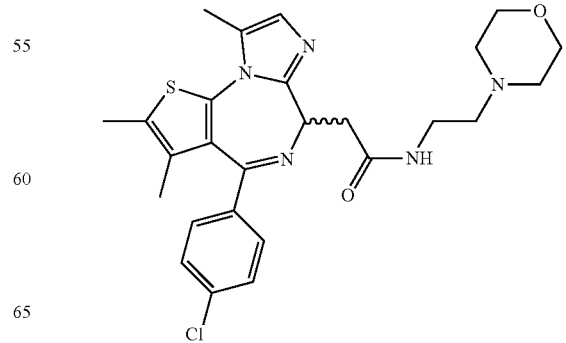

37
-continued
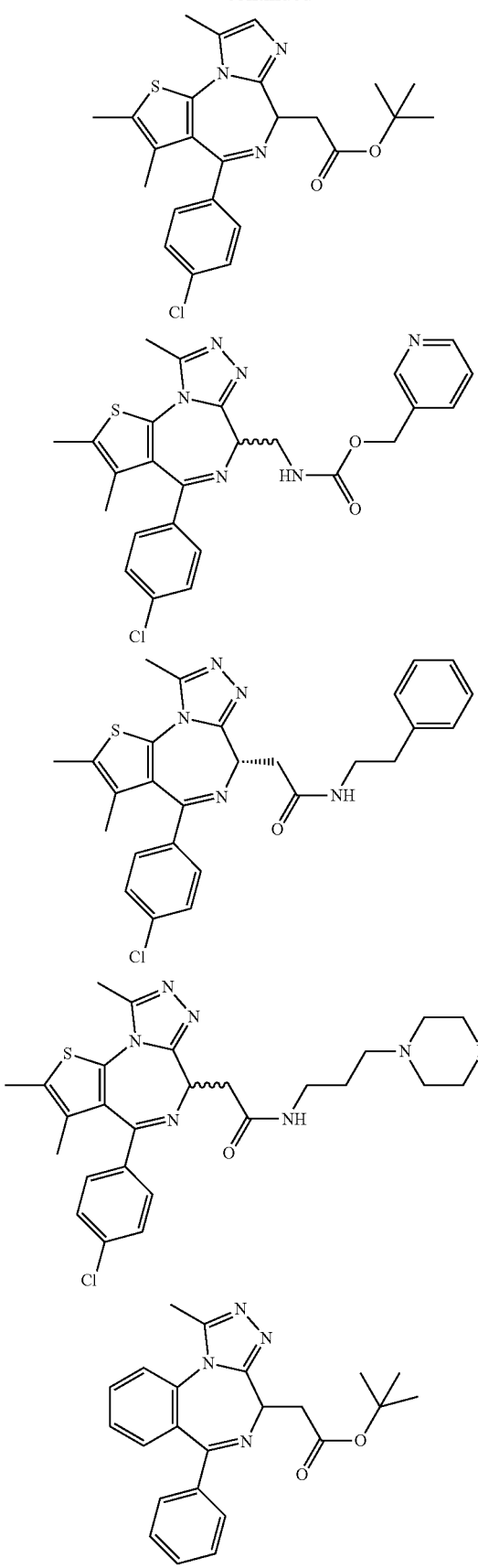
38
-continued
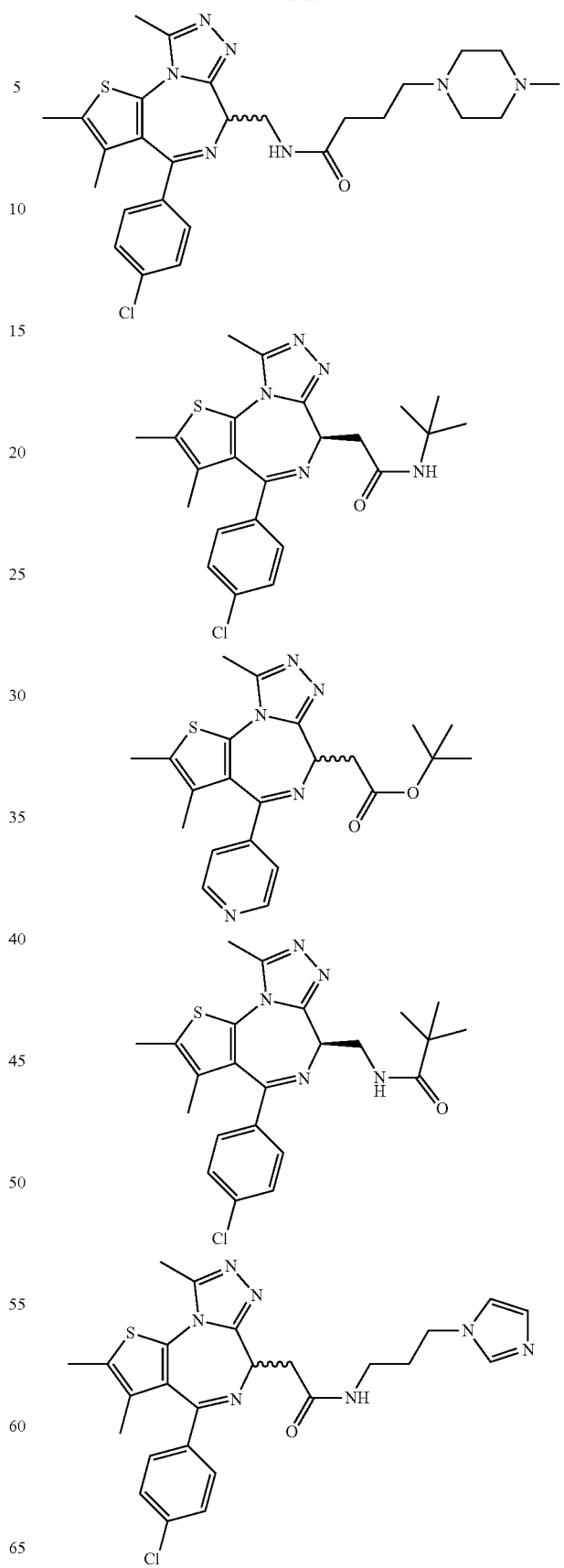

39
-continued
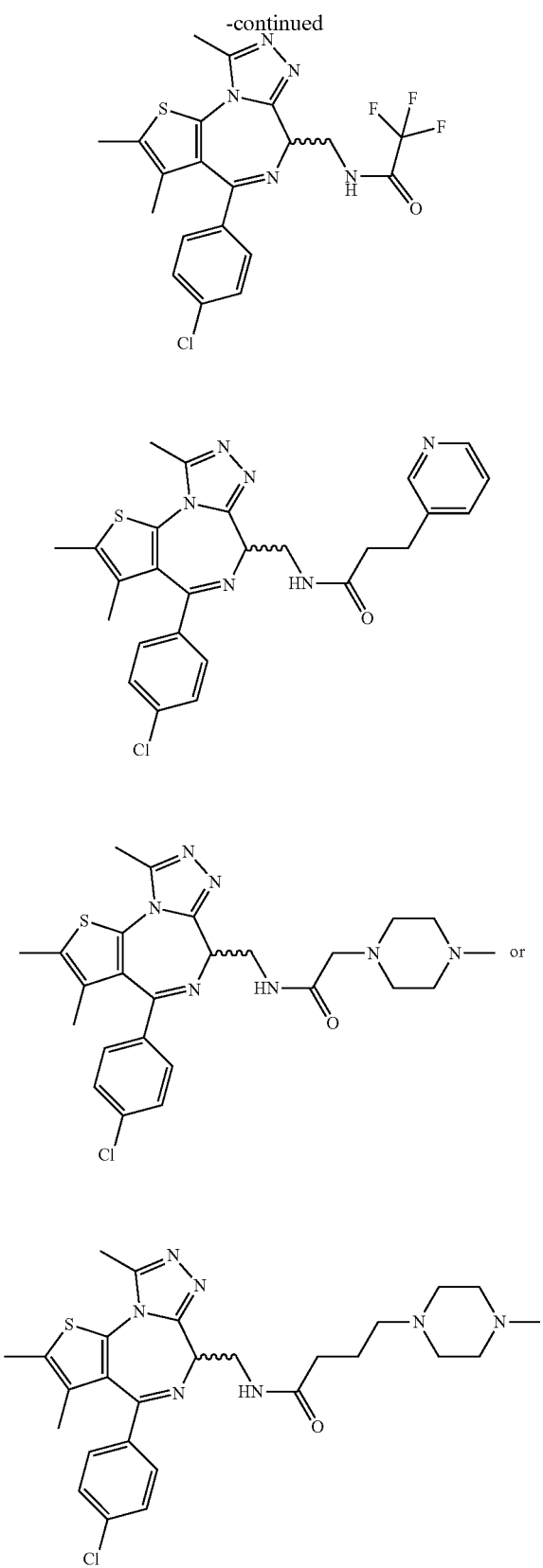
or a salt, solvate or hydrate thereof. In some embodiments, a bromodomain or BET inhibitor can be one of the following structures:
40
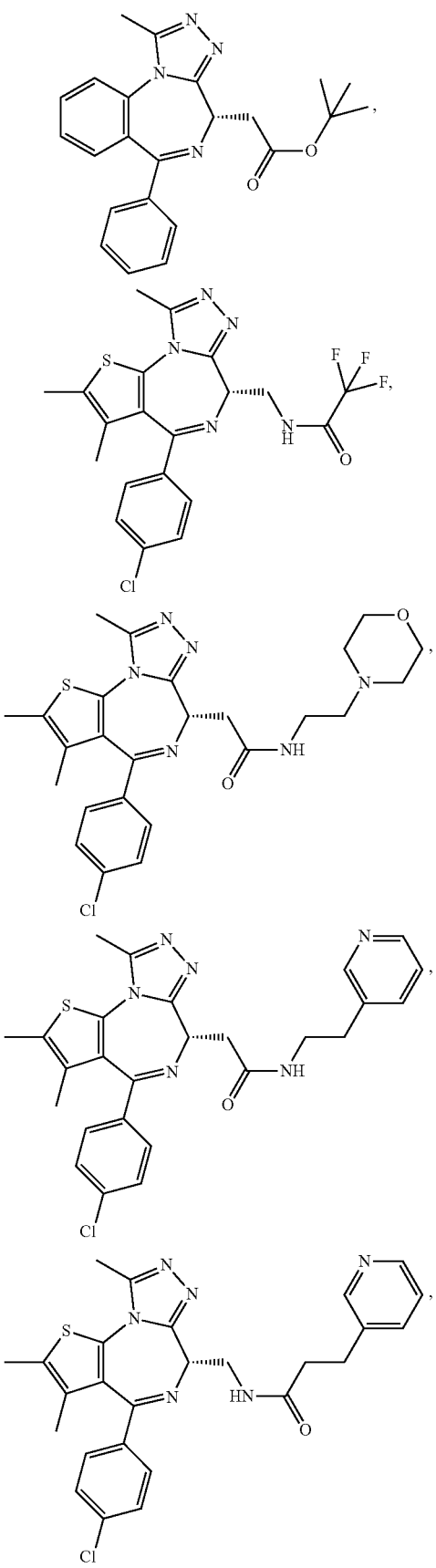

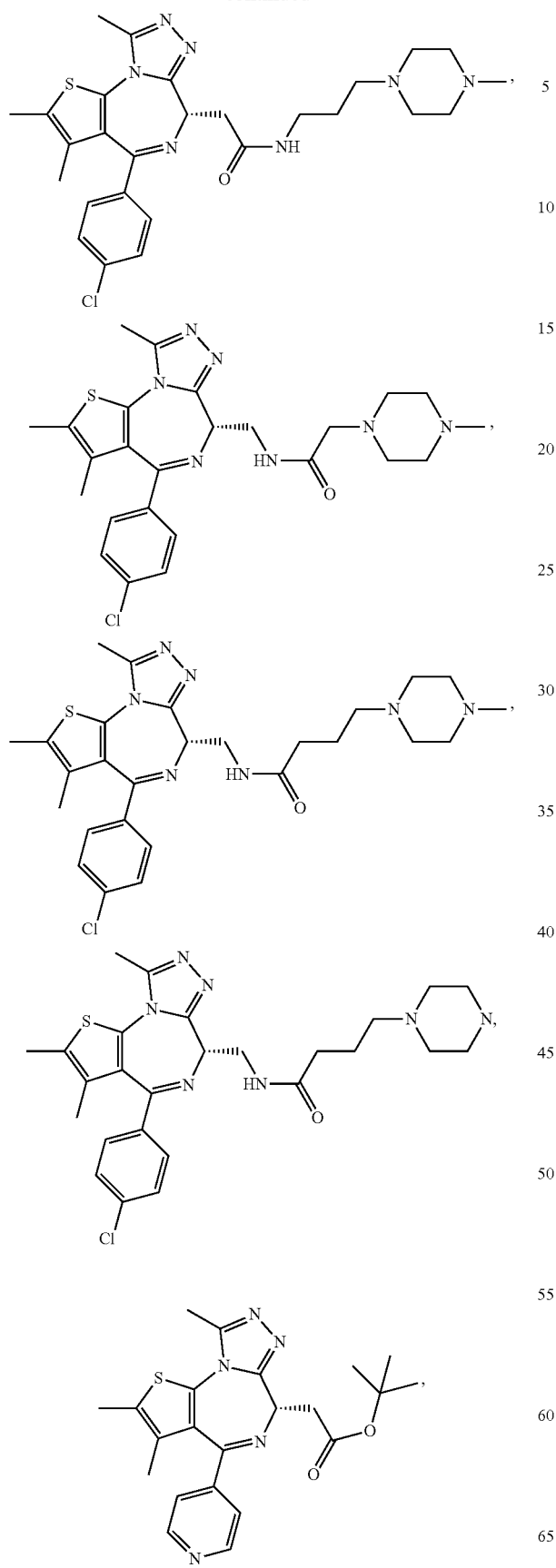
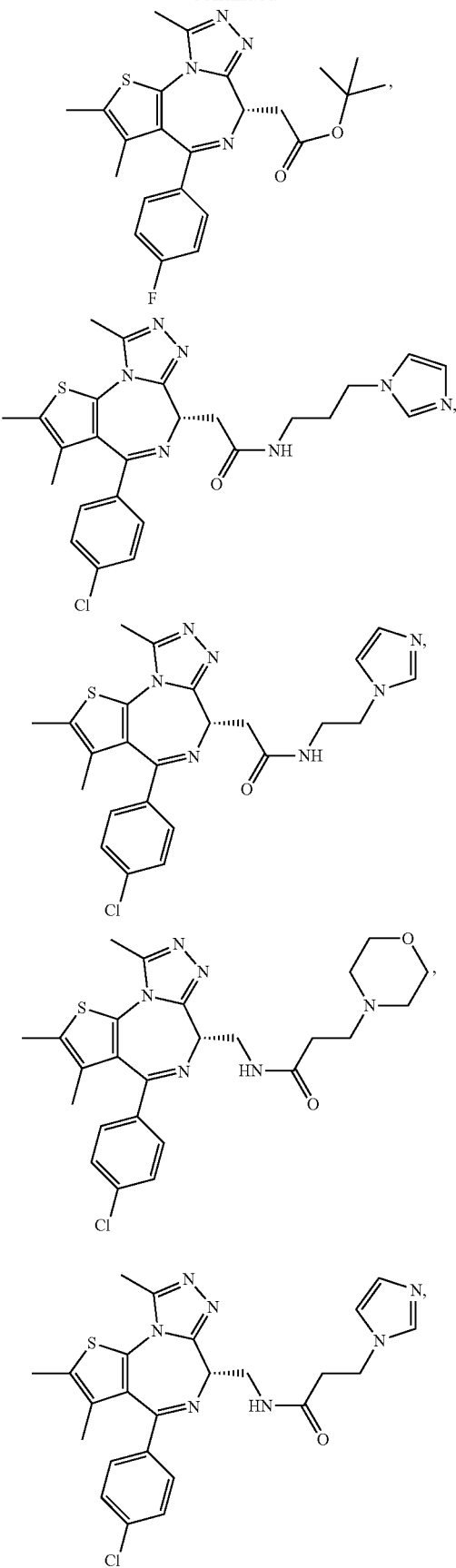

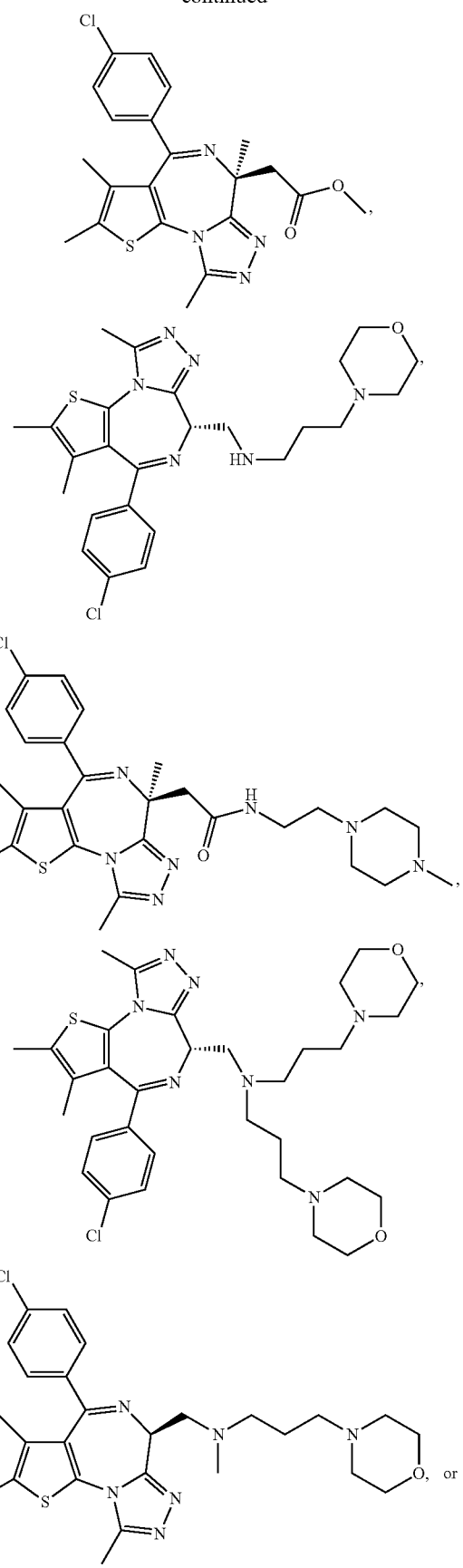

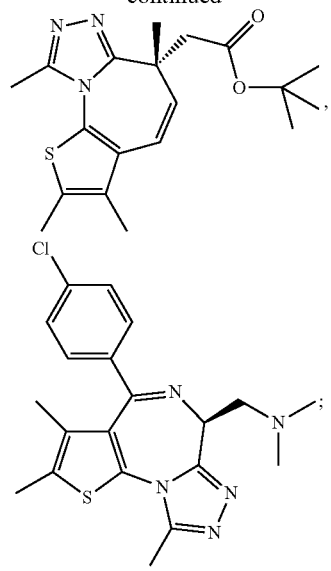

a salt, solvate or hydrate thereof.

In some embodiments, a bromodomain or BET inhibitor is a compound represented by the following structure:

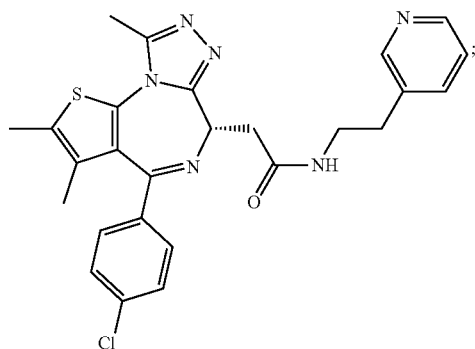 [SMILES: Cc1sc2c(c1C)C(c1ccc(Cl)cc1)=N[C@@H](CC(=O)NCCc1cccnc1)c1nnc(C)n1-2]

or a salt, solvate or hydrate thereof. In some embodiments, a bromodomain or BET inhibitor is a compound represented by the following structure:

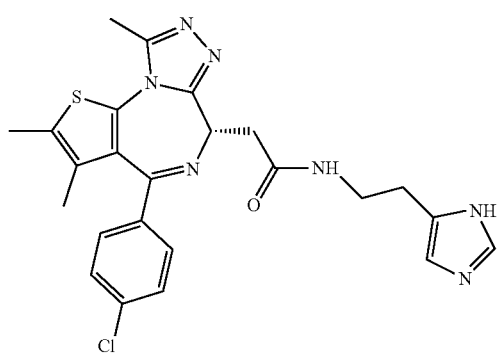 [SMILES: Cc1sc2c(c1C)C(c1ccc(Cl)cc1)=N[C@@H](CC(=O)NCCc1cnc[nH]1)c1nnc(C)n1-2]

or a salt, solvate or hydrate thereof. In some embodiments, a bromodomain or BET inhibitor is a compound represented by the following structure:

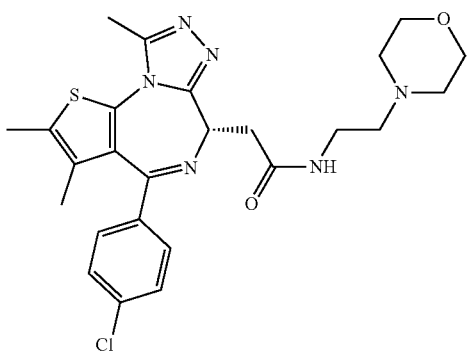 [SMILES: Cc1sc2c(c1C)C(c1ccc(Cl)cc1)=N[C@@H](CC(=O)NCCN1CCOCC1)c1nnc(C)n1-2]

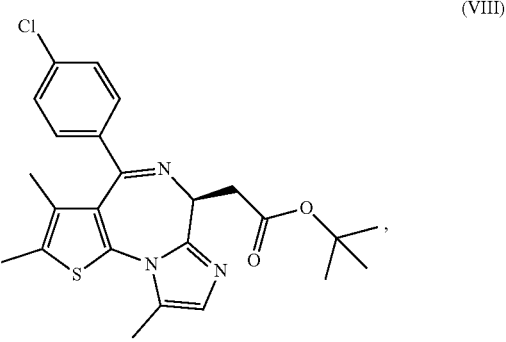 [SMILES: Cc1sc2c(c1C)C(c1ccc(Cl)cc1)=N[C@@H](CC(=O)OC(C)(C)C)c1ncc(C)n1-2]

or a salt, solvate or hydrate thereof. In some embodiments, a bromodomain or BET inhibitor is a compound with the opposite chirality of any compound shown herein. In some embodiments, a bromodomain or BET inhibitor is a compound represented by Formula (V), (VI), or (VII):

or a salt, solvate, or hydrate thereof. In some embodiments, a bromodomain or BET inhibitor is (racemic) JQ1; in certain embodiments, the compound is (+)-JQ1. In some embodiments, a bromodomain or BET inhibitor is a compound selected from the group consisting of:

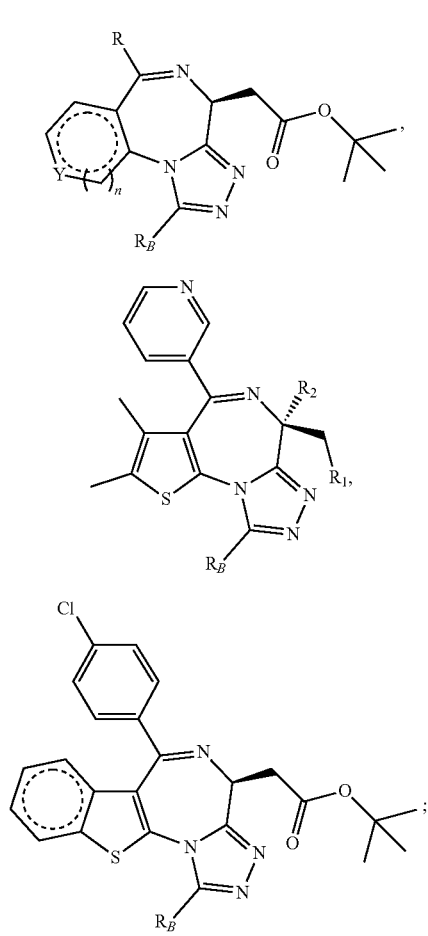

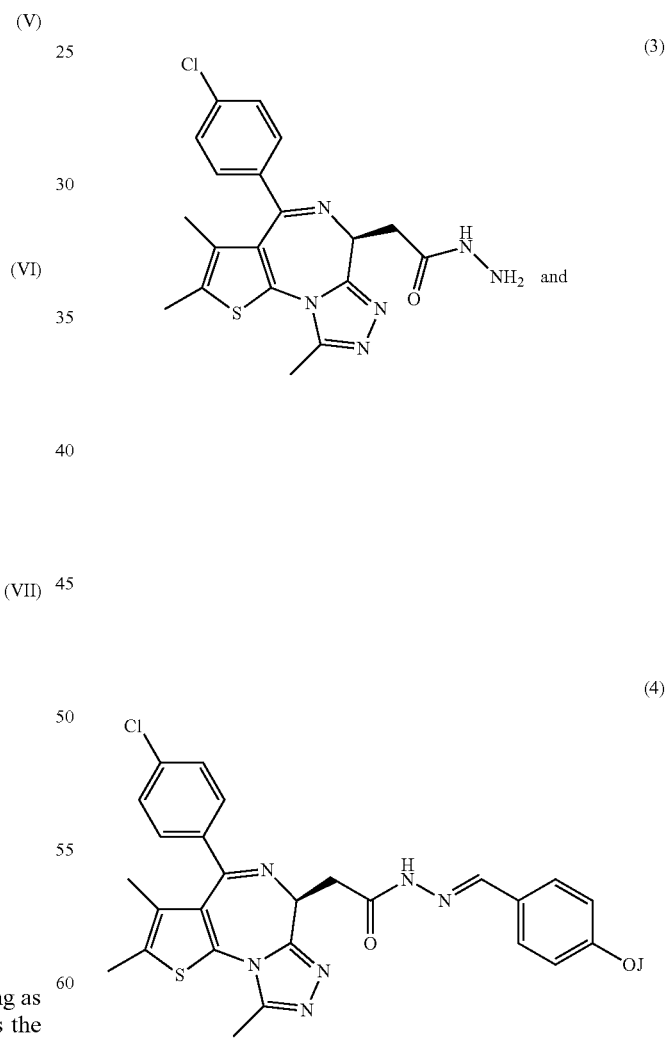

in which R, Ri, and $R_2$ and RB have the same meaning as in Formula (I); Y is O, N, S, or $CR_5$, in which R5 has the same meaning as in Formula (I); n is 0 or 1; and the dashed circle in Formula (VII) indicates an aromatic or non-aromatic ring; or a salt, solvate or hydrate thereof.

In some embodiments, a bromodomain or BET inhibitor is a compound represented by the formula:

or a salt, solvate, or hydrate thereof.

Additional examples of compounds include compounds according to any of the following formulae:

(IX)
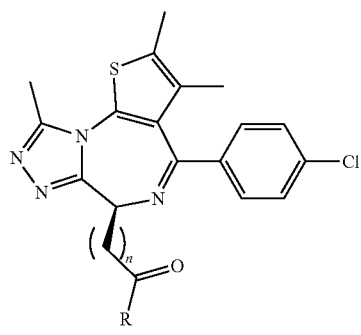
n = 1, 2, 3
(X)
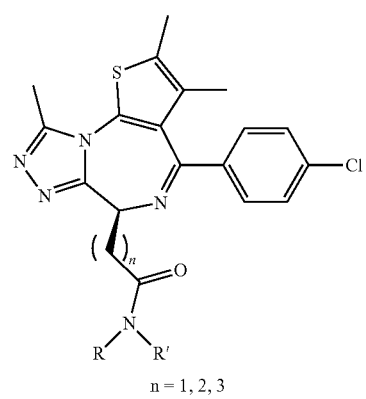
n = 1, 2, 3
(XI)
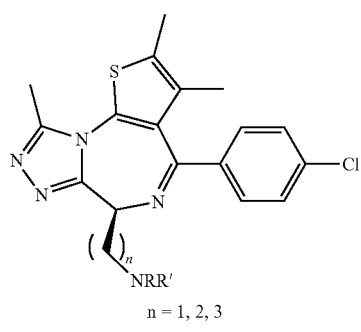
n = 1, 2, 3
(XII)
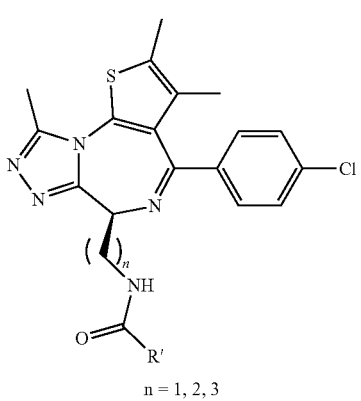
n = 1, 2, 3
(XIII)
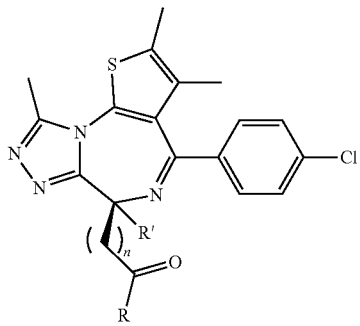
n = 1, 2, 3
R' = H, D, Me
(XIV)
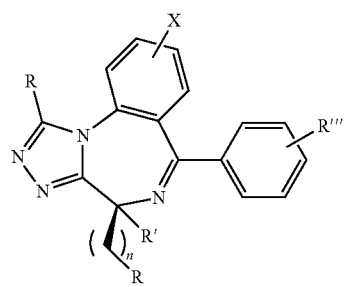
R' = H, D, Me
n = 1, 2, 3
(XV)
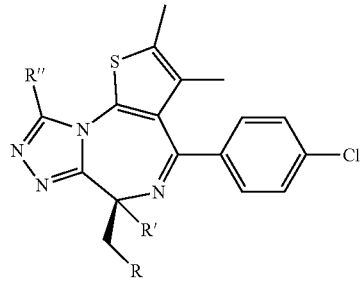
R' = OMe, CH₂OH, CH₂NH₂, CH₂OMe
(XVI)
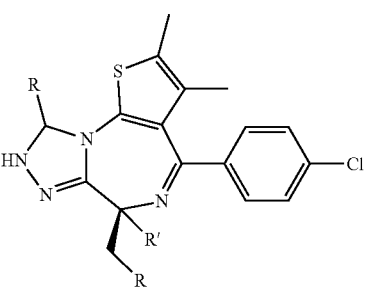

(XVII)
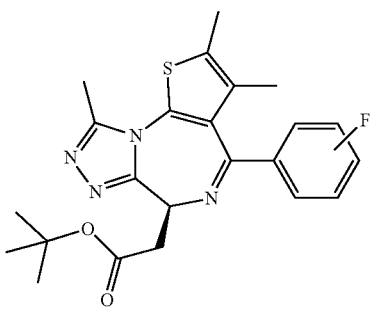

(XVIII)
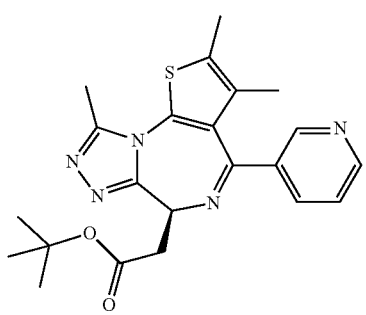

(XIX)
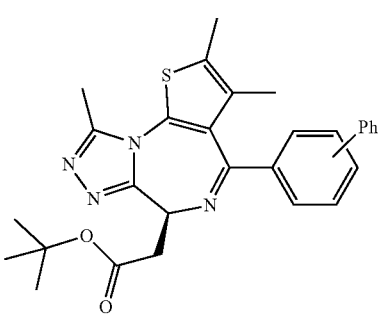

(XX)
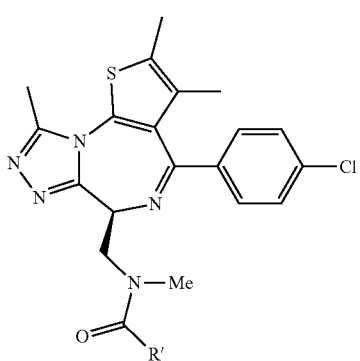

(XXI)
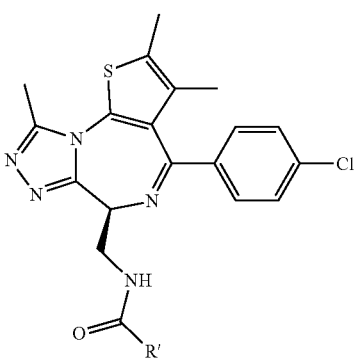

(XXII)
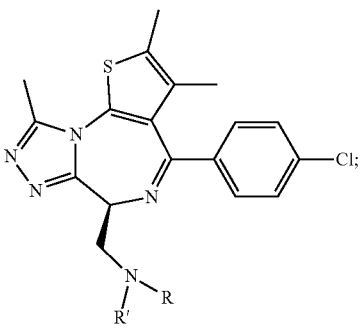

or a salt, solvate or hydrate thereof.

In Formulae IX-XXII, R and R' can be, e.g., H, aryl, substituted aryl, heteroaryl, heteroaryl, heterocycloalkyl, —$C_1$-$C_8$ alkyl, —$C_2$-$C_8$ alkenyl, —$C_2$-$C_8$ alkynyl, —$C_3$-$Ci_2$ cycloalkyl, substituted —$C_3$—$Ci_2$ cycloalkyl, —$C_3$-$Ci_2$ cycloalkenyl, or substituted —$C_3$-$Ci_2$ cycloalkenyl, each of which may be optionally substituted. In Formulae XIV, X can be any substituent for an aryl group as described herein.

The compounds described in herein can be prepared using methods well known in the prior art (see, e.g., WO 011143669, the entirety which is incorporated by reference herein).

As used herein, the term an "aromatic ring" or "aryl" means a monocyclic or polycyclic-aromatic ring or ring radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7, 8-tetrahydronaphthyl. An aryl group can be unsubstituted or optionally is substituted with one or more substituents, e.g., substituents as described herein for alkyl groups (including without limitation alkyl (preferably, lower alkyl or alkyl substituted with one or more halo), hydroxy, alkoxy (preferably, lower alkoxy), alkylthio, cyano, halo, amino, boronic acid (—B(OH)2, and nitro). In certain embodiments, the aryl group is a monocyclic ring, wherein the ring comprises 6 carbon atoms.

As used herein, the term "alkyl" means a saturated straight chain or branched non-cyclic hydrocarbon typically having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be unsubstituted, or optionally substituted with one or more substituents, such as amino, alkylamino, arylamino, heteroarylamino, alkoxy, alkylthio, oxo, halo, acyl, nitro, hydroxyl, cyano, aryl, heteroaryl, alkylaryl, alkylheteroaryl, aryloxy, heteroaryloxy, arylthio, heteroarylthio, arylamino, heteroarylamino, carbocyclyl, carbocyclyloxy, carbocyclylthio, carbocyclylamino, heterocyclyl, heterocyclyloxy, heterocyclylamino, heterocyclylthio, and the like. Lower alkyls are typically preferred for the compounds of this invention.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "halogen" designates —F, —Cl, —Br or —I.

The term "haloalkyl" is intended to include alkyl groups as defined above that are mono-, di- or polysubstituted by halogen, e.g., fluoromethyl and trifluoromethyl.

The term "hydroxyl" means —OH.

The term "heteroatom" as used herein means an atom of any element other than carbon or hydrogen. Preferred heteroatoms are nitrogen, oxygen, sulfur and phosphorus.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon. Heteroaryl groups may be optionally substituted with one or more substituents as for aryl groups. Examples of heteroaryl groups include, but are not limited to, pyridyl, furanyl, benzodioxolyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, and indolyl.

The term "heterocyclic" as used herein, refers to organic compounds that contain at least at least one atom other than carbon (e.g., S, O, N) within a ring structure. The ring structure in these organic compounds can be either aromatic or non-aromatic. Some examples of heterocyclic moeities include, are not limited to, pyridine, pyrimidine, pyrrolidine, furan, tetrahydrofuran, tetrahydrothiophene, and dioxane.

The term "isomers" or "stereoisomers" refers to compounds which have identical chemical constitution, but differ with regard to the arrangement of the atoms or groups in space.

The term "isotopic derivatives" includes derivatives of compounds in which one or more atoms in the compounds are replaced with corresponding isotopes of the atoms. For example, an isotopic derivative of a compound containing a carbon atom (C 112") would be one in which the carbon atom of the compound is replaced with the C 13 isotope.

The term "optical isomers" as used herein includes molecules, also known as chiral molecules, that are exact non-superimposable mirror images of one another.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "sulfhydryl" or "thiol" means —SH.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

In some embodiments, the bromodomain inhibitor is any molecule or compound that reduces or prevents expression of BRD-containing proteins. Examples of such inhibitors include siRNA, shRNA, dsRNA, oligomimics, and proteases that target one or more BRD-containing protein.

Methods for producing inhibitors as described above are well known in the art (See e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); the series METHODS IN ENZYMOLOGY (Academic Press, Inc.): PCR 2: A PRACTICAL APPROACH (Current Edition) ANTIBODIES, A LABORATORY MANUAL and ANIMAL CELL CULTURE (R. I. Freshney, ed. (1987)). DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.).

Protein Phosphatase 2A (PP2A)

The human genome contains about 107 tyrosine protein phosphatases (Alonso A et al. (2004) Cell 117:699-711), but only a few Serine-Threonine (Ser/Thr) protein phosphatases. The Ser/Thr protein phosphatases are classified into three structurally distinct families: PPM, PPP and FCP/SCP. Protein phosphatase 2A (PP2A) belongs to the PPP family and is a major Ser/Thr phosphatase that may be involved in many essential aspects of cellular function and regulation (Janssens V & Goris J (2001) Biochem J 353:417-439; Virshup D (2000) Curr Opin Cell Biol 12:180-185; Lechward K et al. (2001) Acta Biochim Pol 48:921-933). By some estimates, PP2A may account for the majority of all Ser/Thr phosphatase activities in mammalian cells. PP2A plays a principal role in cell cycle regulation, cell growth control, development, regulation of multiple signal transduction pathways, cytoskeleton dynamics and cell mobility. The essential function of PP2A is reflected by the fact that the catalytic subunit of PP2A is among the most conserved enzymes across species (Cohen P et al. (1990) FEBS Lett 268:355-359).

PP2A activators are known in the art. A PP2A activator is any molecule or compound that has any detectable positive effect on PP2A expression or PP2A phosphatase activity. In some embodiments, the PP2A activator activates PP2A as described above at least 10%, at least 20%, at least 50%, at least 100%, at least 200%, at least 300%, at least 500% or more as compared to the activity of a control (e.g., activity in the absence of the activator). An activator of PP2A can be a small molecule, a nucleic acid, a protein, a peptide, an antibody or antibody fragments.

Examples of PP2A activators are described in US 2010/0267673, WO 2009/117769, WO 2013181488, which are incorporated herein by reference. In some embodiments, a PP2A activator is a phenothiazine compound, including but not limited to, chlorpromazine, mesoridazine, thioridazine, acetophenazine, fluphenazine, perphenazine, trifluoperazine and pharmaceutically acceptable salts and esters thereof (see WO 2008/119109, incorporated by reference herein). In some embodiments, the PP2A activator is FTY720 ((2-Amino-2-[2-(4-octylphenyl) ethyl] propane 1, 3-diol hydrochloride; Fingolimod/Gilenya™; see WO 2007/143081 incorporated herein by reference).

In some embodiments, the BET inhibitor and the PP2A activator are synergistic in treating the cancer, compared to the BET inhibitor alone or the PP2A activator alone. In some embodiments, the BET inhibitor and the PP2A activator are administered along with a B-cell lymphoma-2 (Bcl-2) inhibitor, a B-cell lymphoma-extra large (Bcl-xl) inhibitor, a casein kinase 2 (CK2) inhibitor and/or a mediator complex subunit 1 (MED1) inhibitor described herein.

B-Cell Lymphoma-2 (Bcl-2) Inhibitor

Bcl-2 proteins function as critical regulators of apoptosis in both cancer and normal cells. Bcl-2 proteins serve as a check on apoptosis allowing healthy and useful cells to survive. This protein family includes anti-apoptotic proteins, such as Bcl-2, Bcl-xL, and Mcl-1, and pro-apoptotic molecules, including Bid, Bim, Bad, Bak and Bax. Bcl-2 and Bcl-xL proteins inhibit apoptosis by heterodimerization with pro-apoptotic Bcl-2 family proteins, such as Bak, Bax, Bim, Bid, Puma, and Bad.

As used herein, a "Bcl-xl inhibitor" refers to any molecule or compound that can prevent or inhibit, in part or in whole, the pro-survival function of Bcl-xl. The Bcl-xl inhibitor may be any molecule or compound, including nucleic acids such as DNA and RNA aptamers, antisense oligonucleotides, siRNA and shRNA, small peptides, antibodies or antibody fragments, and small molecules such as small chemical compounds. It is to be understood that the Bcl-xl inhibitor may inhibit only Bcl-xl or it may inhibit more than one or all Bcl-2 anti-apoptotic proteins.

As used herein, a "Bcl-2 inhibitor" refers to any molecule or compound that can prevent or inhibit, in part or in whole, the pro-survival function of Bcl-2. The Bcl-2 inhibitor may be any molecule or compound, including nucleic acids such as DNA and RNA aptamers, antisense oligonucleotides, siRNA and shRNA, small peptides, antibodies or antibody fragments, and small molecules such as small chemical compounds. It is to be understood that the Bcl-2 inhibitor may inhibit only Bcl-2 or it may inhibit more than one or all Bcl-2 anti-apoptotic proteins. In some embodiments, a Bcl-2 inhibitor inhibits Bcl-xl.

Bcl-xl and Bcl-2 inhibitors are known in the art. Examples of Bcl-xl and Bcl-2 inhibitors are described in WO 2012/103059, U.S. Pat. Nos. 8,309,582, 8,557,812, 8,865,901, WO 2012071374, and Cang et al. (J Hematol Oncol 2015 8:129), which are incorporated by reference herein. The methods described herein are useful with any known or hereafter developed Bcl-xl inhibitor.

In some embodiments, the Bcl-xl inhibitors include, but are not limited to: ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl] sulfonylbenzamide; Santa Cruz Biotechnology), ABT-263 (4-[4-[[2-(4-chlorophenyl)-5,5-dimethylcyclohexen-1-yl]methyl] piperazin-1-yl]-N-[4-[[(2R)-4-morpholin-4-yl-1-phenylsulfanylbutan-2-yl]amino]-3-(trifluoromethylsulfonyl)phenyl]sulfonylbenzamide; Navitoclax—APeXBIO), AT 101 ((−)-1,1',6,6',7,7'-Hexahydroxy-3,3'-dimethyl-5,5'-bis(1-methylethyl)-[2,2'-binaphthalene]-8,8'-dicarboxaldehyde), Sabutoclax (2,3,5-trihydroxy-7-methyl-N-[(2R)-2-phenylpropyl]-6-[1,6,7-trihydroxy-3-methyl-5-[[(2R)-2-phenylpropyl]carbamoyl] naphthalen-2-yl]naphthalene-1-carboxamide; TOCRIS) and TW 37 (N-[4-[[2-(1,1-Dimethylethyl)phenyl]sulfonyl]phenyl]-2,3,4-trihydroxy-5-[[2-(1-methylethyl)phenyl]methyl] benzamide; TOCRIS). In some embodiments, the Bcl-2 inhibitors include, but are not limited to ABT-199 (4-[4-[[2-(4-chlorophenyl)-4,4-dimethylcyclohexen-1-yl]methyl]piperazin-1-yl]-N-[3-nitro-4-(oxan-4-ylmethylamino)phenyl] sulfonyl-2-(1H-pyrrolo[2,3-b]pyridin-5-yloxy)benzamide).

In some embodiments, the BET inhibitor and the Bcl-xl inhibitor are synergistic in treating the cancer, compared to the BET inhibitor alone or the Bcl-xl inhibitor alone. In some embodiments, the BET inhibitor and the Bcl-xl inhibitor are administered to the subject along with a protein phosphatase 2A (PP2A) activator, a casein kinase 2 (CK2) inhibitor and/or a mediator complex subunit 1 (MED1) inhibitor described herein.

In some embodiments, the BET inhibitor and the Bcl-2 inhibitor are synergistic in treating the cancer, compared to the BET inhibitor alone or the Bcl-2 inhibitor alone. In some embodiments, the BET inhibitor and the Bcl-2 inhibitor are administered to the subject along with a Bcl-xl, protein phosphatase 2A (PP2A) activator, a casein kinase 2 (CK2) inhibitor and/or a mediator complex subunit 1 (MED1) inhibitor described herein.

Casein Kinase 2 (CK2) Inhibitor

Casein protein kinase 2 (CK2) is a ubiquitous protein serine/threonine kinase that has been implicated in multiple functions in the cell including the regulation of cell growth and proliferation as well as apoptosis (see, for example, Tawfic et al., 2001, Histol. HistopathoL, 16:573-82). CK2 is a highly conserved enzyme, and has been suggested to be essential for cell survival. The kinase is a heterotetramer consisting of two catalytic subunits ($\alpha$ and/or $\alpha'$) complexed with two p subunits. One means by which CK2 regulates cell growth is through signaling in the nucleus where nuclear matrix and chromatin appear to be its preferential targets. The CK2 inhibitor may be any molecule or compound, including nucleic acids such as DNA and RNA aptamers, antisense oligonucleotides, siRNA and shRNA, small peptides, antibodies or antibody fragments, and small molecules such as small chemical compounds.

CK2 inhibitors are known in the art. Examples of CK2 inhibitors are described in US 2011/0207789, U.S. Pat. No. 6,607,916, US 2010/0256217, and WO 2006.065724, which are incorporated by reference herein. The methods described herein are useful with any known or hereafter developed CK2 inhibitor.

In some embodiments, the CK2 inhibitors include, but are not limited to: CX-4945 (5-(3-chloroanilino)benzo[c][2,6] naphthyridine-8-carboxylic acid; Silmitasertib; APeXBIO), DMAT (MCE MedChem Express), ellagic acid (MCE MedChem Express), TTP22 (MCE MedChem Express).

The chemical structure of DMAT is:

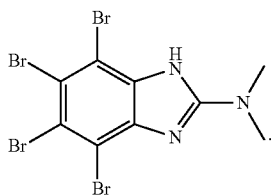 [SMILES: CN(C)c1nc2c(Br)c(Br)c(Br)c(Br)c2[nH]1]

The chemical structure of ellaic acid is:

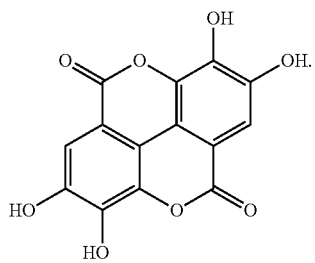

The chemical structure of TTP22 is:

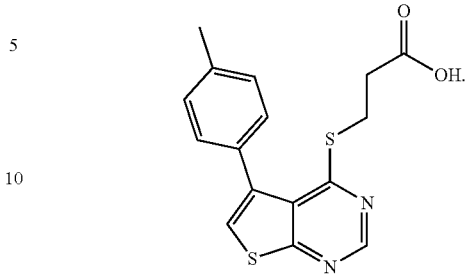

In some embodiments, the BET inhibitor and the CK2 inhibitor are synergistic in treating the cancer, compared to the BET inhibitor alone or the CK2 inhibitor alone. In some embodiments, the BET inhibitor and the CK2 inhibitor are administered to the subject along with a protein phosphatase 2A (PP2A) activator, a B-cell lymphoma-2 (Bcl-2) inhibitor, a B-cell lymphoma-extra large (Bcl-xl) inhibitor and/or a mediator complex subunit 1 (MED1) inhibitor described herein.

Mediator Complex Subunit 1 (MED1) Inhibitor

The activation of gene transcription is a multistep process that is triggered by factors that recognize transcriptional enhancer sites in DNA. These factors work with co-activators to direct transcriptional initiation by the RNA polymerase II apparatus. The mediator of RNA polymerase II transcription subunit 1 (MED1) protein is a subunit of the CRSP (cofactor required for SP1 activation) complex, which, along with TFIID, is required for efficient activation by SP1. This protein is also a component of other multisubunit complexes (e.g., thyroid hormone receptor-(TR-) associated proteins that interact with TR and facilitate TR function on DNA templates in conjunction with initiation factors and cofactors). It also regulates p53-dependent apoptosis and it is essential for adipogenesis. This protein is known to have the ability to self-oligomerize.

The CK2 inhibitor may be any molecule or compound, including nucleic acids such as DNA and RNA aptamers, antisense oligonucleotides, siRNA and shRNA, small peptides, antibodies or antibody fragments, and small molecules such as small chemical compounds. In some embodiments, the MED1 inhibitor disrupts interaction between MED1 and BRD4.

In some embodiments, the BET inhibitor and the MED1 inhibitor are synergistic in treating the cancer, compared to the BET inhibitor alone or the MED1 inhibitor alone. In some embodiments, the BET inhibitor and the MED1 inhibitor are administered to the subject along with a protein phosphatase 2A (PP2A) activator, a B-cell lymphoma-2 (Bcl-2) inhibitor, a B-cell lymphoma-extra large (Bcl-xl) inhibitor and/or a casein kinase 2 (CK2) inhibitor described herein.

Pharmaceutical Compositions

One aspect of the present disclosure relates to pharmaceutical compositions that comprise a BET inhibitor and a protein phosphatase 2A (PP2A) activator, a B-cell lymphoma-2 (Bcl-2) inhibitor a B-cell lymphoma-extra large (Bcl-xl) inhibitor, a casein kinase 2 (CK2) inhibitor and/or a mediator complex subunit 1 (MED1) inhibitor. The pharmaceutical compositions described herein may be useful in treating and/or preventing cancer in a subject in need thereof, such as cancers that are resistant to or are at risk of becoming resistant to a BET inhibitor. The pharmaceutical compositions described herein may also be useful in reducing, delaying, and/or preventing in a subject in need thereof the resistance of a cancer to treatment with a BET inhibitor.

Pharmaceutical compositions described herein can be prepared by any method known in the art of pharmacology. In general, such preparatory methods include the steps of bringing the active ingredients described herein, such as a BET inhibitor and/or a PP2A activator, into association with a carrier or excipient, and/or one or more other accessory ingredients, and then, if necessary and/or desirable, shaping, and/or packaging the product into a desired single- or multi-dose unit. Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The pharmaceutical preparations of the present invention may include or be diluted into a pharmaceutically-acceptable carrier. The term "pharmaceutically-acceptable carrier" as used herein means one or more compatible fillers, diluents or other such substances, which are suitable for administration to a human or other mammal such as a dog, cat, or horse. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral, subcutaneous, intravenous, intramuscular, etc. formulations can be found in Remington's Pharmaceutical Sciences, Mack Publishing Company, Easton, Pa.

Theranostic Methods

Some aspects of the present disclosure provides methods to identify a subject having a cancer that is resistant to or at risk of developing resistance to bromodomain and extra terminal (BET) inhibitor therapy. In some embodiments, the method comprises performing an assay to determine intracellular location of bromodomain-containing protein 4 (BRD4) in a tumor sample obtained from a subject receiving BET inhibitor therapy; and identifying the subject as having a cancer that is resistant to or at risk of developing resistance to BET inhibitor therapy if the BRD4 has a nuclear localization.

The methods described herein aid in establishing or indicating (i.e., identifying) whether a subject has a cancer that is resistant to or at risk of developing resistance to bromodomain and extra terminal (BET) inhibitor therapy. As used herein, "a cancer that is resistant to BET inhibitor therapy" means that the cancer does not respond to such an inhibitor, for example as evidenced by continued proliferation and increasing tumor growth and burden. In some embodiments, the cancer may have initially responded to treatment with such inhibitor (referred to herein as a previously administered therapy) but is likely to grow resistant after a time (i.e., the cancer is at risk of developing resistance to BET inhibitor therapy). In some embodiments, the cancer may have never responded to treatment with such inhibitor at all.

The subject is diagnosed by a physician (e.g., using methods well known in the art) as having cancer, and is being treated with BET inhibitor therapy.

The intracellular location of BRD4 in a tumor sample obtained from the subject can be determined using an assay known in the art. For example, the intracellular location of BRD4 may be determined by immunohistochemistry, immunofluorescence, immunoblotting, radioimmunoassay, ELISA or FACS analysis. In some embodiments, the intracellular location of BRD4 is determined using antibodies in conjunction with immunofluorescence.

The subject is identified as having a cancer that is resistant to or at risk of developing resistance to BET inhibitor therapy if the BRD4 has a nuclear localization. Alternatively, the subject is identified as having a cancer that is not resistant to BET inhibitor therapy if the BRD4 has a cytoplasmic localization. If the subject is identified as having a cancer that is resistant to or at risk of developing resistance to BET inhibitor therapy, then the subject may be treated by administering a BET inhibitor in combination with a protein phosphatase 2A (PP2A) activator, a B-cell lymphoma-2 (Bcl-2) inhibitor, a B-cell lymphoma-extra large (Bcl-xl) inhibitor, a casein kinase 2 (CK2) inhibitor, and/or a mediator complex subunit 1 (MED1). Thus, the methods described herein also aid in identifying subjects that are likely to benefit from treatment with combination therapy, instead of monotherapy with a BET inhibitor.

In some embodiments, the method comprises performing an assay to determine a ratio of phosphorylated bromodomain-containing protein 4 (pBRD4) to un-phosphorylated BRD4 (BRD4) in a tumor sample obtained from a subject having a cancer; and identifying the subject as having a cancer that is resistant to or at risk of developing resistance to BET inhibitor therapy if the ratio of pBRD4 to BRD4 is increased as compared to a control ratio of pBRD4 to BRD4.

The subject is diagnosed by a physician (e.g., using methods well known in the art) as having cancer. In some embodiments, the subject is being treated with BET inhibitor therapy. In some embodiments, the subject is not receiving but is being considered for treatment with BET inhibitors.

The ratio of phosphorylated bromodomain-containing protein 4 (pBRD4) to un-phosphorylated BRD4 (BRD4) in a tumor sample can be determined by immunoblotting, immunohistochemistry, immunofluorescence, radioimmunoassay, ELISA or FACS analysis. In some embodiments, multicolor immunofluorescence is used to determine the ratio of pBRD4 to BRD4. In some embodiments, the ratio of pBRD4 to BRD4 is determined by immunoblotting.

The subject is identified as having a cancer that is resistant to or at risk of developing resistance to BET inhibitor therapy if the ratio of pBRD4 to BRD4 is increased as compared to a control ratio of pBRD4 to BRD4. Alternatively, the subject is identified as having a cancer that is not resistant to BET inhibitor therapy if the ratio of pBRD4 to BRD4 is decreased or is unchanged as compared to a control ratio of pBRD4 to BRD4. A control ratio of pBRD4 to BRD4 can be determined or can be a pre-existing ratio. In some embodiments, the control ratio is the ratio of pBRD4 to BRD4 in a tumor sample obtained from a subject having a cancer that is not resistant to BRD4 inhibitor therapy. In some embodiments, the control ratio is the ratio of pBRD4 to BRD4 in a tissue sample obtained from a subject that does not have cancer.

The magnitude of difference between the subject's ratio of pBRD4 to BRD4 and the control ratio may vary. For example, the subject may be identified as having a cancer that is resistant to or at risk of developing resistance to BET inhibitor therapy if the ratio of pBRD4 to BRD4 is at least 1%, at least 5%, at least 10%, at least 25%, at least 50%, at least 100%, at least 250%, at least 500%, or at least 1000% higher than the control ratio. In some embodiments, the subject may be identified as having a cancer that is resistant to or at risk of developing resistance to BET inhibitor therapy if the ratio of pBRD4 to BRD4 is at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100-fold, or more higher than the control ratio. Significant differences may be identified by using an appropriate statistical test. Tests for statistical significance are well known in the art and are exemplified in Applied Statistics for Engineers and Scientists by Petruccelli, Chen and Nandram 1999 Reprint Ed.

If the subject is identified as having a cancer that is resistant to or at risk of developing resistance to BET inhibitor therapy, then the subject may be treated by administering a BET inhibitor in combination with a protein phosphatase 2A (PP2A) activator, a B-cell lymphoma-2 (Bcl-2) inhibitor, a B-cell lymphoma-extra large (Bcl-xl) inhibitor, a casein kinase 2 (CK2) inhibitor, and/or a mediator complex subunit 1 (MED1). Thus, the methods described herein also aid in identifying subjects that are likely to benefit from treatment with combination therapy, instead of monotherapy with a BET inhibitor.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLE

Sensitivity of Breast Cancer to BET Bromodomain Inhibition

Figure 1B:
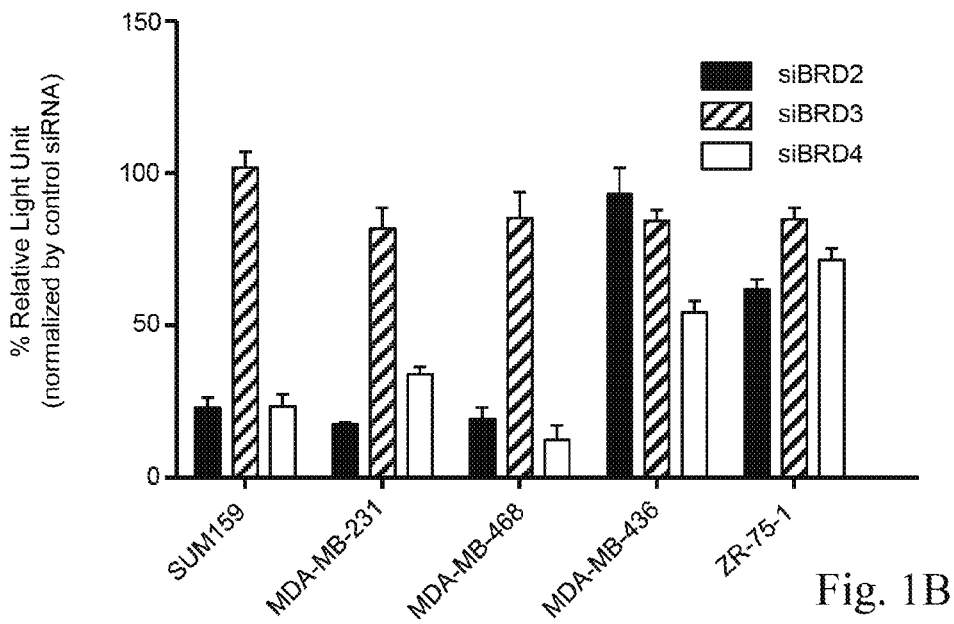
Figure 7A:
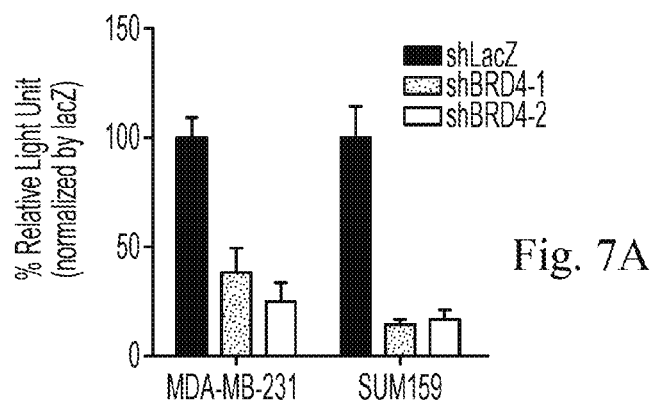
FIGS. 7A-7E. BET bromodomain proteins and cell growth in TNBCs.
Figure 7B:
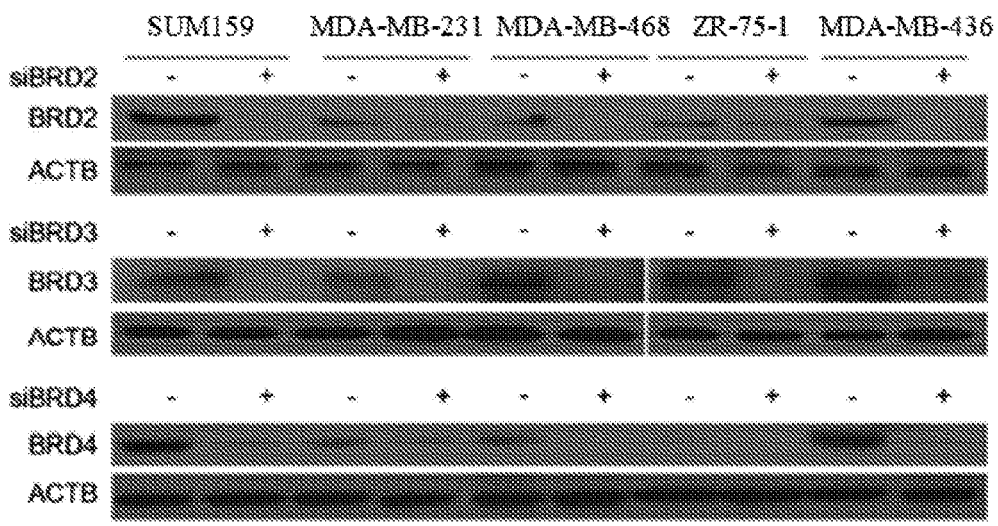

The effect of BBI was first evaluated in a panel of breast cancer cells reflecting transcriptionally-defined subtypes: luminal, HER2+, and TNBC (both basal and mesenchymal subsets)[3,22]. In addition to JQ1, samples of structurally divergent chemical probes (iBET151, PFI-1), investigational agents (iBET, GSK-762; Y803, OTX-015), and inactive analogues (alprazolam and the inactive JQ1 enantiomer, R-JQ1) were prepared. Proliferation of most TNBC cell lines was markedly inhibited in a potency-proportionate manner with IC50s in the low nM range, whereas luminal cell lines were relatively resistant (FIG. 1A). The dependency of TNBC cells on BET bromodomains was confirmed by RNA interference, which revealed that down-regulation of BRD4 most consistently phenocopied BBI (FIG. 1B and FIGS. 7A-7B).

Figure 1C:
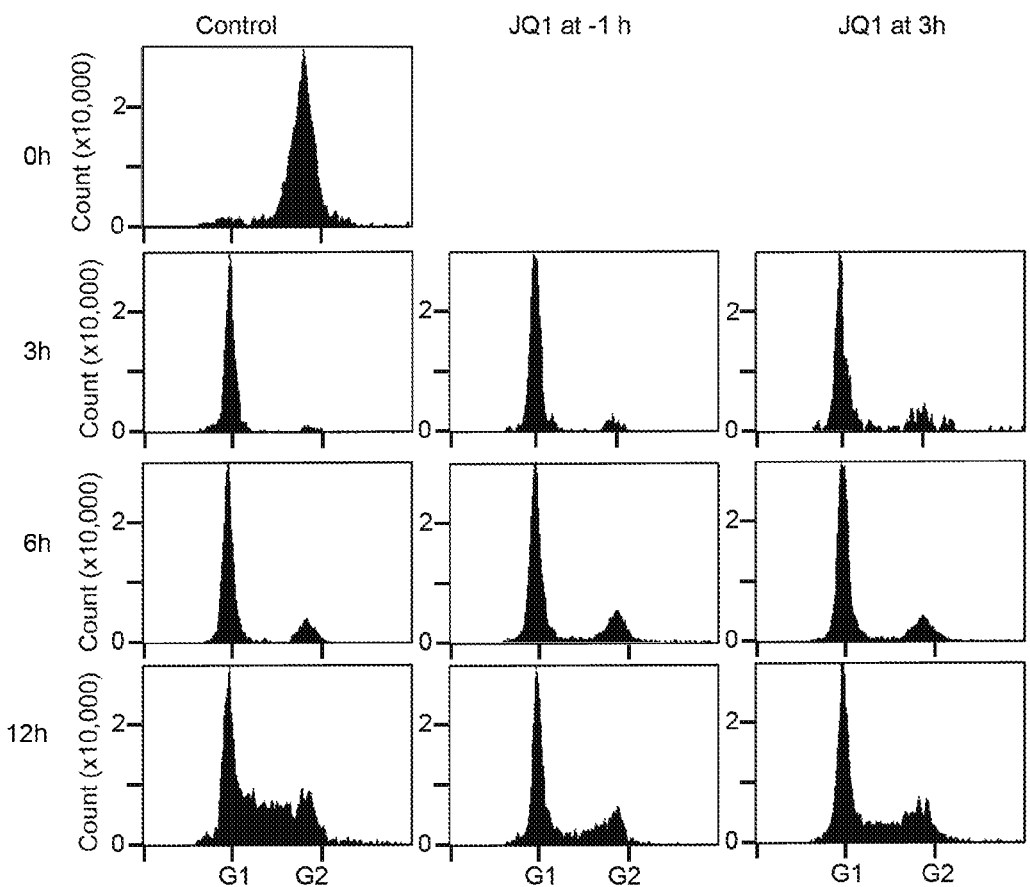
Figure 7C:
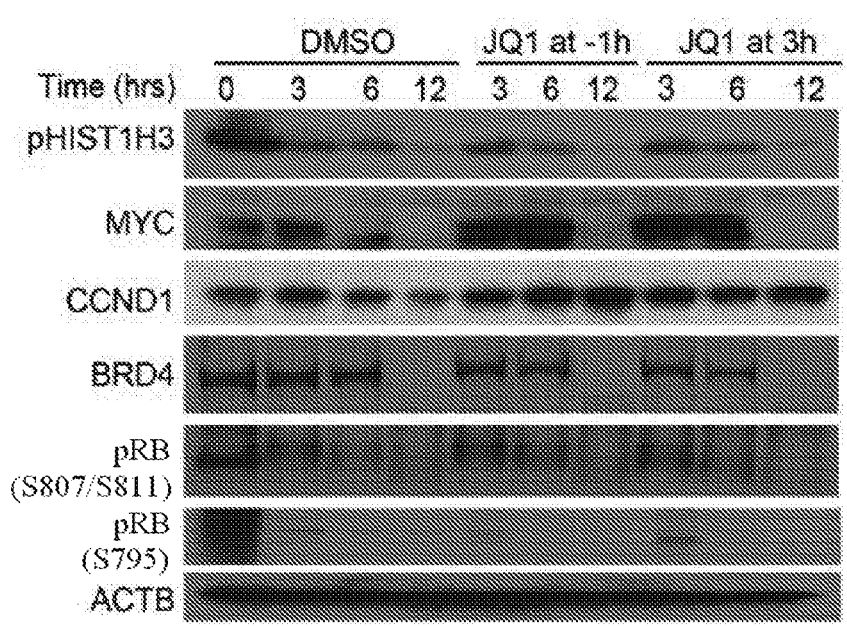
Figure 7D:
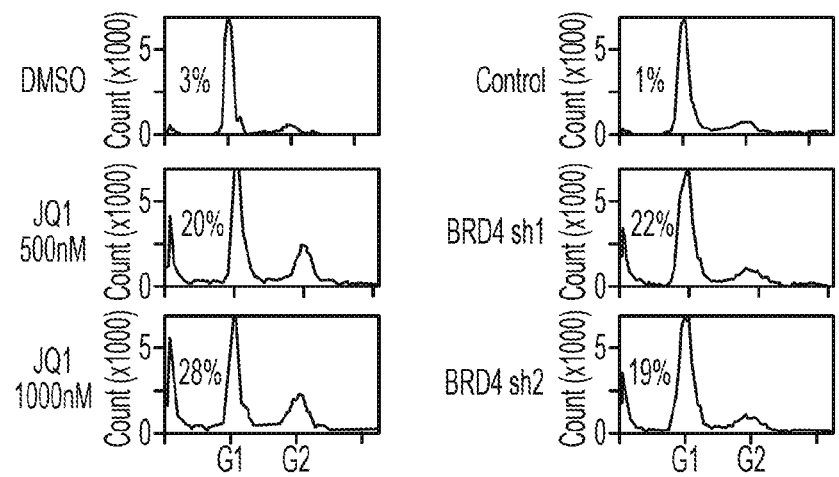
Figure 7E:
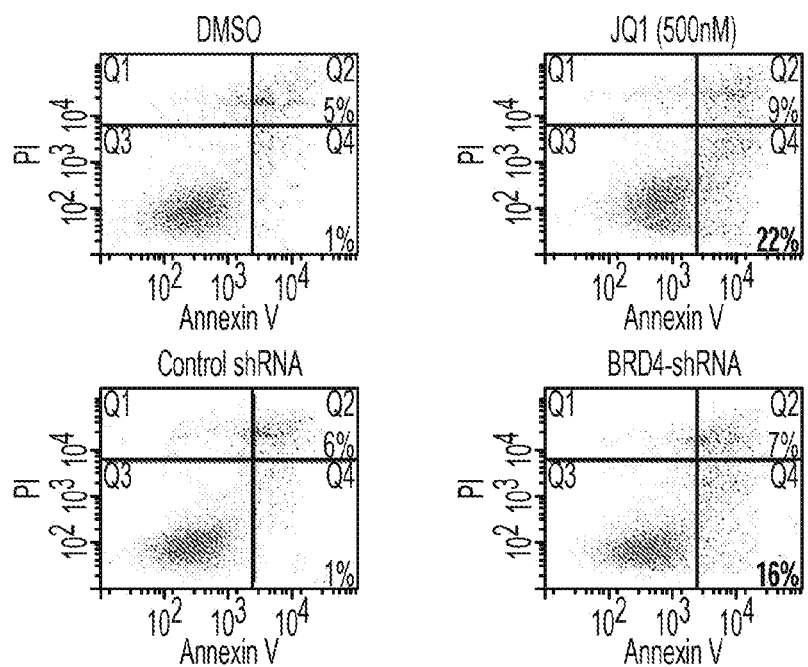

To understand the effect of BBI on TNBC proliferation, the effect of JQ1 at different phases of the cell cycle were characterized. SUM159 cells were first synchronized with nocodazole in G2/M. JQ1 was administered 1 hour before or 3 hours after release, and cell cycle was assessed by flow cytometry. Cells treated with JQ1 before release arrested in early G1 with high cyclin D1 levels, whereas addition of JQ1 3 hours after release from G2/M arrest had less pronounced effects and allowed substantial progression to S and G2/M phases (FIG. 1C and FIGS. 7C-7D). These data are consistent with the reported role of BRD4 in G2/M to G1 phase progression[12,23]. A decrease of BRD4 protein levels was detected as synchronized cells progressed to G1/S, which was further exacerbated by JQ1 treatment perhaps accentuating the effect of BBI (FIG. 7C). Prolonged exposure to JQ1 (48-72 hours) elicited an apoptotic response, measured by increases in the sub-G1 fraction and Annexin-V staining (FIGS. 7D-7E). Comparable induction of early G1 arrest and late apoptosis was observed with BRD4 knock-down, further supporting a key role for this co-activator in TNBC (FIGS. 7D-7E).

Figure 1D:
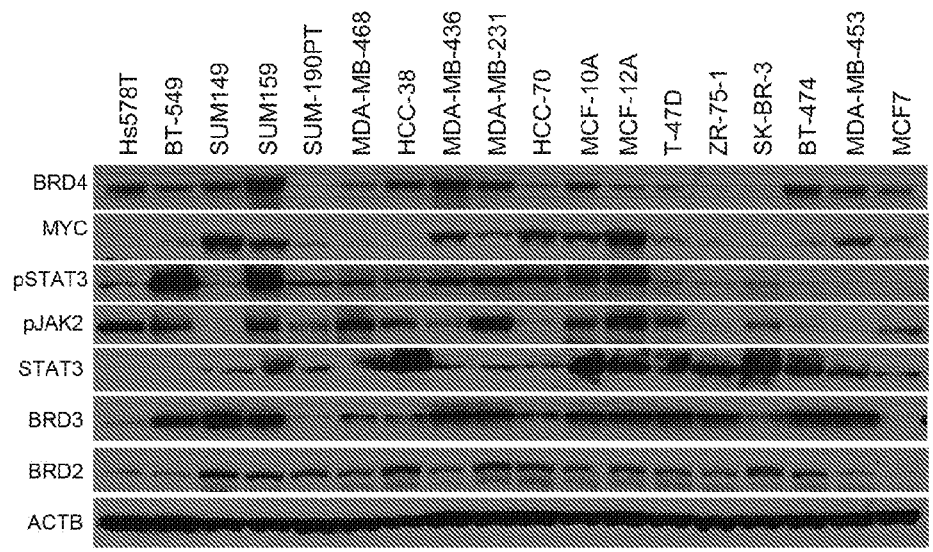

To investigate whether sensitivity to BBI was associated with the abundance of target BET proteins, factors described to mediate the anti-cancer effects of JQ1, or biochemical markers of signaling pathways previously identified as required for TNBC growth[24], immunoblot analysis was performed in a panel of cell lines. The comparative expression of MYC and BRD4, and the comparative abundance of pSTAT3 and pJAK2, were elevated in discrete TNBC lines with high sensitivity to JQ1 (e.g., SUM159), but overall these measurements did not show clear association with JQ1 sensitivity (FIG. 1D). A kinetic study of these factors performed in SUM159 cells treated with JQ1 revealed a decrease in pSTAT3 and pJAK2 after 12 hours and a dose-responsive decrease in MYC at 24 hours (FIGS. 8A-8B). These data are consistent with effects on JAK-STAT signaling reported in T-cell acute lymphoblastic leukemia[25], but diverge from prior studies of hematologic malignancies where BBI rapidly deplete MYC[8,9]. Together, these studies suggest that the response of TNBC to BBI may be mechanistically and phenotypically distinct from prior reports.

Figure 1E:
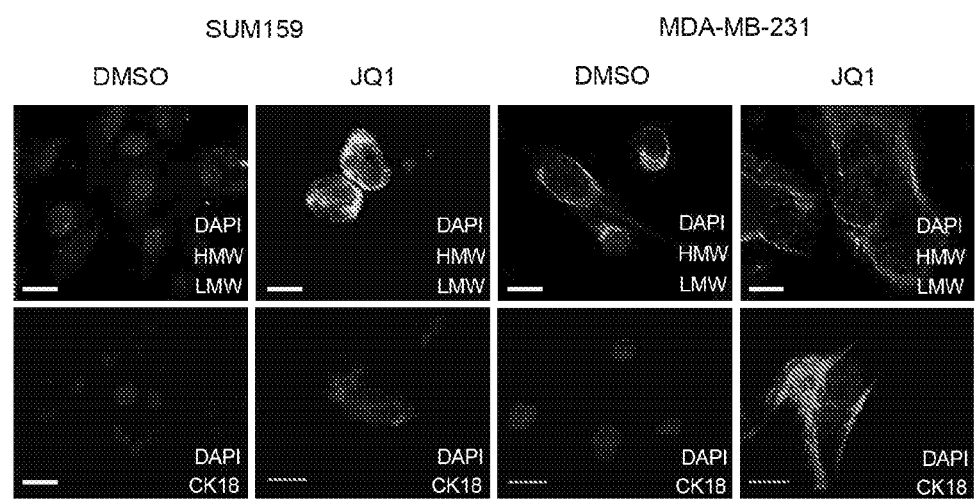

Indeed, significant morphologic changes were observed when culturing TNBC cells with JQ1, suggesting an effect of BET inhibition on cell state (FIG. 8C). To measure effects on cellular senescence, TNBC cells (SUM159 and MDA-MB-231) were treated with JQ1 and performed β-galactosidase staining. BET bromodomain inhibition markedly increased acidic β-galactosidase activity consistent with robust induction of senescence (FIG. 8D). To assess effects on differentiation state, immunofluorescence microscopy was performed for basal and luminal markers. JQ1 treatment resulted in an elevation of low molecular-weight (LMW) cytokeratins and cytokeratin 18 (CK18) characteristic of luminal cells and a concomitant decrease of high molecular-weight (HMW) cytokeratins characteristic of basal cells, implying a shift to a more luminal epithelial phenotype (FIG. 1E). These early, robust effects on senescence and differentiation resonate with prior studies of BBI in cancer[8,14,18], and the emerging biology of BET bromodomains as dynamic mediators of cell state[26].

Figure 1F:
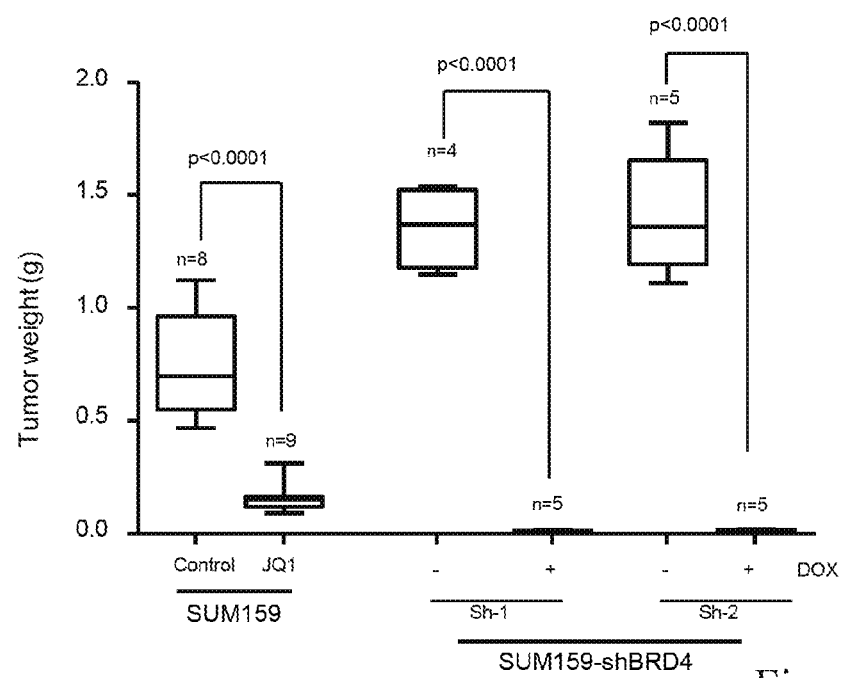
Figure 1G:
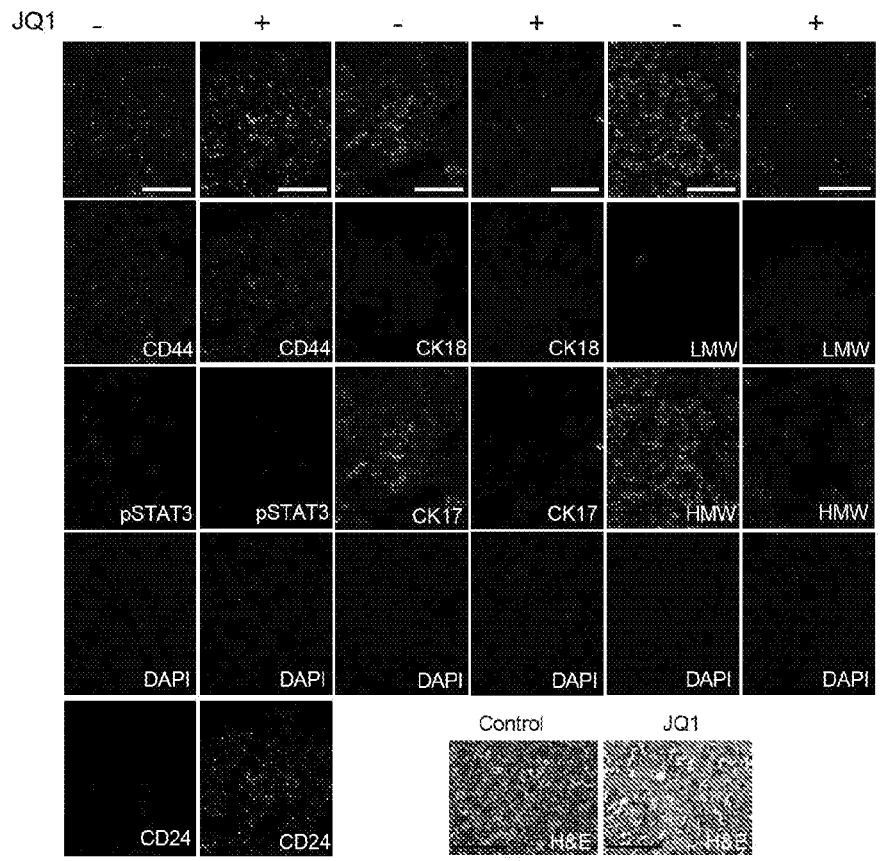
Figure 8F:
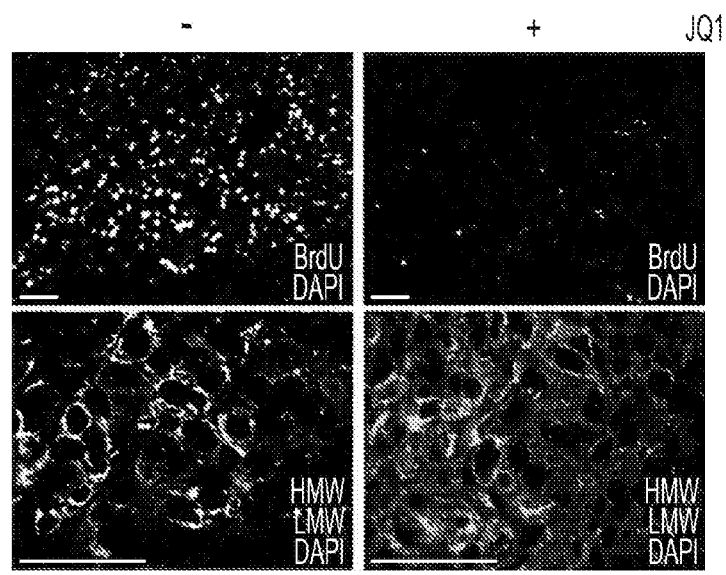
Figure 8G:
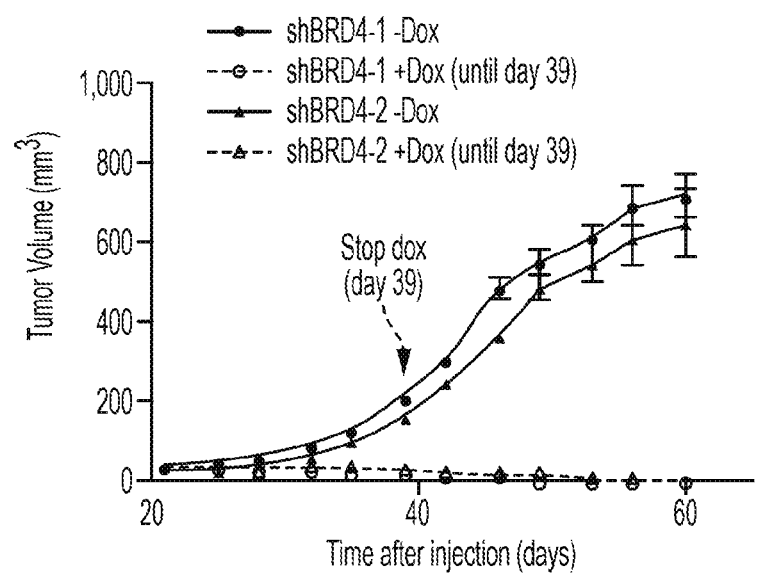

To extend the translational significance of these findings, the ability of JQ1 to inhibit the growth of breast tumors in four murine xenograft models of human breast cancer in vivo was evaluated. Two weeks of JQ1 treatment efficiently inhibited the growth of established tumors derived from SUM159 and MDA-MB-231 TNBC cell lines, as well as that of patient-derived primary human TNBC xenografts (FIG. 1F and FIGS. 8E-8F). The specific dependence on BRD4 in vivo was then established using two independent TET-inducible shRNAs in the SUM159 model. Downregulation of BRD4 was found to have even more pronounced effects leading to complete tumor regression and failure to regrow even after doxycycline treatment was discontinued (FIG. 1F and FIG. 8G). Evidence of BBI-induced basal-to-luminal differentiation was confirmed in vivo, by pharmacodynamic measurements of basal (decreased HMW cytokeratins and pSTAT3) and luminal (increased LMW cytokeratins and CD24) markers by immunofluorescence microscopy (FIG. 1G and FIG. 8F).

Transcriptional Targets of BBI in TNBC

Figure 2A:
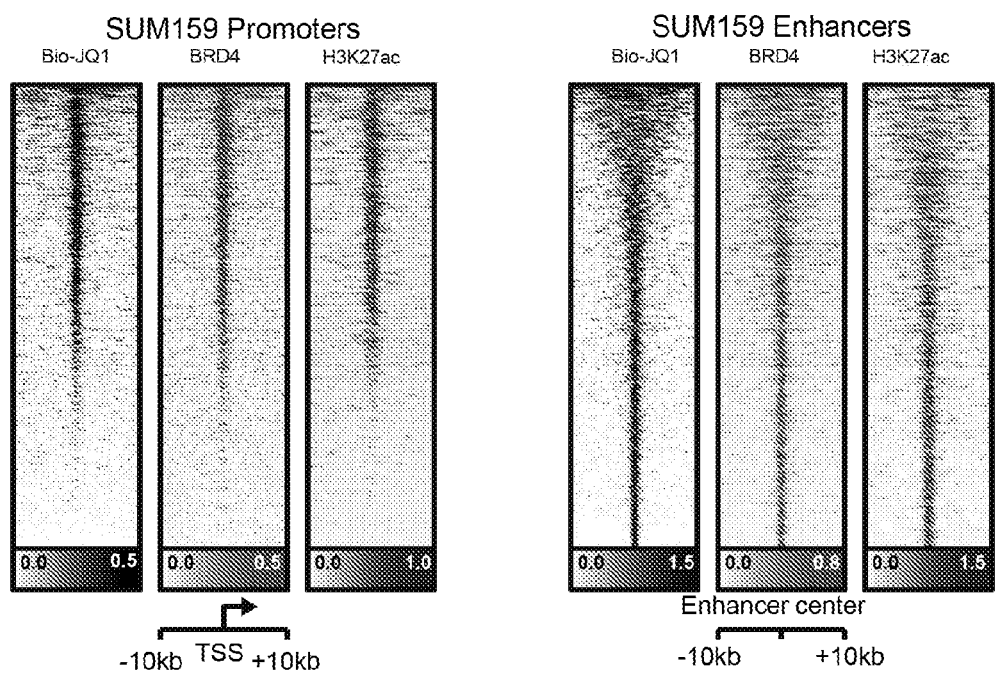
FIGS. 2A-2G. BRD4 genome binding and super-enhancer-associated gene transcription in TNBC.
Figure 2B:
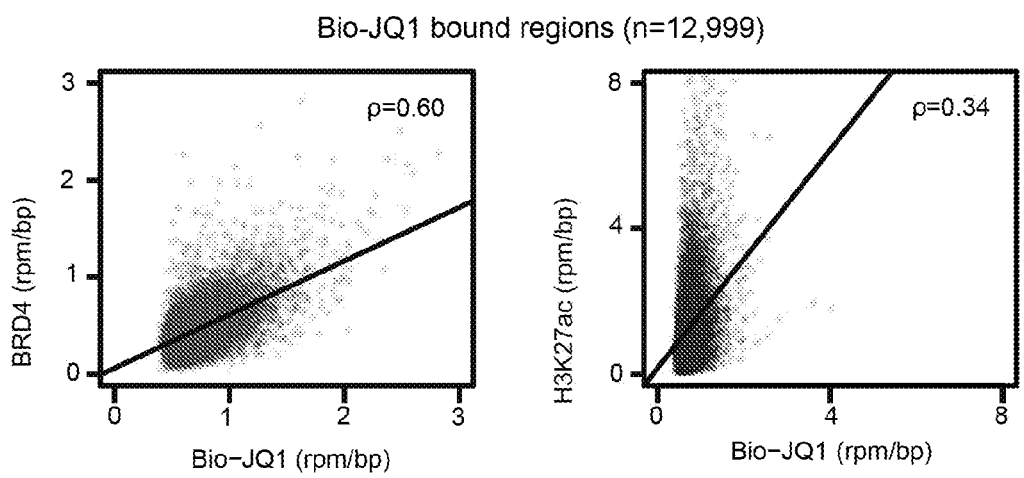
Figure 2C:
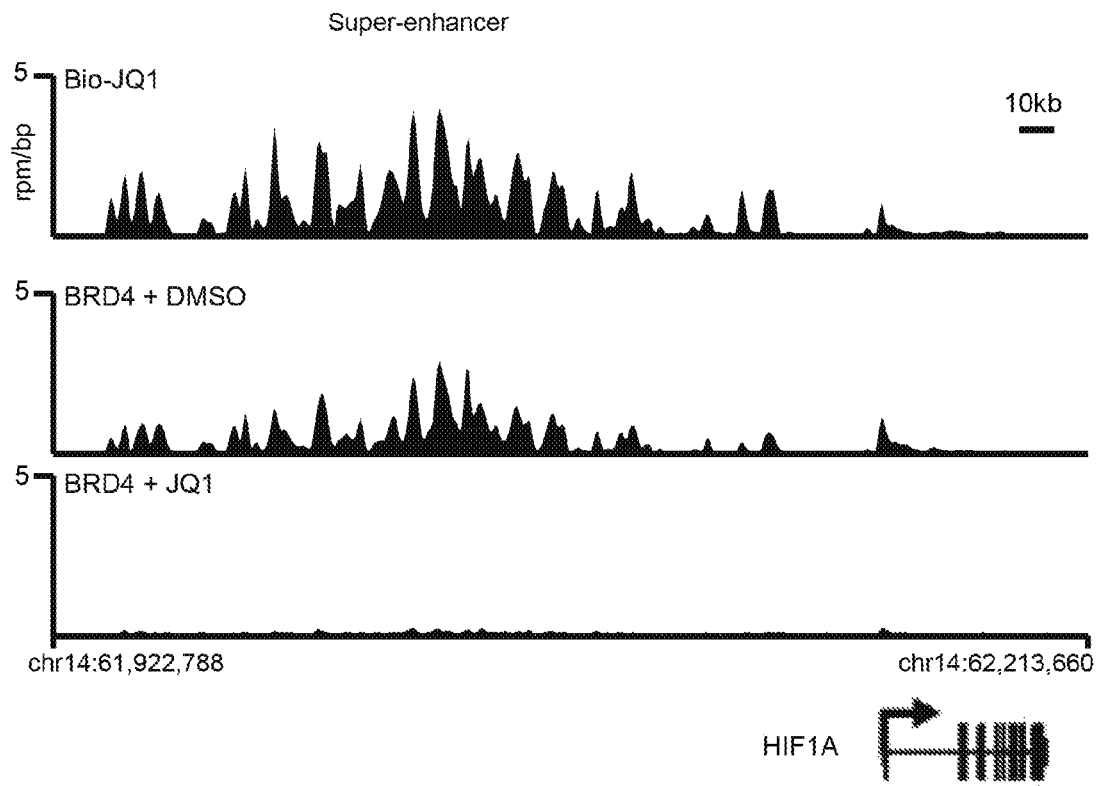

Using integrated epigenomic analysis, the direct transcriptional targets of BBI in TNBC were next identified. A technology capable of locating chromatin-active small molecules spatially to discrete sites of action within the epigenome was reported, by pairing ligand-affinity chromatography of pre-fixed and fragmented nuclear chromatin with massively parallel DNA sequencing (Chem-seq)[27]. Chem-seq was performed using a retrievable, biotinylated derivative of JQ1 (Bio-JQ1)[27], and a BBI-sensitive TNBC cell line (SUM159). Sites of BBI function were mapped by aligning enriched sequence reads to the human genome, and comparing locally and globally to ChIP-seq data for promoters (histone 3 lysine 4 trimethylation; H3K4me3), enhancers (histone 3 lysine 27 acetylation; H3K27ac) and the BRD4 co-activator. Bromodomain inhibitor binding was identified at active promoter and enhancer regions (FIG. 2A), with a near-perfect co-localization to sites of BRD4 enrichment and strong enrichment at active enhancers, genome-wide (FIG. 2B). As expected, BBI was found to efficiently displace chromatin-bound BRD4 in treated TNBC cells (FIG. 2C). This effect was more pronounced at genomic regions exhibiting elevated Bio-JQ1 enrichment by Chem-seq (FIG. 2D), supporting enhanced disruption of BRD4 binding at sites of greatest enrichment. BRD4 ChIP-seq studies in SUM149 cells, a second BBI sensitive TNBC line, confirmed these findings (FIG. 9A).

Figure 2D:
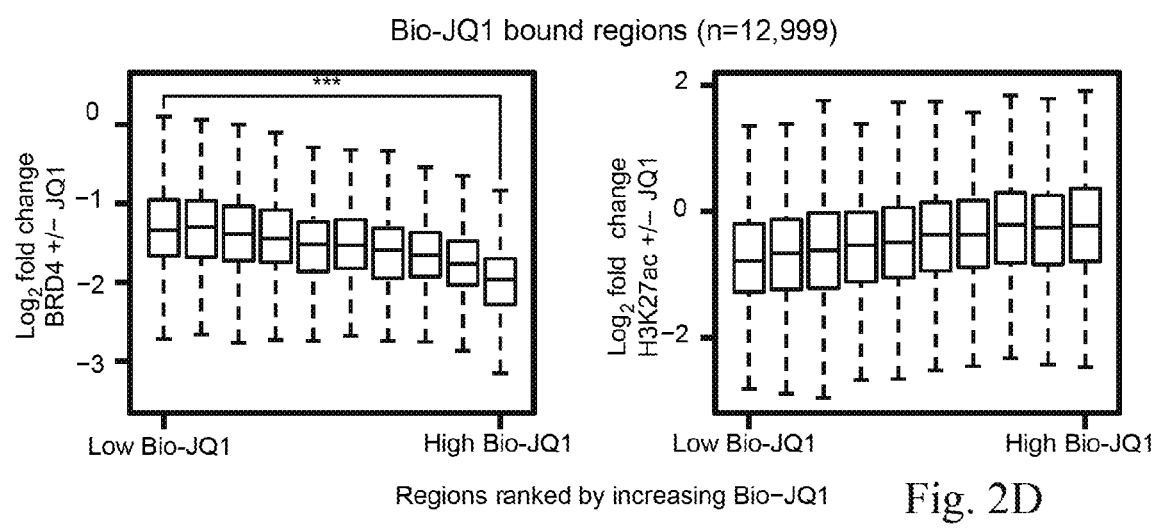
Figure 2E:
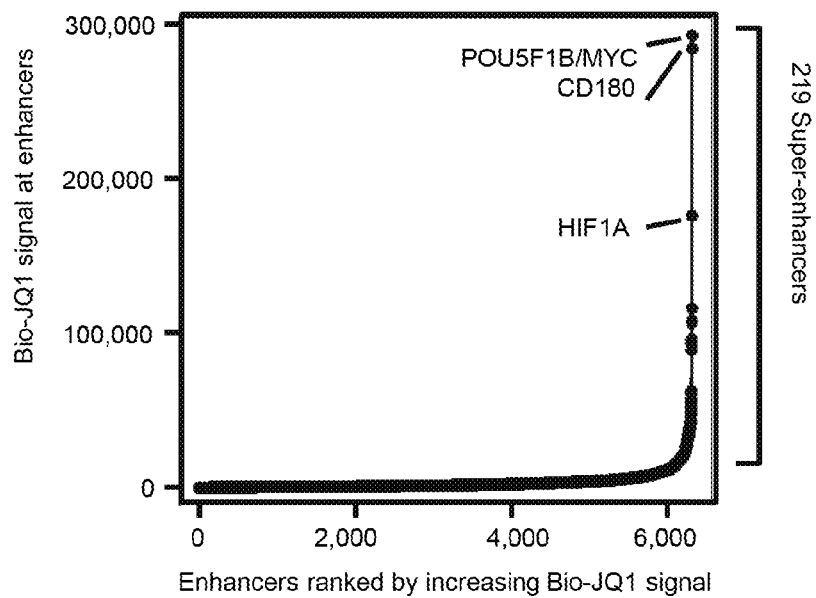
Figure 2F:
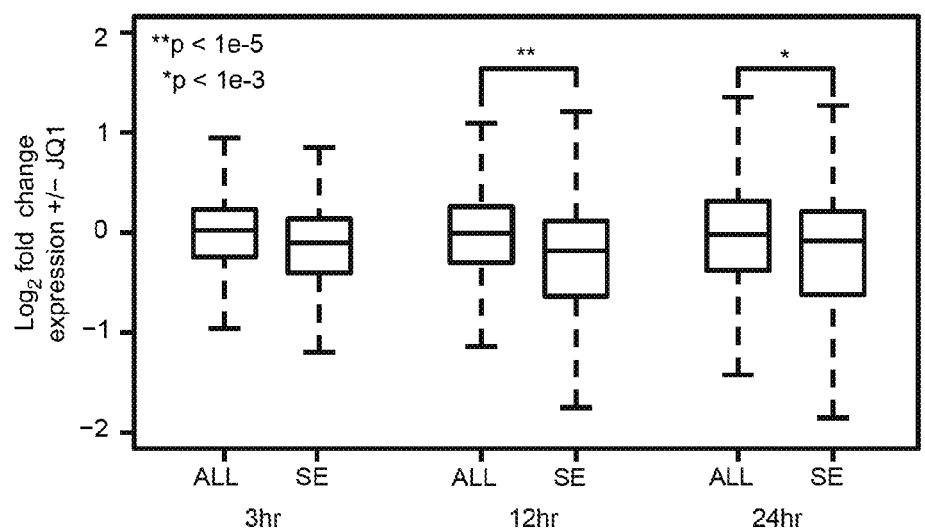
Figure 2G:
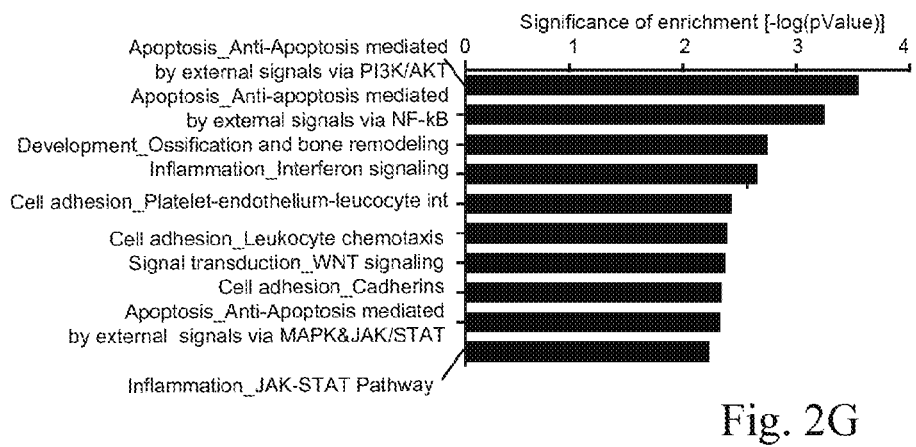

To identify biologically relevant, direct targets of BBI in SUM159 and SUM149 cells, binding of Bio-JQ1 and BRD4 genome-wide was quantified and strong enrichment was found at 219 and 159 super-enhancers, respectively (SEs; FIG. 2E and FIG. 9B)[6,16-18]. Super-enhancers have been found to be more efficiently depleted of BRD4 by JQ1, explaining selective effects on SE-associated gene expression[6,16-18]. Among the top SE-associated genes in SUM159 were POU5F1B/MYC[28], IRX[229,30], HIF1α[31], TFs with known roles in development and breast cancer, and CD180 (RP105), a TLR4-accessory molecule implicated in obesity, inflammation, and atherosclerosis[32] (FIG. 9B). POU5F1B/MYC[28] and HIF1α were top among SE-associated genes in SUM149 cells as well. Analyzing gene expression changes in both cell lines by RNA-seq at different time points following JQ1 treatment demonstrated consistent, proportionate effects on gene expression (FIG. 9C), and identified that genes associated with SEs were significantly more likely to be down-regulated compared to all active genes (FIG. 2F and FIG. 9D). The expression of genes that are up or down regulated by JQ1 versus DMSO after 24 hours treatment was performed at 3, 12, and 24 hours after treatment. Up regulated genes included DHRS2, HEXIM and CDKN1A and down regulated genes include CD180, PTPN22, and HNF4G. Gene expression changes were observed as early as 3 hours after JQ1 treatment and, as expected acutely following SE disruption, more genes were significantly down- than up-regulated (FIGS. 9D-9F). Importantly, most down-regulated genes were direct BRD4 targets whereas up-regulated genes were not, and this difference was most pronounced at early time points after JQ1 treatment (data not shown). In SUM159 cells CD180, PTPN22, HNF4G, and KRT17 were among the top down-regulated genes, whereas HEXIM a gene known to be upregulated by BET bromodomain inhibitors, and DHRS2 and CDKN1A were among the top upregulated genes. Unsupervised functional analysis of target pathways affected by JQ1 using the Metacore suit[33] revealed down-regulation of regulatory and effector genes in anti-apoptotic, bone remodeling, WNT, and JAK/STAT signaling pathways (FIG. 2G). Together, these studies support selective disruption of SE-associated genes by JQ1, leading to deregulation of coordinated transcriptional pathways involved in cell proliferation, invasion, and survival.

Resistance to Bromodomain Inhibition in BET-Dependent TNBC

Acquired resistance is a nearly inevitable feature of targeted therapies. Dissecting resistance to targeted therapy is critical to elucidate mechanisms of drug and target action, and to suggest approaches to treat or anticipate drug resistance in patients. Therefore, BBI-resistant TNBC cell lines by long-term culture of SUM159 and SUM149 cells in escalating doses of JQ1 were established.

Figure 3A:
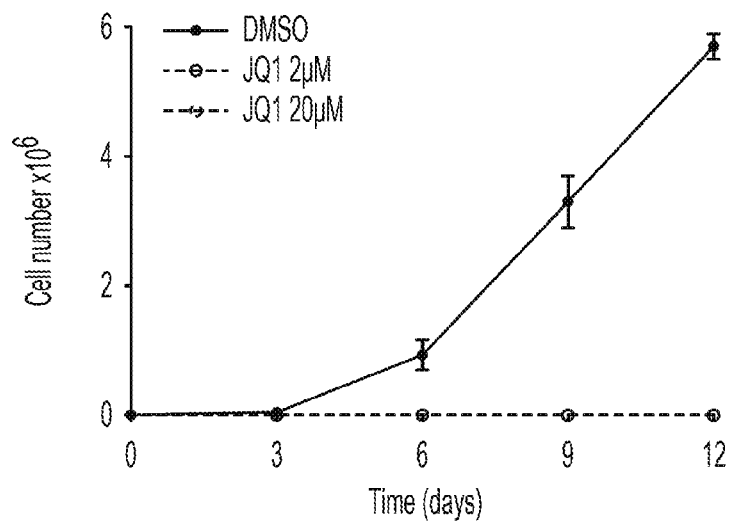
Figure 3B:
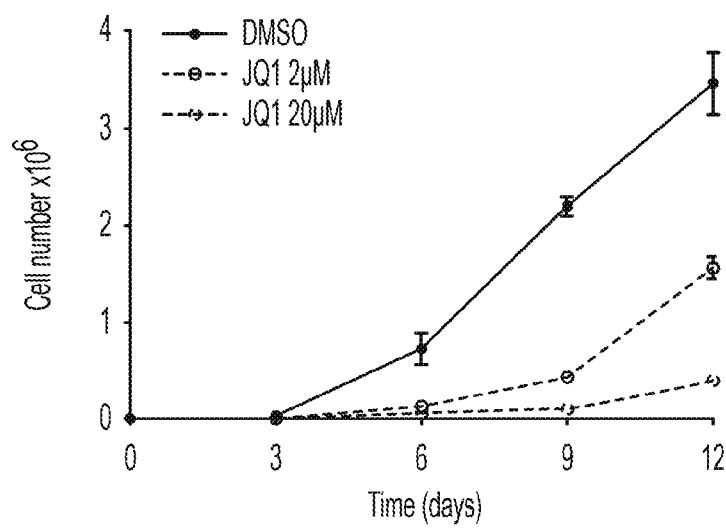
Figure 3E:
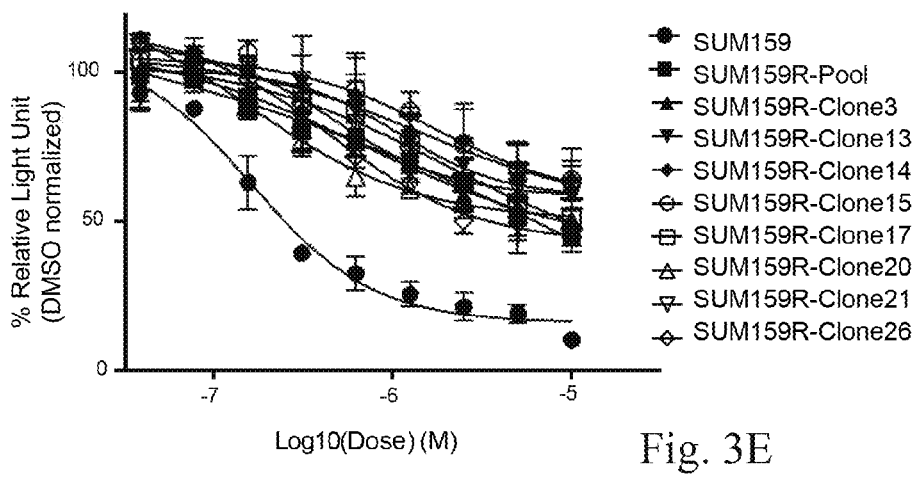
Figure 3F:
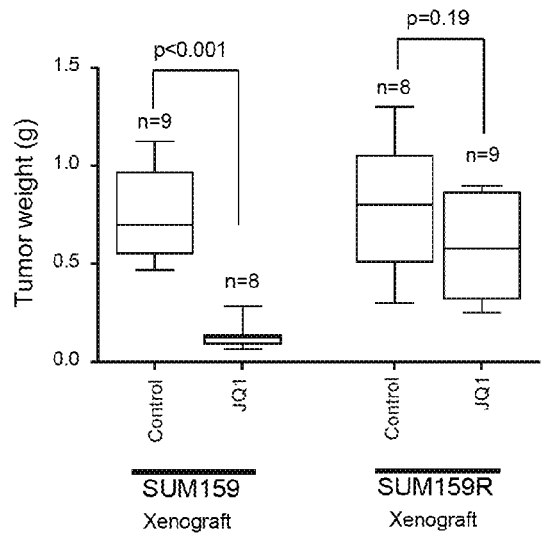
Figure 10A:
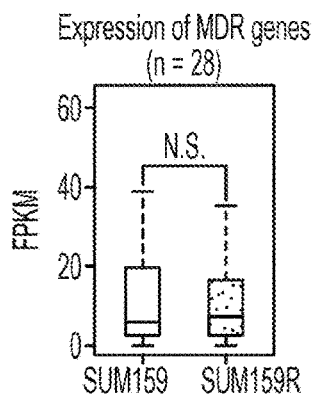
FIGS. 10A-10D. Characterization of SUM159R cells.
Figure 10B:
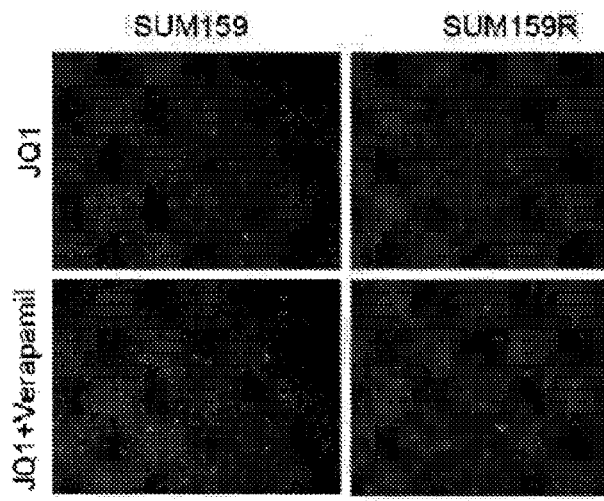
Figure 10B:
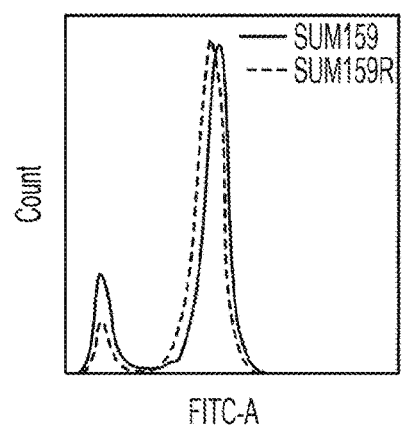
Figure 10C:
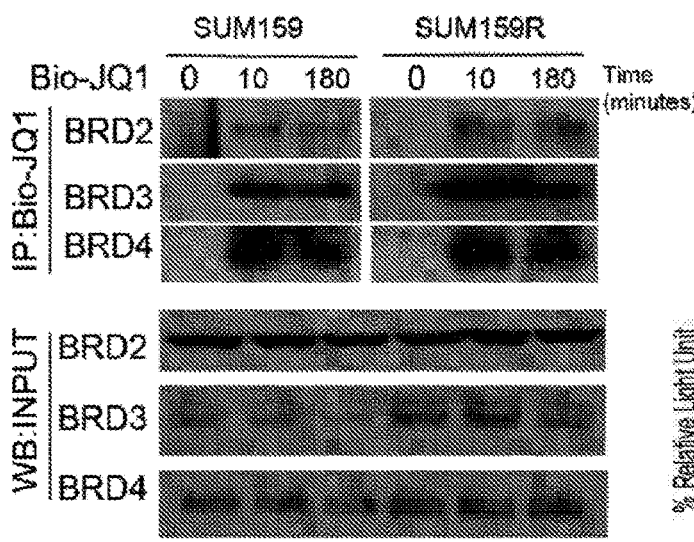

The proliferation of parental SUM159 and SUM149 cell lines is severely impaired by low (0.5 µM) and high (2.0 µM) doses of JQ1, and viable cells decrease in number over 6 days of treatment (FIG. 3A and FIG. 9G). In contrast, isolated JQ1-resistant cells (SUM159R and SUM149R) continue to proliferate linearly over time, even in the presence of high concentrations (up to 20 µM) of JQ1 (FIG. 3B and FIG. 9G). BBI-resistance is not attributable to drug export, as structurally divergent inhibitors are equally inactive as JQ1 (FIG. 3C), MDR1 and other transporters are not transcriptionally upregulated (FIG. 10A), and co-incubation with MDR1 inhibitors such as verapamil had no effect (FIG. 10B). Further support is provided by the equivalent engagement of BRD4 in sensitive and resistant cells, demonstrated by Bio-JQ1 administration with ligand chromatography and immunoblot (FIG. 10C). Weak but evident dose-ranging effects of all BBIs on ATP content were observed in short-term culture (FIG. 3C), and with the exception of JQ1 the EC50s are consistent with concentrations required to attenuate cell proliferation in sensitive lines (FIG. 1A). The shouldering of these short-term dose-response curves supports the phenotype of drug-resistant proliferation without accompanying cell death that was unambiguously observed over time in long-term culture (FIG. 3A). Sensitive and resistant TNBC cells are equally sensitive to compounds from divergent drug classes, such as CXCR2 and JAK2 inhibitors known to target TNBC cells[34]; thus resistance is specific to BET inhibitors among other targeted agents (FIG. 3D). Adaptive drug resistance was not attributable to outgrowth of a minor subpopulation of cells, as 10 independent single cell-derived clones showed the same resistance profile as a pool of SUM159R cells (FIG. 3E). Similar results were obtained in vivo, as xenografts derived from SUM159R cells were not responsive to JQ1 treatment in parallel studies with sensitive TNBC cells (FIG. 3F).

Figure 3G:
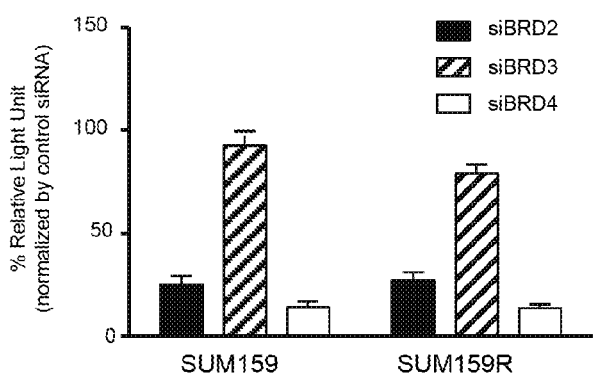
Figure 10D:
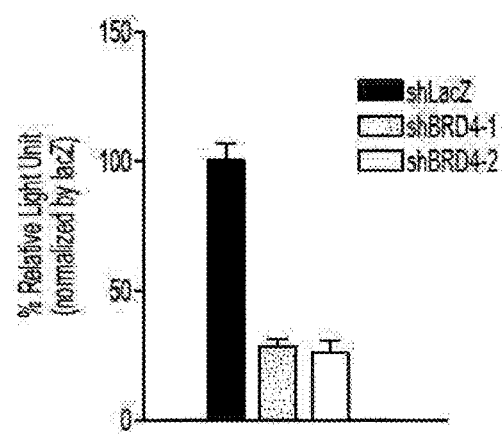
Figure 12A:
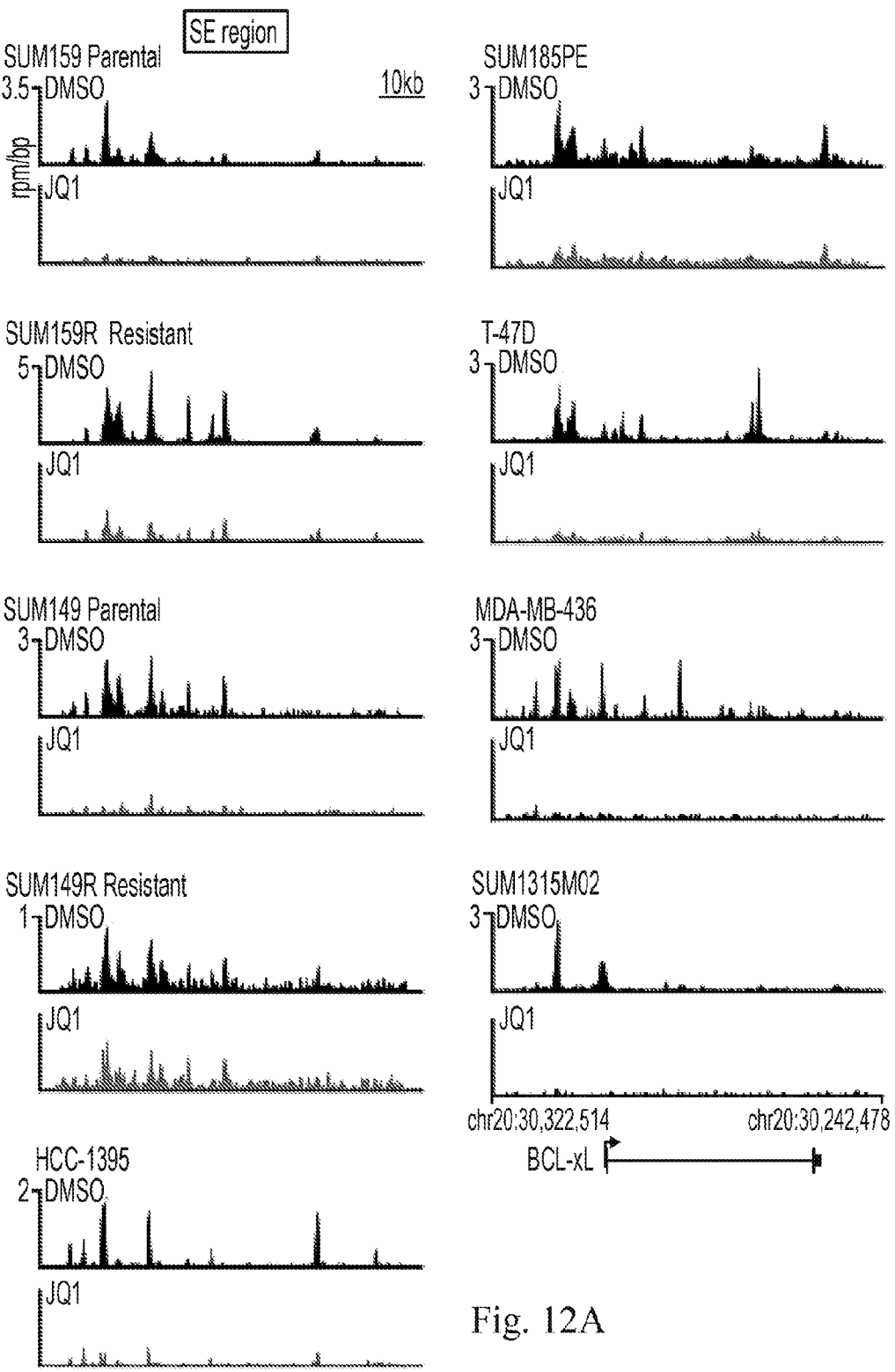
FIGS. 12A-12D. JQ1 response in other breast cancer cell lines.
Figure 12B:
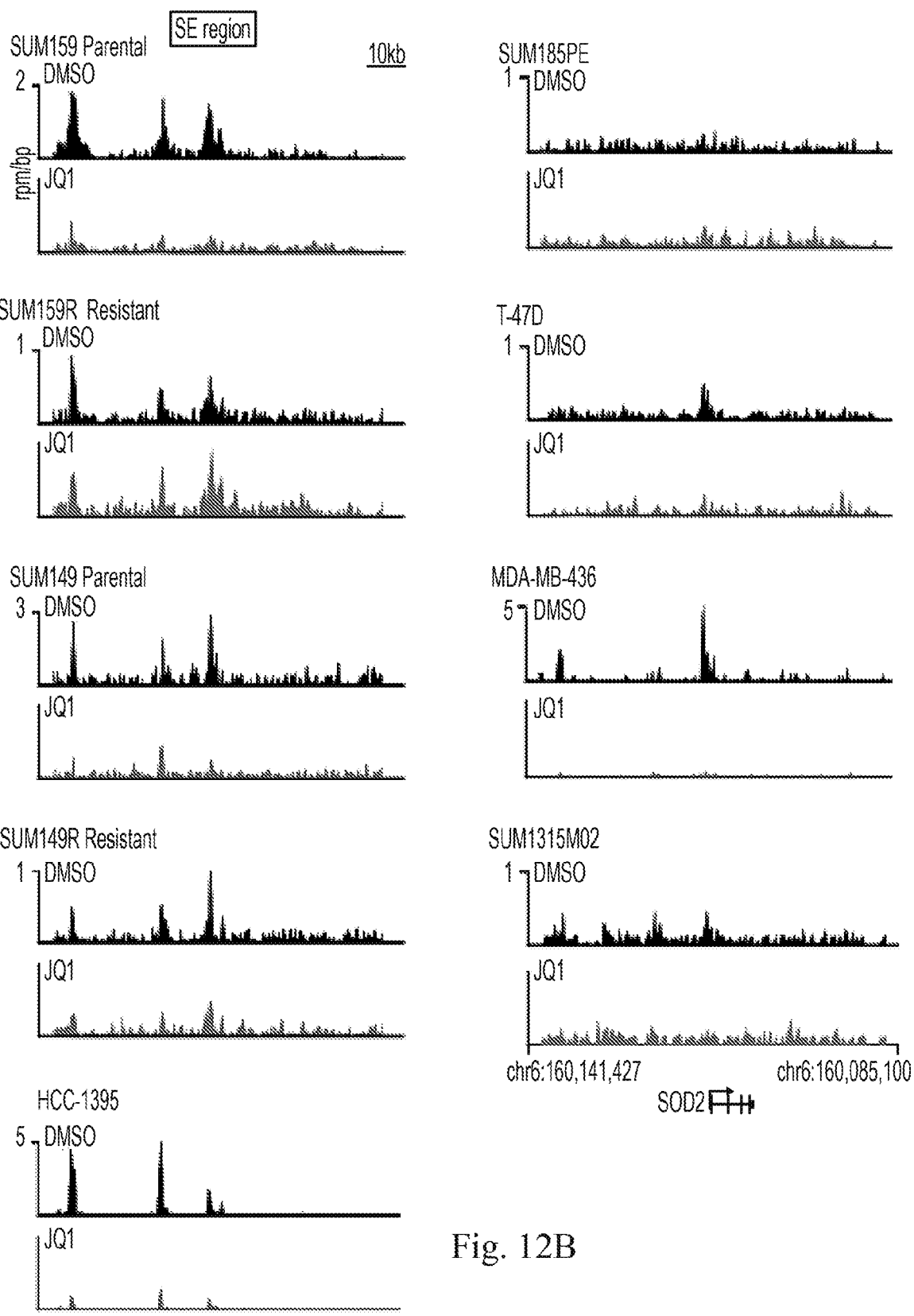
Figure 12C:
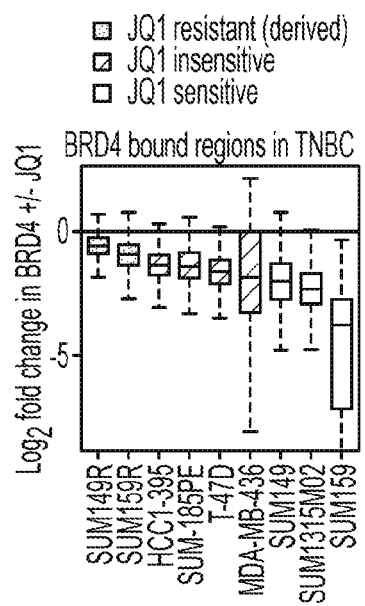
Figure 12D:
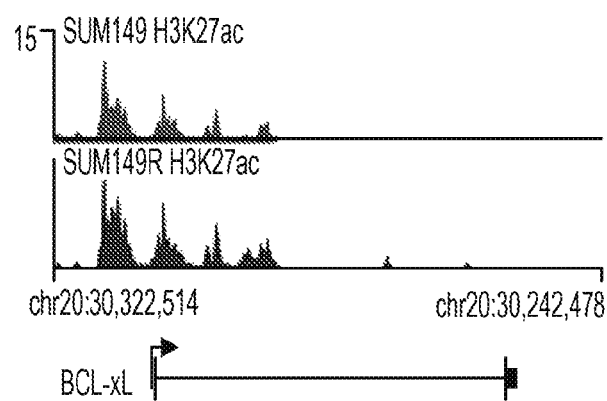

Resistance to targeted therapy is often mediated by somatic alteration of the gene encoding the target protein, as with so-called "gatekeeper" mutations of tyrosine kinases[35]. In all resistant TNBC populations studied, exome sequencing failed to identify alterations to BET bromodomain-encoding genes. Adaptive resistance to targeted therapy commonly also arises from by-pass pathway activation, rendering cells dependent on a new signaling factor and no longer dependent on the drug target, as with MET activation following EGFR inhibitor resistance in lung cancer[36]. In contrast here, exome sequencing failed to identify selected or emergent alterations in known driver genes that could suggest parallel pathway activation. Surprisingly, SUM159R cells remain dependent on BRD4 for cell growth, as established by RNA interference experiments (FIG. 3G and FIG. 10D).

Bromodomain-Independent Localization of BRD4 in Resistant TNBC

Figures 4A, 4B, 4C, 4D:
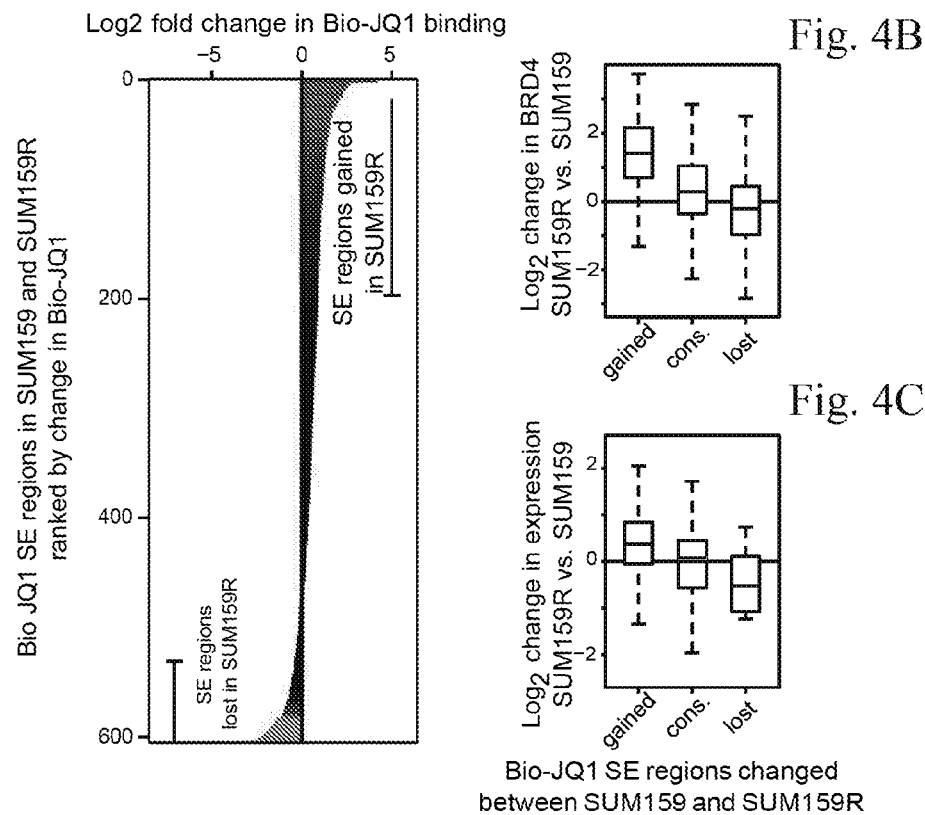
FIGS. 4A-4I. BRD4 genome binding and super-enhancers in BBI resistant TNBC.

Persistent dependence on BRD4 and the absence of a genetic explanation prompted the consideration of epigenomic mechanisms underlying drug resistance. Genome-wide measurements of chromatin structure, BRD4, and JQ1 localization were made in SUM159R, allowing pairwise comparison to SUM159. Differential SE analysis has proven a powerful tool to study dynamic changes in cell state attributable to BRD4 function, as described in a study of inflammatory transitions in macrophages and endothelial cells[26]. To characterize a putative BRD4-dependent cell state change, Bio-JQ1 Chem-seq profiles of sensitive and resistant cells were compared. Differential SE analysis found a significant gain in the number of SEs in resistant SUM159R cells, and a less pronounced loss of fewer SEs (FIG. 4A). The gain of Bio-JQ1 SEs was associated with enrichment for BRD4 binding to these genomic loci (FIG. 4B) and also with increased transcription of the associated genes (FIG. 4C). Among the top gained super-enhancers in SUM159 cells was an upstream and intragenic region of H3K27ac enrichment at the BCL-xL locus (FIG. 4D). Notably, BCL-xL was among the few, highly up-regulated genes in resistant cells by expression profiling, a finding that was confirmed by immunoblot (FIG. 11A). Deregulated, increased expression of this anti-apoptotic factor may confer resistance to apoptosis during long-term treatment with JQ1.

Figure 4E:
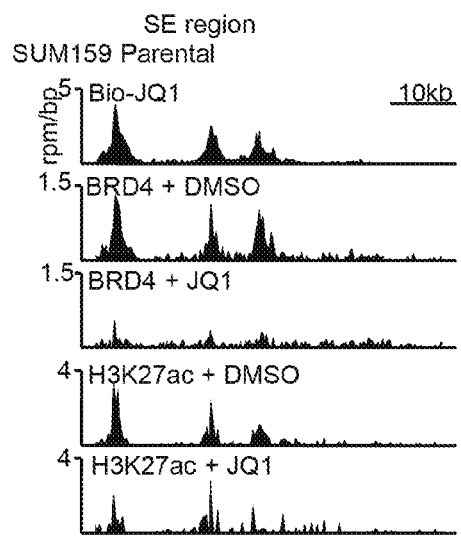
Figure 4E:
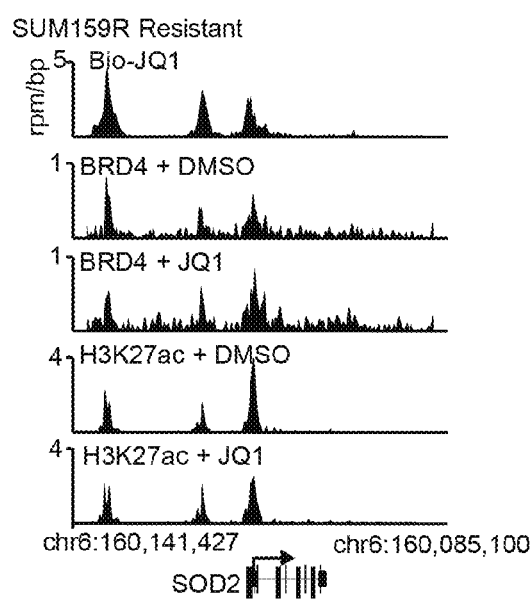
Figure 4F:
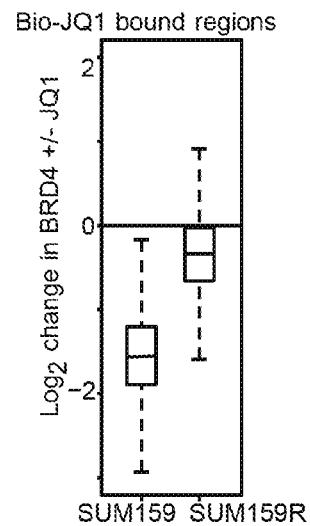
Figure 4G:
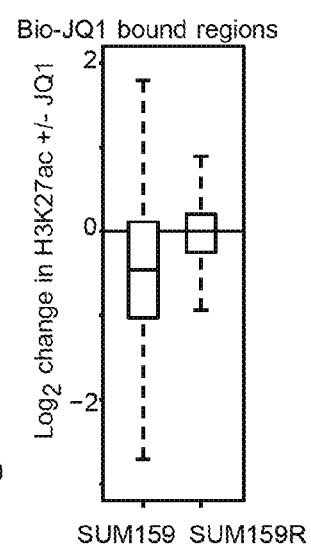
Figure 4H:
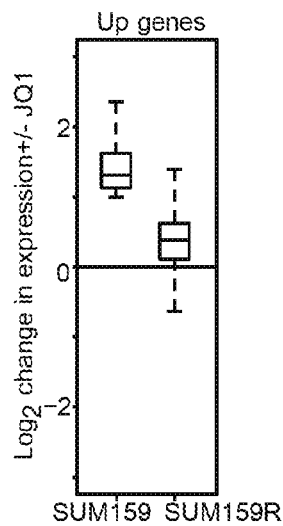
Figure 4I:
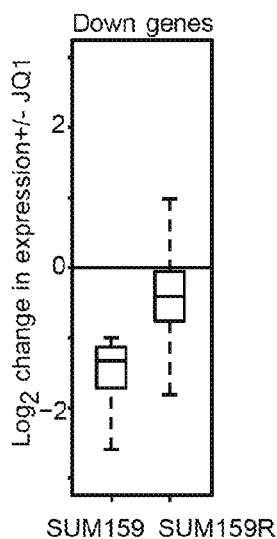

It is hypothesized that epigenomic resistance to JQ1 may arise via the recruitment of BRD4 to SE loci in a bromodomain-independent manner. BRD4 ChIP-seq was performed on sensitive and resistant cells, with and without JQ1 exposure. These studies confirmed the key mechanistic finding that BRD4 is not displaced from chromatin following JQ1 treatment in SUM159R cells (FIG. 4E). At Chem-seq-defined SE regions, SUM159 cells are depleted of BRD4 whereas SUM159R cells retain chromatin-bound BRD4 (FIG. 4F). Functionally, JQ1 treatment of resistant cells fails to influence H3K27ac (FIG. 4G) or global transcription (FIG. 11B), even among the most dynamically JQ1 up-regulated and down-regulated transcripts in SUM159 (FIGS. 4H-4I). Notably, several luminal markers including FOXA1, a key luminal transcription factor[37,38], CD24, and luminal cytokeratins had higher levels in SUM159R cells both in cell culture and in vivo, whereas the expression of basal-cell markers including CD44, FOXA2, pSTAT3, and basal cytokeratins was decreased (FIGS. 11C-11D). Together with the above pull-down data confirming direct binding of JQ1 to BRD4 and Chem-seq data demonstrating co-localization with BRD4 in resistant TNBC cells, these data support a model whereby resistance arises via essential BRD4 recruitment back to chromatin but in a bromodomain-independent manner. Essentially the same observations were made in SUM149R cells and even in cell lines with inherent resistance to JQ1 (FIGS. 9E-9G and 6A-6D), suggesting a more general mechanism of epigenomic resistance to BET inhibition.

Accumulation of pBRD4 in JQ1-Resistant TNBC

In addition to the twin bromodomains, BRD4 possesses additional structural features that bind defined gene-regulatory factors. Indeed, BRD4 was first identified as a mediator-associated factor by Kornberg[39]. More recent proteomic studies revealed avid binding of the extra-terminal domain to ATAD5, CHD4, GLTSCR1, JMJD6, and NSD3[40], and of the distal carboxy-terminus to CDK9 and Cyclin-T1[41]. Many of these factors possess epigenetic reader modules of their own, and the larger macromolecular complexes in which they function may contribute to bromodomain-independent recruitment of BRD4. To disclose potential differences in BRD4-associated complexes between sensitive and resistant SUM159 cells, an unbiased proteomic analysis was performed using RIME (rapid immunoprecipitation mass spectrometry of endogenous proteins)[42] in the presence and absence of JQ1.

Figure 5A:
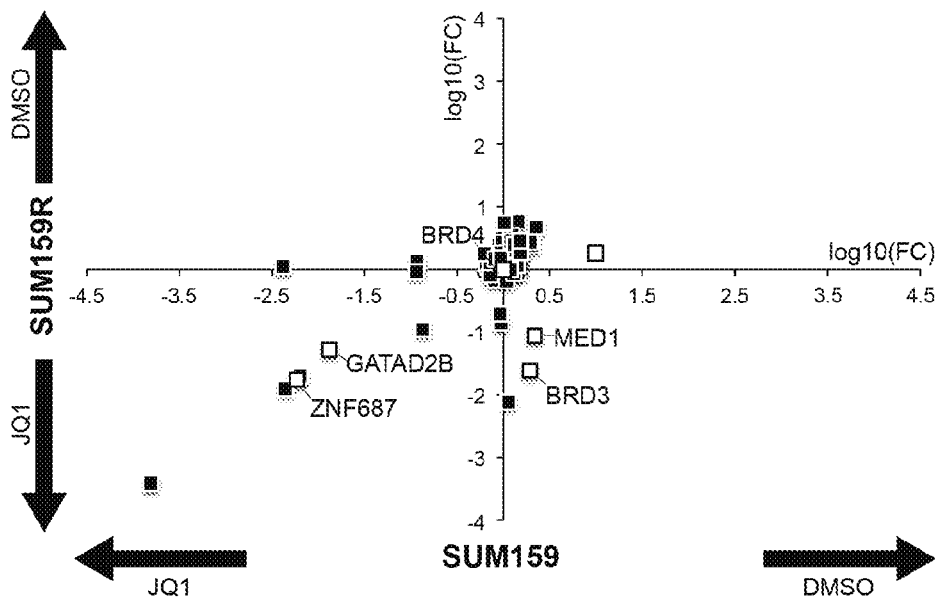
FIGS. 5A-5E. Mechanism of BBI resistance in TNBCs. All error bars represent SEM.
Figure 5B:
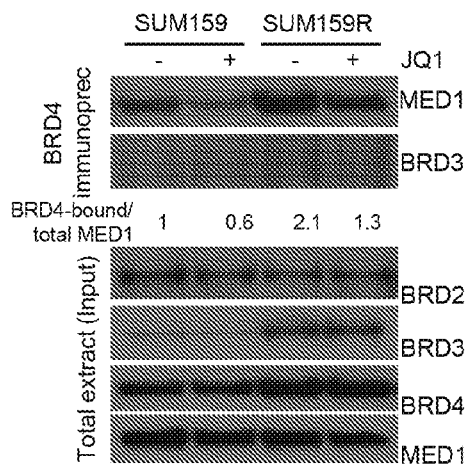
Figure 5C:
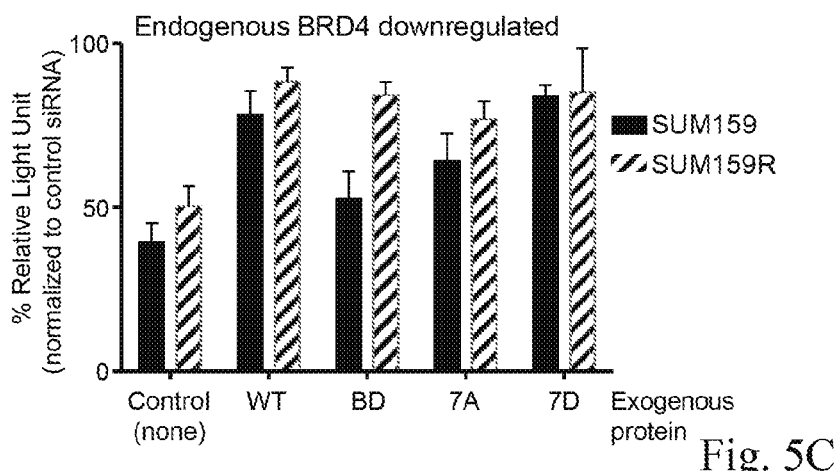
Figure 5D:
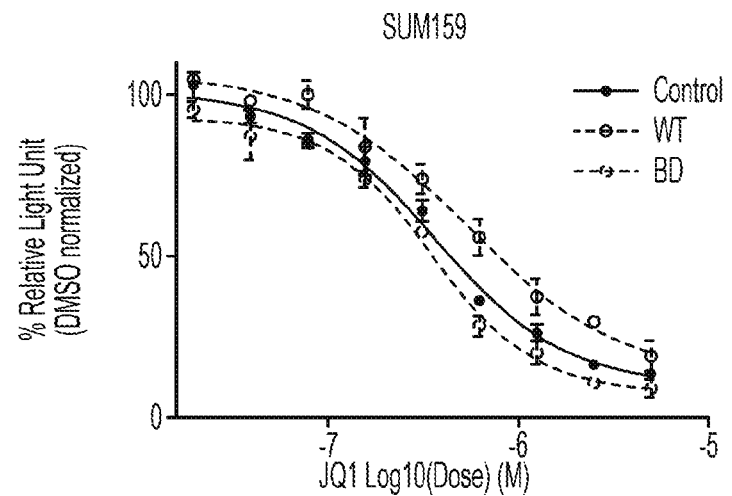
Figure 13A:
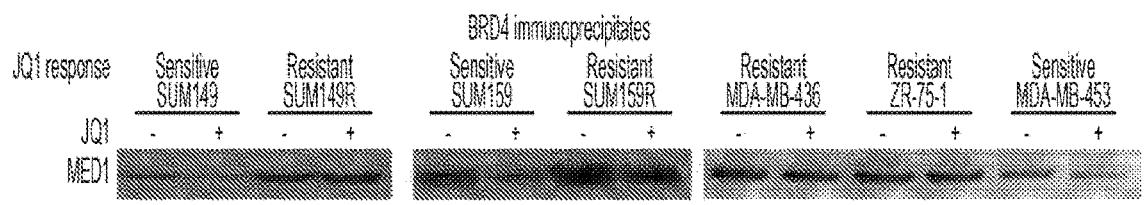

Analysis for BRD4-associated proteins enriched in resistant compared to parental cells identified MED1 and BRD3. BRD4 bound avidly to these proteins even in the presence of JQ1 (FIGS. 5A-5B and Table 1). Observations from RIME data were pursued by BRD4 immunoprecipitation followed by immunoblot analysis for MED1 and BRD3. JQ1 efficiently displaced BRD4 from MED1 in sensitive cells, but had no such effect in resistant cells where increased association of MED1 with BRD4 was confirmed (FIG. 5C). These findings were confirmed in SUM149 and BBI-resistant SUM149R cells, as well as TNBC and luminal cell lines exhibiting inherent resistance to BBI (FIG. 13A). Increased association of BRD4 and BRD3 in SUM159R cells was not confirmed by immunoblot (FIG. 5C), though elevated BRD3 abundance was observed (FIG. 5D).

Figure 5E:
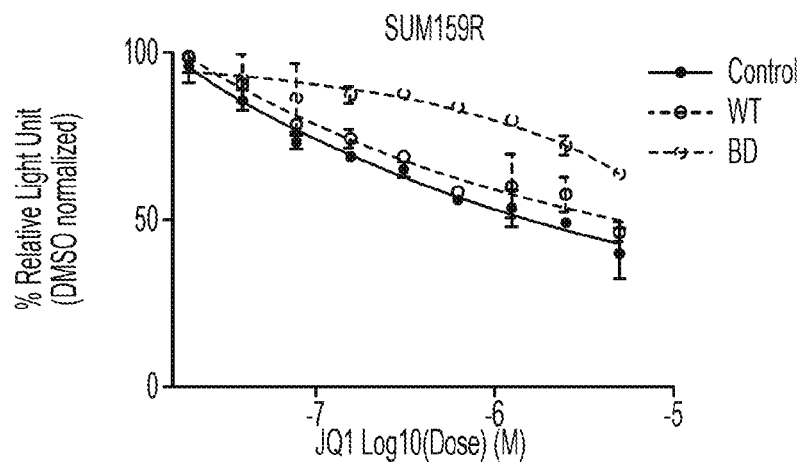
Figure 13B:
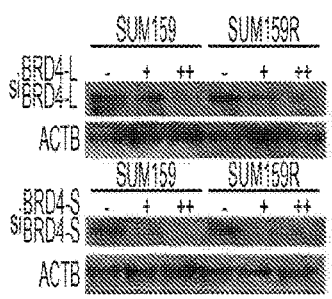
Figure 13D:
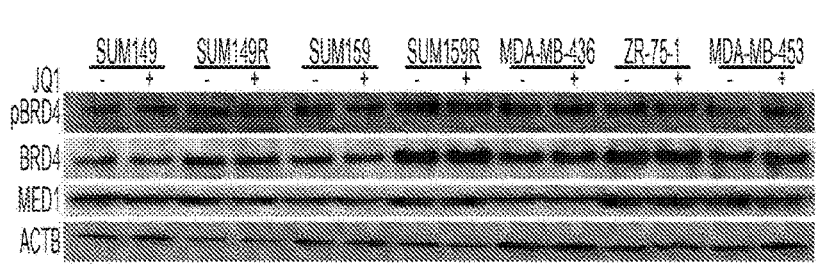
Figure 13C:
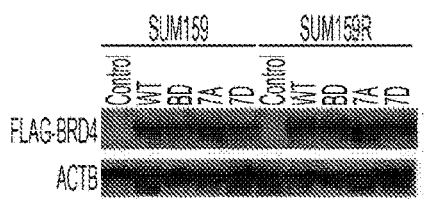

To assess functionally whether increased recruitment of BRD4 to chromatin by MED1 underlies resistance to JQ1, BRD4 expression constructs encoding a bromodomain-inactivated mutant (BDmut) were generated. The ability of these constructs to rescue effects of knock-down of endogenous BRD4 was assessed in stable cell lines (FIGS. 13B-13C). Downregulation of endogenous BRD4 decreased cell growth both in parental SUM159 and in resistant SUM159R cells, which was rescued by enforced expression of wild type BRD4 (FIG. 5D). Expression of BDmut BRD4 failed to rescue parental SUM159 cells, but supported growth of JQ1-resistant SUM159R providing functional validation of the bromodomain-independent recruitment hypothesis (FIG. 5D). Next, the sensitivity of cells expressing BDmut BRD4 to JQ1 were assessed. In parental SUM159 cells exogenously expressed BDmut BRD4 significantly influenced sensitivity to JQ1 (FIG. 5E). In contrast, expression of BDmut BRD4 in SUM159R cells rescued the anti-proliferative effect of JQ1 (FIG. 5F). Together, these studies suggest that BBI resistance is associated with increased binding of BRD4 to MED1, in a bromodomain-independent manner that is not affected by JQ1.

Hyperphosphorylation of BRD4 in BBI Resistance

Figure 6A:
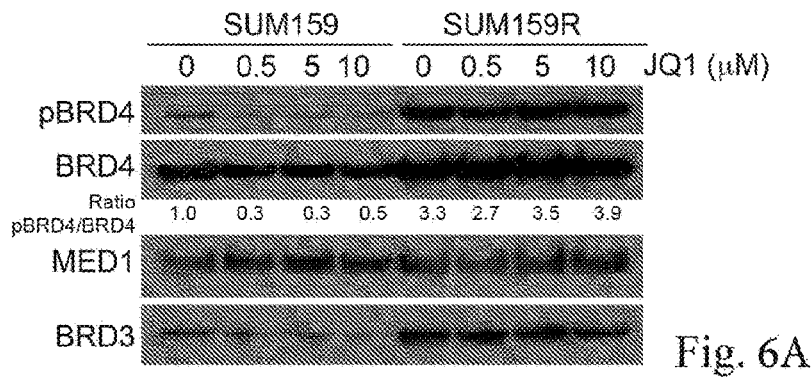
FIGS. 6A-6I. Regulation and relevance of BRD4 phosphorylation.
Figure 6B:
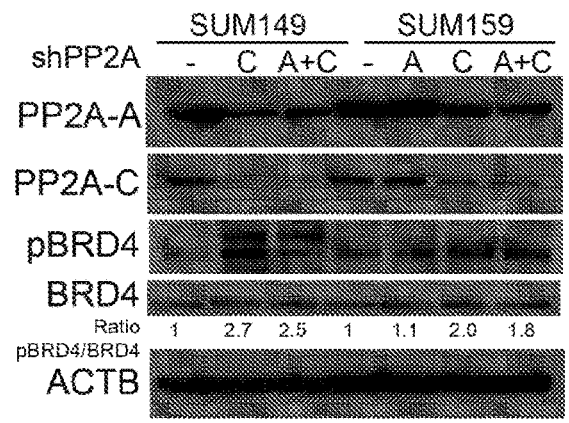
Figure 13E:
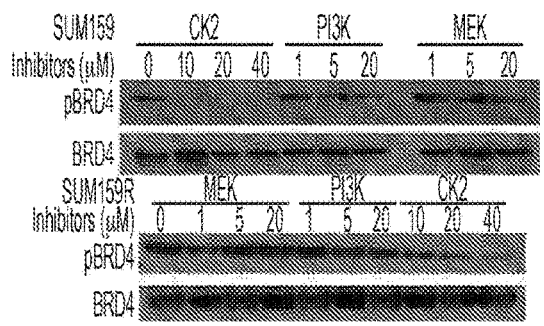

A recent study reported that the stability and nuclear localization of BRD4 is increased with phosphorylation by casein kinase II (CK2)[43]. To explore the contribution of BRD4 phosphorylation to BBI-resistance, immunoblot analysis was performed in parental and resistant cells and found a marked increase of phospho-BRD4 (pBRD4) in resistant cells (FIG. 6A and FIG. 13D). Small-molecule inhibition of CK2 decreased BRD4 phosphorylation in SUM159 and SUM159R cells (FIG. 13E). These results implied that BRD4 is hyperphosphorylated in resistant cells either due to increased phosphorylation by CK2 or, alternatively, due to decreased dephosphorylation by a not-yet-identified BRD4 phosphatase. To investigate these options, first CK2 activity was analyzed in parental and resistant cells by performing pan-CK2 substrate immunoblots. Consistent with prior data describing CK2 as a constitutively active kinase[44], significant differences in CK2 activity between sensitive and resistant cell lines were not detected (FIG. 13F).

Figure 6C:
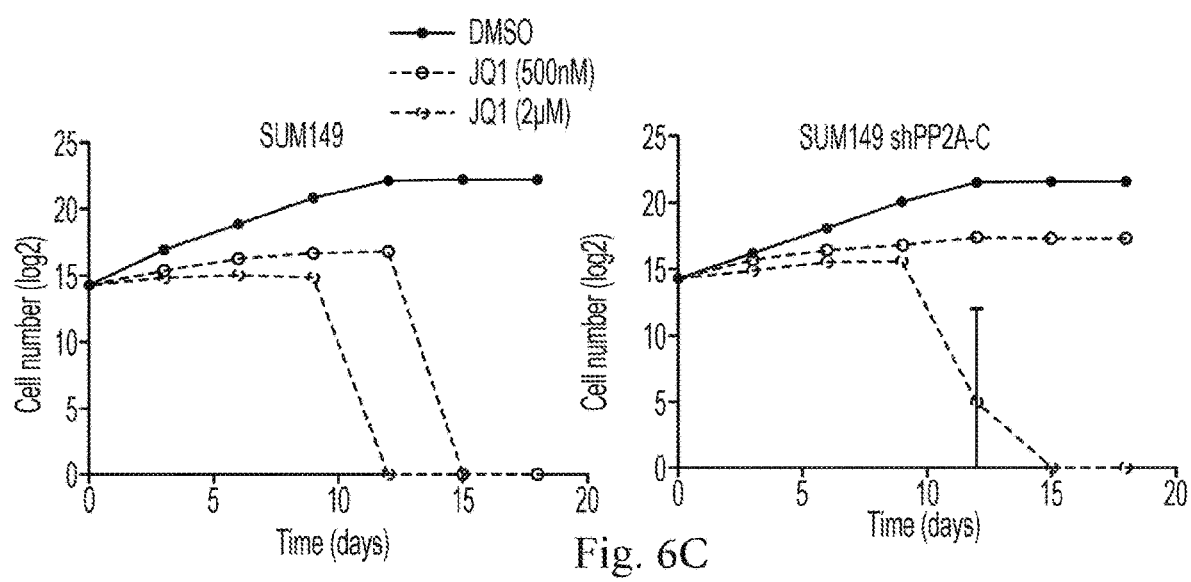
Figure 6D:
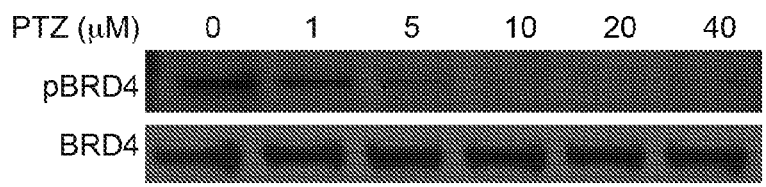
Figure 6E:
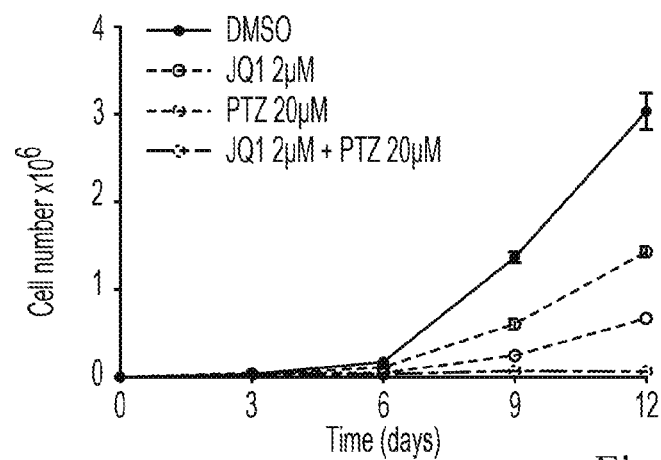
Figure 6F:
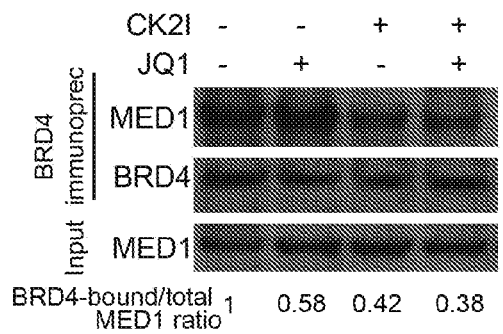
Figure 6G:
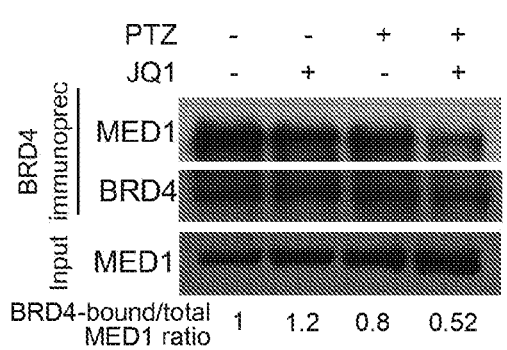

Inactivation of the PP2A tumor suppressor gene has been shown to be a common event in breast cancer and it is associated with therapy resistance and poor prognosis[45]. Further, PP2A is a prolific serine phosphatase that often opposes CK2 function[46,47]. Thus, whether PP2A may be a BRD4 phosphatase and whether decreased PP2A activity could play a role in BBI resistance was investigated. Knockdown of PP2A A and C subunits in SUM149 and SUM159 cells lead to increased BRD4 phosphorylation establishing PP2A as a previously unrecognized BRD4 phosphatase. To strengthen the link between PP2A activity and BBI resistance, the JQ1 sensitivity of SUM149 cells was tested following the knock-down of PP2A C subunit and determined that downregulation of PP2A decreased JQ1 sensitivity (FIG. 6C). A recent study identified phenothiazine compounds as activators of PP2A enzymatic activity[48]. Thus, pBRD4 levels in SUM159R, SUM149R, and other cell lines were analyzed after short-term treatment with phenothiazine (PTZ) and detected rapid dephosphorylation of BRD4 (FIG. 6D and FIG. 13G). In line with this, combined treatment with PTZ and JQ1 overcame BBI resistance in SUM159R cells (FIG. 6E). To investigate the molecular basis by which BRD4 hyperphosphorylation contributes to BBI resistance, whether BRD4 phosphorylation influences MED1 binding was analyzed. Indeed, SUM159R cells treated with CK2 inhibitor or PTZ both lead to decreased MED1 abundance in BRD4 immunoprecipitation experiments, suggesting that pBRD4 binds MED1 more efficiently than BRD4 (FIGS. 6F-6G).

Figure 6H:
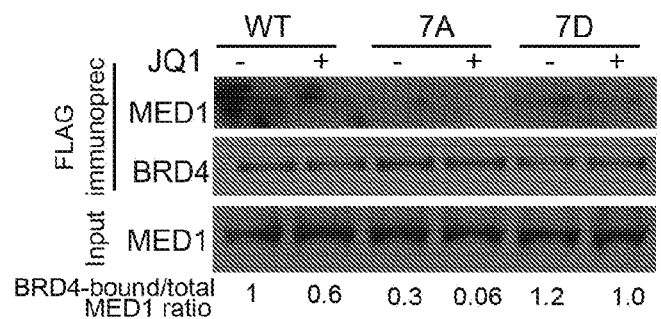

To further, functionally assess the role for BRD4 phosphorylation in BBI resistance and MED1 binding, BRD4 expression constructs encoding mutants that cannot be phosphorylated by CK2 (7 serine to alanine substitutions; "7A mutant") or mimic constitutive phosphorylation (7 serine to aspartate substitutions; "7D mutant") were generated. The ability of these constructs to rescue effects of knock-down of endogenous BRD4 in stable cell lines (FIGS. 13B-13C) were assessed and it was found that expression of 7D mutant supported the growth of both parental SUM159 and JQ1-resistant SUM159R cells, whereas 7A mutant had weaker effect especially in SUM159 cells (FIG. 5D). Next, MED1 binding and subcellular localization of 7A and 7D mutants in the presence and absence of JQ1 was analyzed. The 7A mutant was found to display weaker MED1 binding compared to WT BRD4 and completely dissociates after JQ1 whereas the 7D mutant seems to have higher affinity for MED1 that is not affected by JQ1 treatment (FIG. 6H and FIG. 13H).

Figure 6I:
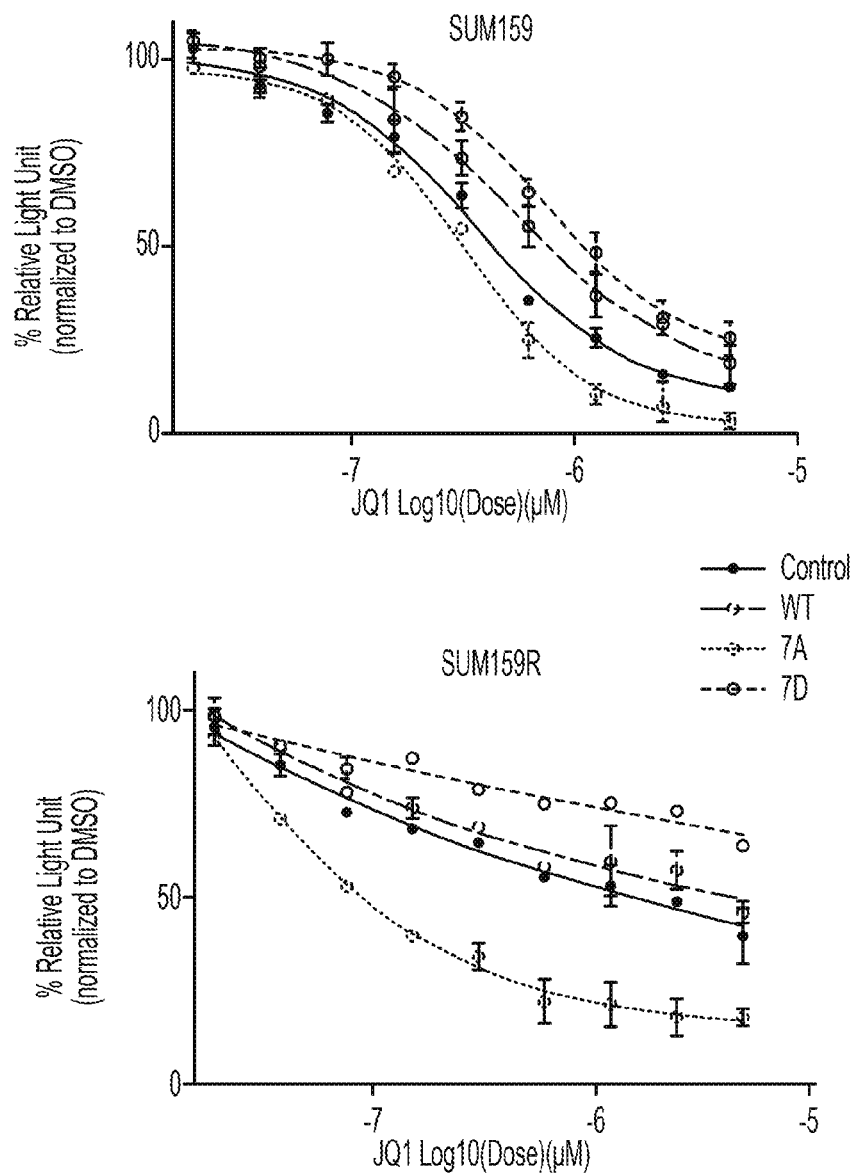

Lastly, the sensitivity of cells expressing 7A or 7D mutant BRD4 to JQ1 was assessed. In parental SUM159 cells exogenously expressed 7D mutant BRD4 decreased sensitivity to JQ1 whereas the 7A mutant slightly increased sensitivity (FIG. 6I). In contrast, expression of 7A mutant BRD4 in SUM159R cells restored JQ1 sensitivity whereas the 7D mutant modestly decreased it even more (FIG. 6I). These results strongly support the hypothesis that hyperphosphorylation of BRD4 due to decreased PP2A activity in BBI resistant cells leads to increased recruitment of BRD4 to MED1 and decreased responsiveness to BBIs.

Figure 14A:
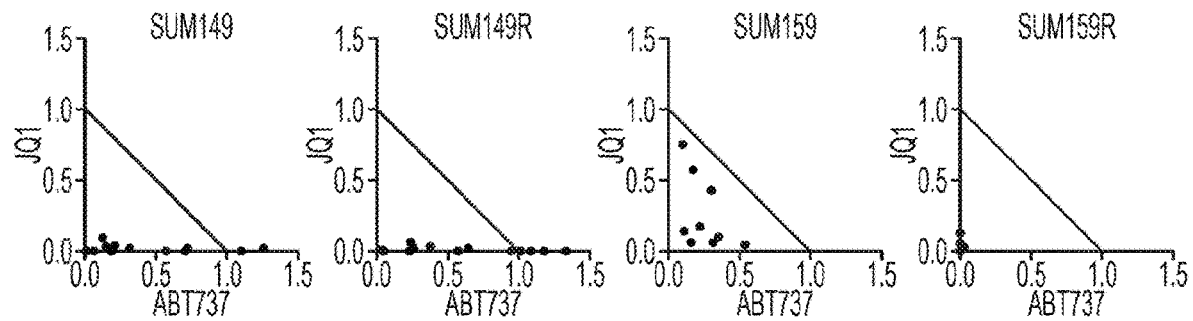
FIGS. 14A-14C. Overcoming BBI resistance.
Figure 14B:
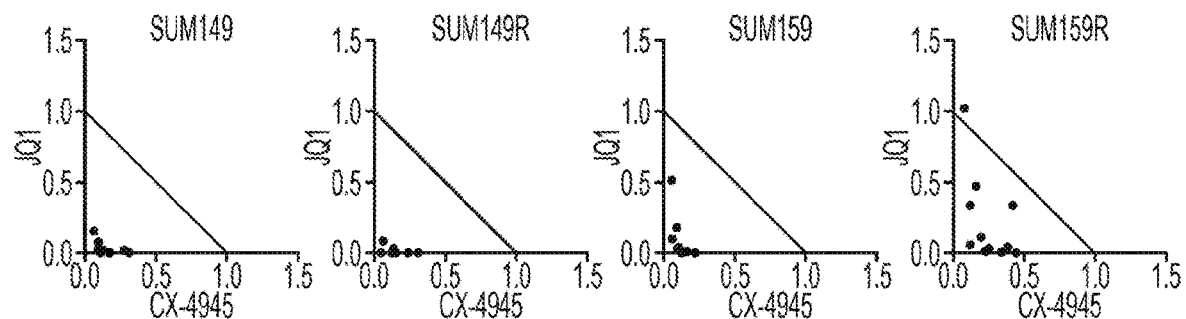
Figure 14C:
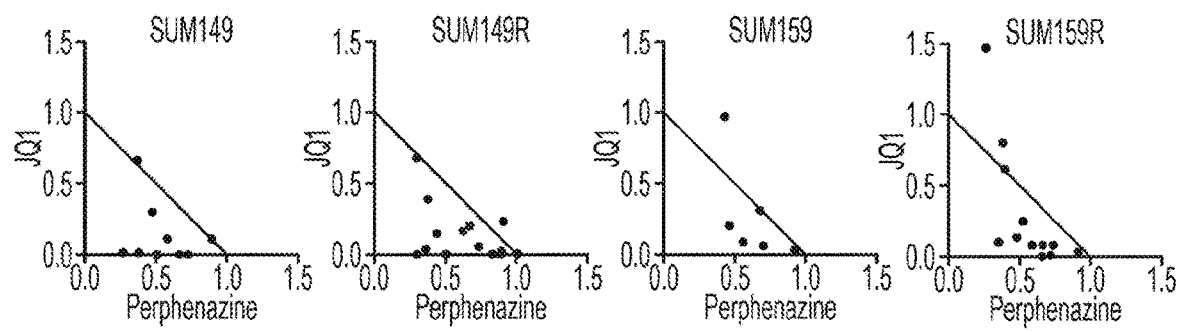

To extend the translational relevance of the findings, synergy screens were conducted with JQ1 and molecules targeting BCL-XL (ABT737), a gained super-enhancer in SUM159R cells, and modulators of BRD4 phosphorylation, a CK2 inhibitor CX-4945, and PP2A activator perphenazine (PPZ). Significant synergy was observed between JQ1 and ABT737, CX-4945, and also PPZ (FIG. 14) implying that these drug combinations will likely achieve even higher efficacy in TNBCs than BBIs alone.

Figure 15A:
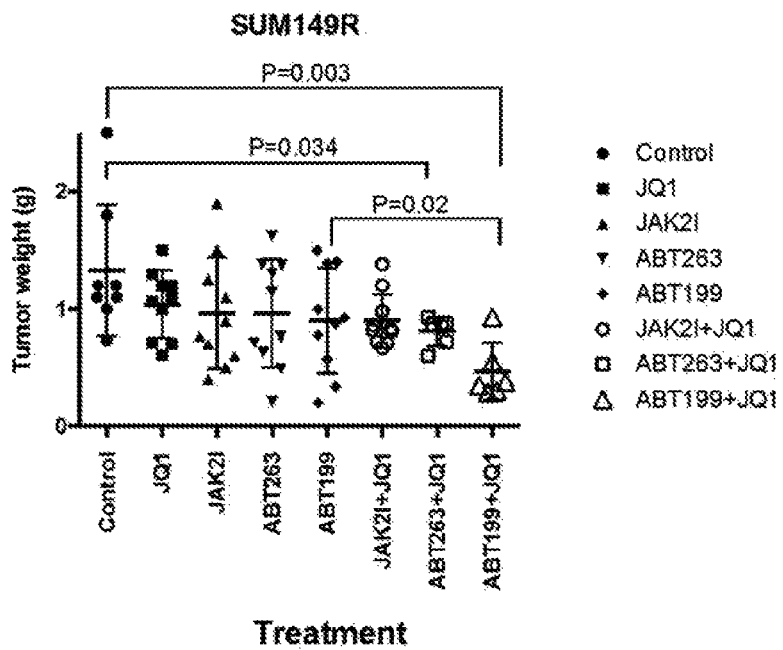
FIG. 15A and FIG. 15B. Effects of BBI combination therapies on tumor weight of xenografts derived from BBI-resistant cells. Tumor-bearing mice, having tumors derived from either SUM149 cells (FIG. 15A) or SUM159 cells (FIG. 15B), were administered vehicle (control), single therapy (JQ1, JAK2I, ABT 263, or ABT 199), or BBI combination therapy (JAK2I+JQ1, ABT 263+JQ1, or ABT 199+JQ1).
Figure 15B:
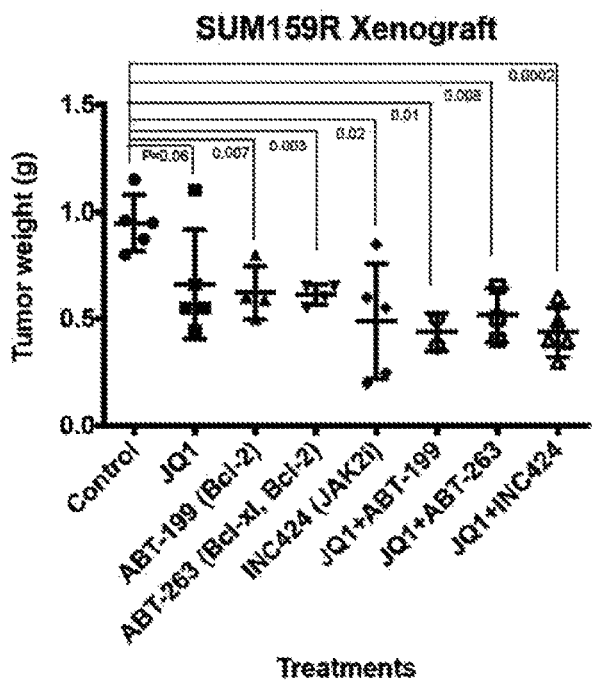

Further to the synergy screening experiments, the effects of different BBI combination therapies on tumors derived from BBI-resistant cells were examined. Mice bearing tumors derived from BBI-resistant SUM149 cells (FIG. 15A) or tumors derived from BBI-resistant SUM159 cells (FIG. 15B) were administered vehicle, single therapy, or BBI combination therapy. Single therapies consisted of administering a BET inhibitor (JQ1), a JAK2 inhibitor (INC424, or "JAK2I"), a Bcl-xl/Bcl-2 inhibitor (ABT 263), or a Bcl-2 inhibitor (ABT 199). Combination therapies consisted of administering JQ1 along with either INC424, ABT 263, or ABT 199. In both xenograft models, each BBI combination therapy reduced tumor weight to a greater extent than the corresponding single therapy and JQ1 alone.

Figure 16A:
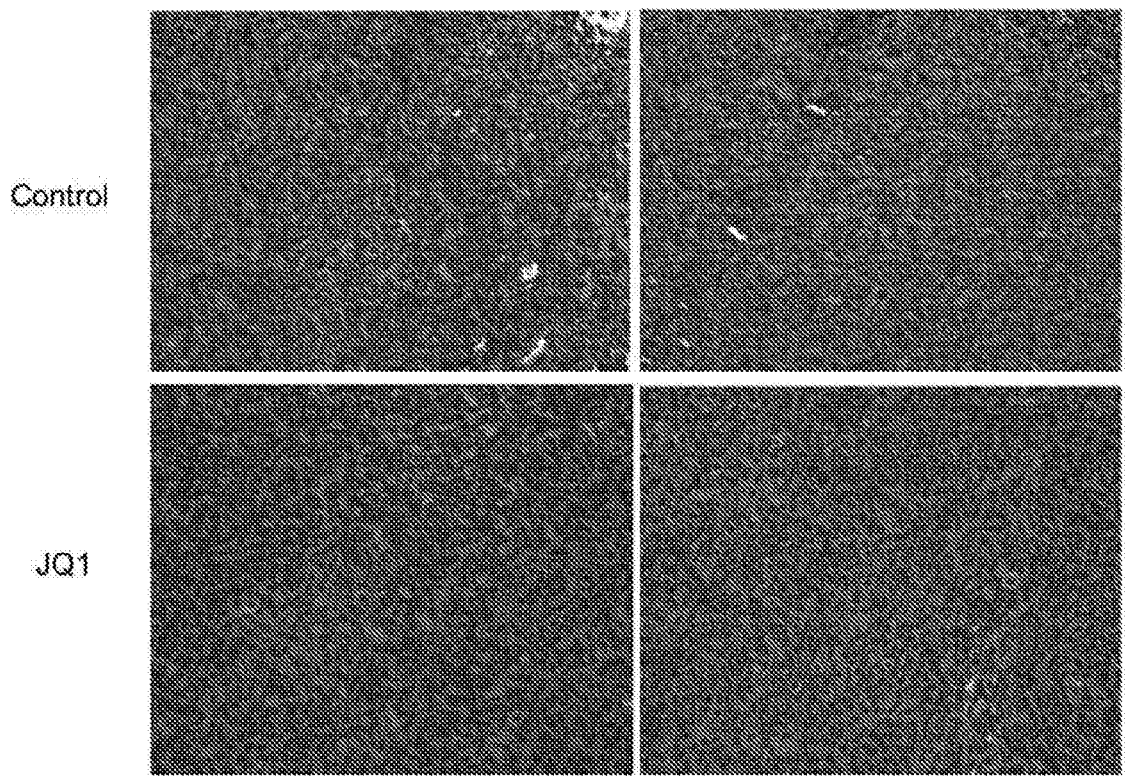
FIGS. 16A-16D. H&E staining of BBI-resistant SUM159 xenografts treated with vehicle, single therapy, or BBI combination therapy. Images were obtained from tumor-bearing mice having tumors derived from SUM159R cells and treated with vehicle as a control (FIG. 16A, top panels), JQ1 (FIG. 16A, bottom panels), ABT 199 (FIG. 16B, top panels), ABT 263 (FIG. 16B, bottom panels), INC 424 (FIG. 16C, top panels), ABT 199+JQ1 (FIG. 16C, bottom panels), ABT 263+JQ1 (FIG. 16D, top panels), INC 424+JQ1 (FIG. 16D, bottom panels).
Figure 16B:
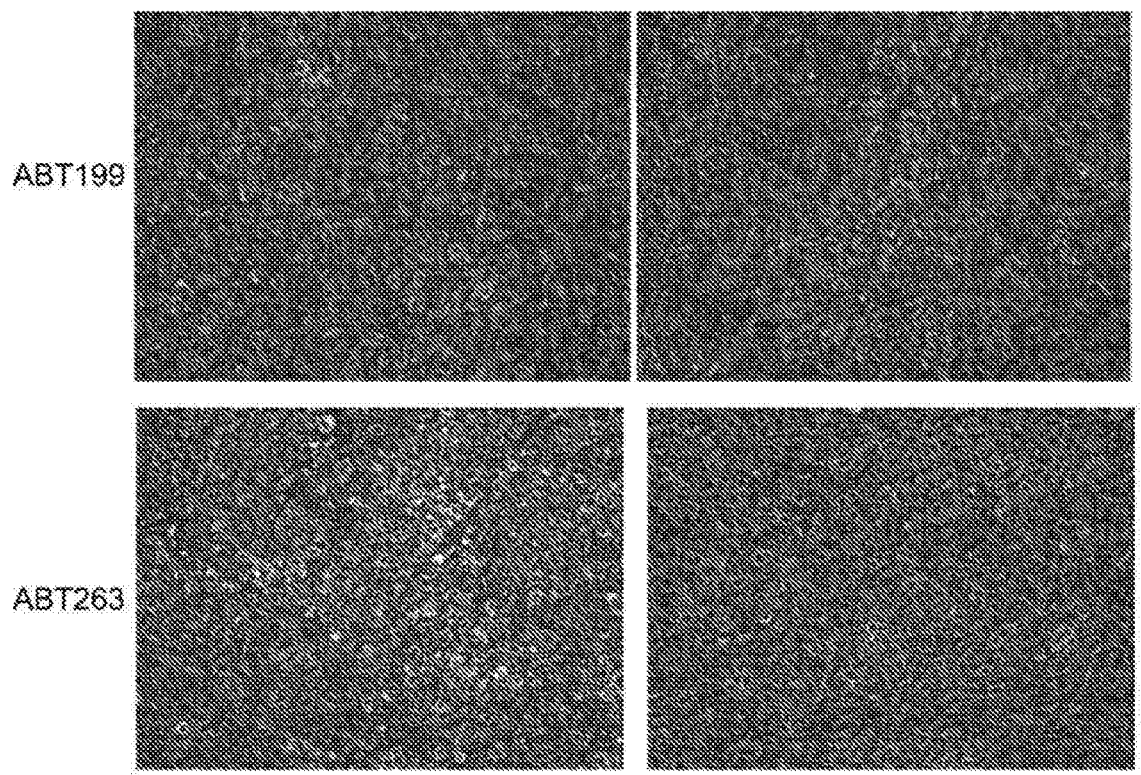
Figure 16C:
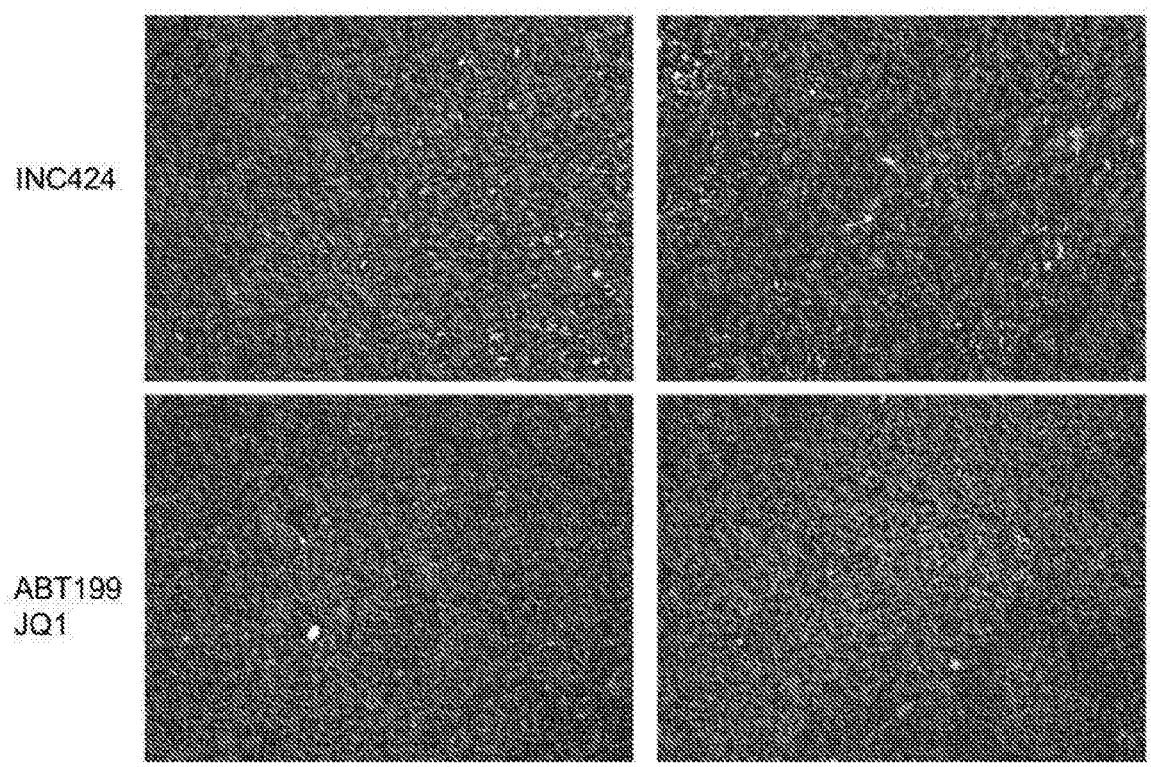
Figure 16D:
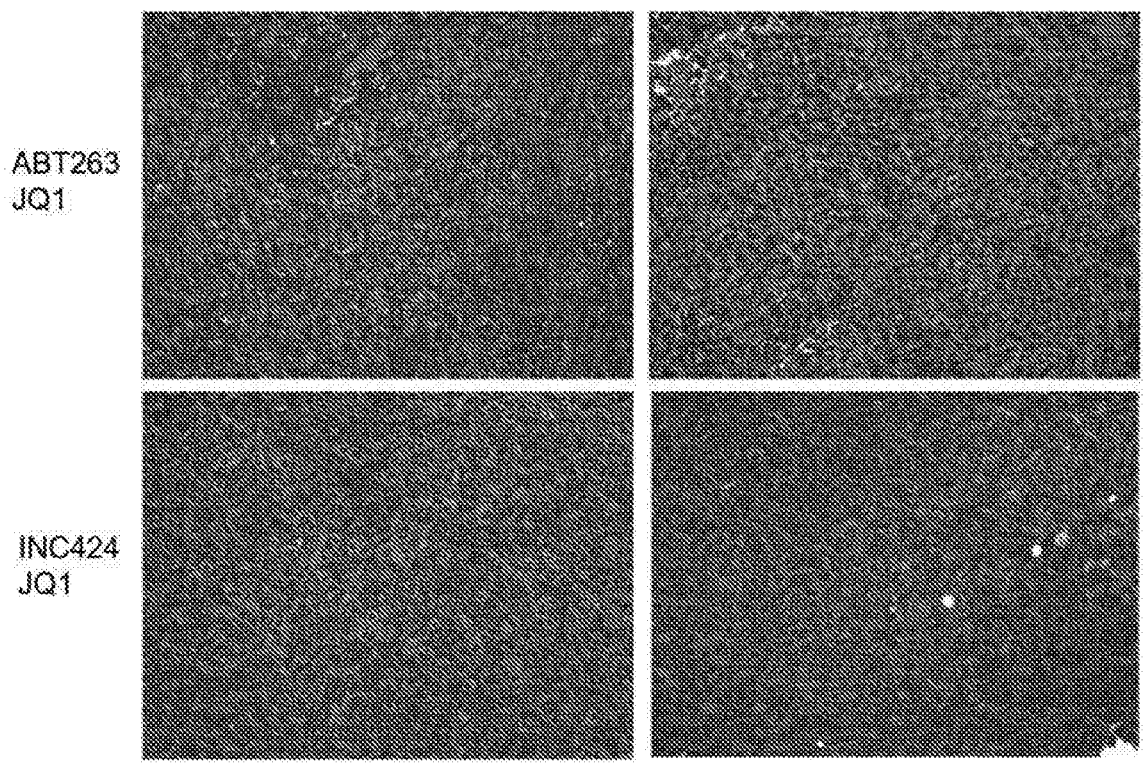

The xenografts derived from BBI-resistant SUM159 cells (SUM159R) were subjected to H&E staining after treatment with vehicle as a control (FIG. 16A, top panels), JQ1 (FIG. 16A, bottom panels), ABT 199 (FIG. 16B, top panels), ABT 263 (FIG. 16B, bottom panels), INC 424 (FIG. 16C, top panels), ABT 199+JQ1 (FIG. 16C, bottom panels), ABT 263+JQ1 (FIG. 16D, top panels), INC 424+JQ1 (FIG. 16D, bottom panels). As depicted, the cellularity of the combination treatments was significantly decreased relative to the corresponding single therapies. Taken together, the above results confirm that certain combination therapies achieve higher efficacy in TNBCs than BBIs alone.

Figure 17:
FIG. 17. Cellular fluorescence imaging of BBI-sensitive and BBI-resistant SUM159 xenografts stained with Bcl-xl mouse antibody. Xenografts derived from BBI-sensitive SUM159 cells (top) and BBI-resistant SUM159 cells (bottom) were stained to determine the relative presence of Bcl-xl.
Figure 17:
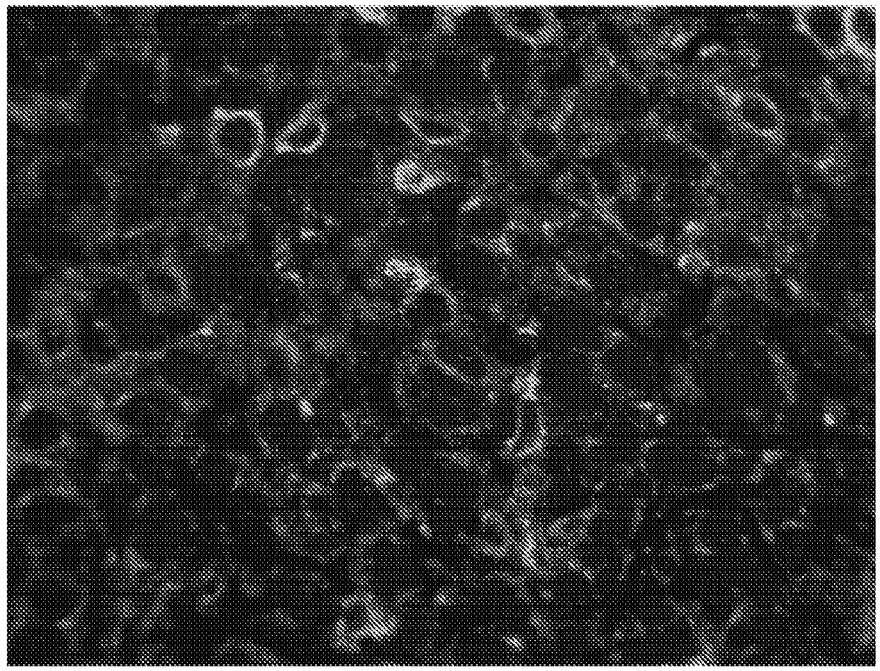

To further investigate the role of Bcl-xl in BBI resistance, parental SUM159 cells (BBI-sensitive) and SUM159R cells (BBI-resistant) from xenografts were stained for Bcl-xl by staining with mouse Bcl-xl antibody (1:50, overnight). Fluorescence imaging indicated that Bcl-xl was present to a far greater extent in BBI-resistant SUM159 cells (FIG. 17, bottom) than in BBI-sensitive SUM159 cells (FIG. 17, top). This evidence is consistent with the postulate that an overexpression of Bcl-xl, an anti-apoptotic protein, may be a contributing factor to BBI resistance.

Discussion

Triple negative breast cancer is the only major breast tumor subtype that lacks effective, targeted therapies[4]. Although a subset of early-stage TNBC patients responds well to chemotherapy, the majority recurs rapidly with metastatic disease for which treatment options are limited. Thus, novel therapeutic strategies are urgently needed. TNBC cancer genome sequencing studies failed to identify genetic alterations that could be explored for therapies[2] necessitating the search for non-genetic targets as unrecognized dependencies. A rationale for BET inhibition is identified in TNBC in anticipation of a firm understanding of core regulatory circuitry.

BET inhibition has demonstrated efficacy in disparate models of cancer in a rapidly expanding literature. Despite apparent resistance in the vast majority of these reports, as observed here in TNBC, mechanisms of BET inhibitor resistance have not been reported. Integrating approaches in epigenomics, proteomics and chemical biology, an example of epigenetic drug resistance by epigenetic mechanism is provided, where BRD4 is recruited to chromatin in a bromodomain-independent manner due to increased binding to MED1 due to its hyperphosphorylation as a consequence of decreased PP2A activity in resistant cells. This research demonstrates combination strategies to anticipate and overcome BBI resistance, such as pairing with BCL-xL inhibitors (e.g., ABT-737) or CK2 inhibitors, and guides the development of second-generation BET inhibitors that disrupt BET function via orthogonal biophysical or biochemical actions. More immediately, the robust efficacy observed in pre-clinical models supports the development of BET inhibition in TNBC alone, and in combination with mechanism-based targeted therapies.

Materials and Methods

Cell Lines and Breast Tumor Tissues

Breast cell lines were obtained from the ATCC and Dr. Steve Ethier, University of Michigan, Ann Arbor, Mich.

(SUM series). Cells were cultured in media recommended by the provider, their identity confirmed by STR analysis, and regularly tested for *mycoplasma*. Breast tumor samples were collected using protocols approved by the DF/HCC Institutional Review Board. Tumors were minced with razor blades and digested with stirring for 3-4 hours at 37° C. in DMEM/F12 with 2 mg/mL BSA, 2 mg/mL collagenase type IV, and 2 mg/mL hyaluronidase. After digestion, cells were filtered through 500-micron mesh, washed in DMEM/F12 with 5% FBS, frozen in DMEM/F12 with 5% FBS and 10% DMSO, and stored in liquid nitrogen for subsequent xenograft studies.

High-Throughput Screening of BET Bromodomain Inhibitors in Breast Cell Line Panel A panel of compounds (synthesized in the Bradner lab) was tested in 29 human breast cell lines in a 384-well format at 2,000 cells per well using a semi-automated screen essentially as described[8]. Cell viability at 72 hr was evaluated using ATPlite (Perkin Elmer).

Synergy Studies

SUM149, SUM149R, SUM159, and SUM159R cells were seeded in sterile, white, opaque 384-well microtiter plates (Thermo), using an automated dispensing system (BioTek EL406), at 1,000 cells per well in 50 µl of media. Drugs were delivered in DMSO by robotic pin transfer with a JANUS workstation (100 nl) to achieve a matrix of pairwise dose-response incubations of each compound, each pair having eight replicates. Following 72 hours of incubation, ATP levels were determined for treated cells and vehicle controls (ATPlite, PerkinElmer). Data were normalized to vehicle controls. Combination indices were determined using the median-effect principle of Chou and Talalay[49] (CalcuSyn Software). Isobologram plots were generated with GraphPad Prism software. Points represent paired values of drug concentrations assessed for synergism. The diagonal line signifies drug additivity. Points above the line represent antagonistic drug combinations, and those below the line represent synergistic drug combinations. Synergy assays were performed in triplicates and repeated 2-3 times.

Xenograft Assays

For xenograft assays 5-6-weeks old female CrTac:NCr-Foxn1$^{nu}$ and NOD.Cg-Prkdc$^{scid}$ Il2rg$^{tm1Sug}$/JicTac mice were purchased from Taconic. Tumors were induced by bilateral orthotopic mammary fat pad injection of 1×10$^6$ cells in 50% Matrigel (BD Biosciences) in DMEM/F12 or Medium 171 (except for IDC50-X cells, which were injected with 3% FBS and 4 mg/ml collagen gel in Medium 171). Animal experiments were conducted following protocol 11-023 approved by the Dana-Farber Cancer Institute Animal Care and Use Committee. For all the xenograft studies, the sample size of each group (5-10 mice) is indicated in the figures.

Cellular Viability, Senescence, and MDR Assays

Cell viability and growth assays (FIGS. 1A-1B, FIGS. 3A-3E, 3G, FIGS. 5D-5F, FIGS. 6C, 6E, 6I, FIG. 7A, FIG. 10D, FIGS. 14A-14C), cycle, apoptosis, and MDR assays were performed in triplicates and repeated 2-3 times. For cell proliferation assays, cells were plated at 500 cells per well in 96-well plates and treated the next day with inhibitors, DMSO or doxycycline (500 ng). Cells were cultured at 37° C. with 5% CO2 in the media described-above, and cell viability was measured using CellTiter-Glo three days after treatments. For cell growth assays, cells were plated at 5000 (SUM159) or 20000 (SUM149) cells per well in 6-well plates and treated the next day with inhibitors. Cells were counted every three days by cell counter. Cellular apoptosis was analyzed with an APC AnnexinV/7ADD Apoptosis Detection kit (BD Pharmingen). AnnexinV/7AAD assessments and cell cycle graphics were generated using FlowJo software V7.6.1 for Windows (Tree Star). Senescence Beta-gal staining was performed using Senescence β-Galactosidase staining kit from Cell signaling. Briefly, after JQ1 treatment (500 nM) for 72 h, SUM159 and MDA-MB-231 cells were fixed by Fixative Solution for 15 min, followed by β-Galactosidase solution incubation overnight at 37° C. The staining was checked under microscope for the development of blue color. Multi-Drug Resistance Assay was performed with MDR assay kit from Cayman Chemical (600370). Briefly, SUM159 and SUM159R cells were treated with JQ1 or DMSO for 30 min in SUM medium. Verapamil was used as a positive control at 1:1000 dilution. Calcein AM/Hoechst Dye staining solution was added after that and cells were incubated at 37° C. for 15 min. The cells were analyzed by fluorescent microscope and FACS.

Cell cycle analysis was performed 72 hr after JQ1 treatment or BRD4 downregulation with doxycycline using propidium iodide (PI) staining. Cells were resuspended in 1 ml of growth medium supplemented with 2 µg/ml PI (Life Technologies) as final concentration. After 60 min at 37° C. in the dark, analysis was performed on a FACS AriaII cytometer (BD Biosciences). The cell cycle was plotted as histogram after excluding doublets. Cell synchronization Procedure. SUM159 cells were treated with nocodazole (200 ng/ml) for 12 h and then cells were tapped to detach from the plates. After washing twice with PBS, cells were replated with or without JQ1 in collagen coated plates. Cells were collected at 0, 3, 6, 12 h time point for FACS and immunoblot analysis.

Immunofluorescence Staining

Antibodies used for immunofluorescence were CK18 (Dako, M7010), CK17 (Dako, M7046), HMW (Dako, M0630), LMW (Dako, M0631), CD44 (NeoMarkers, MS-668-P1), CD24 (NeoMarkers, MS-1279-P1), p-STAT3 (Cell Signaling, 9145S), VIM (Dako, M073501), CDH1 (BD Biosciences, 610181), FLAG (Sigma, F1804), BrdU (Roche, 11170376001). Immunofluorescence experiments were performed in cultured cells or in whole sections of formalin-fixed paraffin embedded (FFPE) xenograft tumors. The staining was performed as described[50]. Antibody dilutions were as follows: pSTAT3 (1:25), CD44 (1:100), CD24 (1:100), CK18 (1:200), CK17 (1:200), HMK (1:200), LMK (1:200), VIM (1:100), CDH1 (1:100), FLAG (1:50), and BrdU (1:200).

siRNAs and Lentiviral shRNA and Expression Constructs

For siRNA transfection cells were plated at 2,000 cells per well in 96-well plates and cultured at 37° C. with 5% CO2 in the media. The next day, cells were transfected in triplicate with siGENOME SMARTpools for the genes of interest or "Non-Targeting siRNA" controls using DharmaFECT I (Dharmacon). The sequences of the siRNAs in the SMARTpools are listed in Table 2. Cell viability was measured using CellTiter-Glo (Promega) three days after transfections, with the effects of each siRNAs treatment on each cell line compared to the effects of no siRNAs.

TET-inducible pLKO-TET-ON lentiviral constructs were packaged by co-transfection of the lentiviral hairpin containing plasmid PLKO.1 and the helper plasmids pCMV-dR8.91 and pMD2.G-VSV-G into HEK293T cells using Lipofectamin (Life Technologies). Following transduction via spinoculation for 30 min hr at 1000 g and selection with 1 µg/ml puromycin for 72 hr (Sigma, St. Louis, Mo.), knockdown efficacy was determined by western blotting and cells were seeded for proliferation assays as described above. Sequences of shRNAs used are listed in Table 2.

Full length BRD4 in pCDNA3 was a gift from Dr. French at Brigham and Women's Hospital, Harvard Medical School. Mutations of BRD4 BD1 (N140A) and BD2 (N433A) bromodomains, 7A and 7D mutants were generated using a Quickchange Multi Site-Directed Mutagenesis Kit (Agilent Technologies) using primers listed in Table 2 and subsequently verified by sequencing.

Immunoblotting and Immunoprecipitation Experiments

Cells were lysed five days after transfection with siRNAs in RIPA buffer. Proteins were resolved in SDS-polyacrylamide gels (4%-12%) and transferred to PVDF membranes by using a Tris-glycine buffer system. Membranes were blocked with 5% milk powder in 0.1% Tween20 in PBS (PBS-T) for 1 hr at room temperature followed by incubation with primary antibodies at 1:1000 dilution in 2.5% milk PBS-T. For immunoprecipitation, nuclear extracts were prepared as follow: $10\times10^6$ cells were resuspended in 5 ml Buffer A: 10 mM Tris pH 7.9, 1.5 mM MgCl2, 10 mM KCl, 0.05% NP-40, 1 mM DTT, and protease and phosphatase inhibitors. Cells were incubated on ice for 15 min and gently vortexed every 5 min. After centrifugation at 2,000 g for 5 min, pellets were suspended in 0.3 ml buffer B (20 mM Tris pH 7.9, 25% glycerol, 0.42 M NaCl, 1.5 mM MgCl2, 1 mM KCl, 0.5% NP40, 0.2 mM EDTA, 1 mM DTT, and protease and phosphatase inhibitors) and incubated for 5 min on ice. After centrifugation of the lysates at 14 g for 10 min at 4° C., supernatant was diluted with 0.6 ml buffer A, and added NP-40 to final 0.5% and treated with DNase I. The samples were then incubated at 4° C. overnight with BRD4 or Flag antibodies at 1:100 dilution and immunoprecipitates were collected on Dynabeads Protein G for 2 hr. Beads were washed with buffer B containing 150 mM NaCl and 0.5% NP-40 three times and then resuspended in gel loading buffer. Immunoblotting and immunoprecipitation experiments were repeated 2-3 times.

Antibodies and Inhibitors

Antibodies used for immunoblotting, immunoprecipitation and Chip-seq were as follows: BRD4 (Bethyl, A301-985A), MED1 (Bethyl, A300-793a), BRD3 (Bethyl, A302-368A), BRD2 (Bethyl, A302-583A), MYC (Santa Cruz, sc764), p-STAT3 (Cell Signaling, 9145S), STAT3 (Cell Signaling, 4904), p-STAT5 (Cell Signaling, 9351), p-JAK2 (Cell Signaling, 3771), CYCLIN D1 (Cell Signaling, 2922), p-H3 (Cell Signaling, 12201), CK2 substrate (Cell signaling, 8738), PP2A-A (Cell signaling, 2039), PP2A-C(Cell signaling, 2038) and p-BRD4 was a gift from Dr. Chiang at University of Texas Southwestern Medical Center. Antibodies used for ChIP-seq were BRD4 (Bethyl) Histone H3K27ac (Abcam, ab4729). CXCR2 inhibitor (239819) and CK2 inhibitor (218860) were from CalBiochem, JAK2 inhibitor (INC424), MEK inhibitor (GSK1120212, S2673) and PI3K inhibitor (BKM120, S2247) were from Selleckchem, Phenothiazine (1525707) and perphenazine (1511000) was from Sigma, ABT-737 (s1002) was from Selleckchem.

SILAC-RIME Experiments and Data Analysis

SUM159 and SUM159R cells were grown in R/K-deficient SILAC DMEM (paa; E15-086), 10% dialyzed serum (Sigma-Aldrich; F0392), and supplemented with 800 μM L-Lysine $^{13}C_6^{15}N_2$Hydrochloride and 482 μM L-Arginine$^{13}C_6^{15}N_4$ hydrochloride (Cambridge Isotope lab) for "heavy"-labeled media or 800 μM L-Lysine $^{12}C_6^{14}N_2$-Hydrochloride and 482 μM L-Arginine $^{12}C_6^{14}N_4$ hydrochloride for "light"-labeled media. After SILAC labeling, RIME was performed as described[42].

In Vitro Chem-Seq, ChIP-Seq, and RNA-Seq

Chem-seq was performed essentially as described[27]. ChIP-seq: SUM159 and SUM159R cells ($4\times10^7$) were grown in SUM Medium. The media were then removed and replaced with media containing 1% formaldehyde (EM grade; tebu-bio) and crosslinked for 8 min. Crosslinking was quenched by adding glycine to a final concentration of 0.2 M. The cells were washed with ice-cold PBS, harvested in PBS, and the cell pellet was washed with PBS. The nuclear fraction was extracted by first resuspending the pellet in 10 ml of LB1 buffer (50 mM HEPES-KOH [pH 7.5], 140 mM NaCl, 1mMEDTA, 10% glycerol, 0.5% NP-40 or Igepal CA-630, and 0.25% Triton X-100) for 10 min at 4° C. Cells were pelleted, resuspended in 10 ml of LB2 buffer (10 mM Tris-HCL [pH 8.0], 200 mM NaCl, 1 mM EDTA, and 0.5 mM EGTA), and mixed for 5 min. Cells were pelleted and resuspended in 300 μl of LB3 buffer (10 mM Tris-HCl [pH 8], 100 mM NaCl, 1 mM EDTA, 0.5 mM EGTA, 0.1% Na-deoxycholate, and 0.5% N-lauroylsarcosine) and sonicated in a covaris sonicator for 10 min. A total of 30 μl of 10% Triton X-100 was added, and lysate was centrifuged for 10 min at 20,000 rcf to purify the debris. The supernatant was then incubated with 100 μl of magnetic beads (Life Technologies) prebound with 20 μg BRD4 antibody (Bethyl, A301-985A), and immunoprecipitation (IP) was conducted overnight in the cold room. The beads were washed ten times in 1 ml of RIPA buffer and twice in 100 mM ammonium hydrogen carbonate (AMBIC) solution. DNA was eluted in elution buffer (50 mM Tris-HCl pH 8, 10 mM EDTA, and 1% SDS). Cross-links were reversed overnight at 65° C. RNA and protein were digested with 0.2 mg/mL RNase A for 2 hr followed by 0.2 mg/mL Proteinase K for 1 hr. DNA was purified with phenol chloroform extraction and ethanol precipitation. Libraries for Illumina sequencing were prepared following the Rubicon ThruPLEX-FD kit for 10-12 cycles.

RNA-seq: SUM159 and SUM159R were incubated in biological duplicates for 3, 12 and 24 hr with 500 nM of JQ1 or DMSO treatment. Total RNA was extracted using the standard QIAGEN RNeasy kit (74106). RNA concentrations were measured and quality controlled on a Bioanalyzer, RNA-Seq libraries were made using Illumina True-Seq RNA kits using the Sciclone NGSx workstation.

All RNA-seq and ChIP-seq experiments (FIGS. 2, 4, 9 and 12) were performed in duplicates.

Genomic Data Analyses

Accessing data generated in this manuscript. All ChIP-seq, Chem-seq, and RNA-seq data generated in this publication can be found online associated with GEO Publication Reference ID GSE63584 (www.ncbi.nlm.nih.gov/geo/). Gene sets and annotations. All analysis was performed using RefSeq (NCBI37/HG19) human gene annotations.

RNA-seq data processing and gene expression quantification. All RNA-Seq datasets were aligned to the transcriptome using Tophat2[52] (version 2.0.11) using the Illumina igenomes NCBI37/HG19 UCSC transcriptome build retrieved from ccb.jhu.edu/software/tophat/igenomes.shtml. Alignments were performed using default parameters. Transcript expression quantification was performed using Cufflinks[53] (version 2.2.0) with default parameters to generate gene expression values in units of FPKM.

ChIP-seq and Chem-seq data processing. All ChIP-seq and Chem-seq datasets were aligned using Bowtie2[54] (version 2.2.1) to build version NCBI37/HG19 of the human genome or build version NCB37/MM9 of the mouse genome. Alignments were performed using the following criteria: –k 1, with all other parameters set to default. These criteria preserved only reads that mapped uniquely to the genome without any mismatches.

Calculating read density. The normalized read density of a ChIP-seq or Chem-seq dataset was calculated in any region using the Bamliquidator (version 0.9) read density calculator (github.com/BradnerLab/pipeline/wiki/bamliquidator). Briefly, ChIP-Seq reads aligning to the region were extended by 200 bp and the density of reads per basepair (bp) was calculated. The density of reads in each region was normalized to the total number of million mapped reads producing read density in units of reads per million mapped reads per bp (rpm/bp).

Identifying ChIP-seq and Chem-seq enriched regions. The MACS version 1.4.2 (Model based analysis of ChIP-Seq)[55] peak finding algorithm was used to identify regions of ChIP-Seq enrichment over background. A p-value threshold of enrichment of 1 e-9 was used for all datasets.

Creating heatmap representations of ChIP-seq occupancy. Heatmaps of ChIP-seq occupancy for various factors were created as described[56]. Heatmaps were created for the +/−10 kb region flanking all transcription start sites (TSS) or for the +/−10 kb region flanking all TSS distal BET bromodomain bound enhancers. Each row plots a specific TSS or enhancer region. Rows are ranked by peak occupancy of BET bromodomains as determined by Bio-JQ1 Chem-seq signal (FIG. 2A).

Correlating BRD4 and H3K27ac occupancy to Bio-JQ1. Occupancy of BRD4 and H3K27ac was correlated to Bio-JQ1 occupancy at all regions of Bio-JQ1 enrichment in SUM159 cells. Pearson correlation statistics are shown (FIG. 2B). To quantify changes in BRD4 or H3K27ac occupancy upon JQ1 treatment, all Bio-JQ1 enriched regions were ranked in SUM159 cells and then binned (n=10). Corresponding boxplots of BRD4 or H3K27ac log 2 fold change+/−JQ1 are shown for each bin (FIG. 2D).

Mapping enhancers and super-enhancers using Bio-JQ1 occupancy or BRD4. Enhancers and super enhancers (SEs) were mapped using the ROSE software package described[16, 17] and available at (younglab.wi.mit.edu/super_enhancer_code.html). In SUM159 and SUM159R cells, Bio-JQ1 Chem-Seq enriched regions were used to map enhancers and SEs (FIG. 2E). In SUM149 cells, BRD4 ChIP-seq enriched regions were used to map enhancers and SEs (FIGS. 9A-9G).

Quantifying changes in gene expression of SE proximal genes. Genes within 50 kb of SE in SUM159 or SUM149 were identified and filtered for expression status (>1 FPKM expression in any sample), and filtered to remove non poly-adenylated transcripts (e.g. microRNAs). For SUM159, $log_2$ fold changes in gene expression at SE associated genes or all expressed genes was compared at 3, 12, and 24 hours post JQ1 treatment (FIG. 2F). For SUM149, comparisons were made at 12 hours post JQ1 treatment (Extended Data FIG. 3B). The statistical significance of differences between distributions of changes was also assessed using a Welch's two-tailed t test.

Identifying differentially expressed genes upon JQ1 treatment. To identify genes differentially regulated by JQ1 treatment in SUM159 or SUM149 cells, all genes with a >$log_2$ fold change in expression were ordered by fold change at 24 hours+/−JQ1 for SUM159 or at 12 hours+/−JQ1 for SUM149. The $log_2$ row median normalized fold change for each gene is displayed in FIGS. 4H-4I for SUM159 and in FIG. 9D for SUM149. For subsequent gene set and pathway analysis, SUM159 genes with consistent and statistically significantly altered expression were selected using a Welch's two-tailed t test between DMSO and JQ1 treated expression values at 12 and 24 hours.

Identifying gained/lost SE between SUM159 and SUM159R. SE differential regions were defined as in Brown et al. 2014[26]. Briefly, in order to quantify changes in super-enhancers between two conditions, background subtracted ChIP-Seq signal was calculated at the set of all enhancer regions considered super in at least one condition. Gained/lost super-enhancers were determined as those with a greater than $log_2$ fold change signal in either direction. The $log_2$ fold change in Bio-JQ1 occupancy at all rank ordered SE containing regions is shown in FIG. 4A. SE regions were classified as either gained, conserved, or lost. Gained/lost regions were classified as those with >1 $log_2$ fold change in either direction. Conserved regions were classified as those with <0.25 $log_2$ fold change in either direction. The $log_2$ fold change in either BRD4 or proximal (within 50 kb of region) gene expression is shown in FIGS. 4B-4C.

Quantifying changes in BRD4 and H3K27ac occupancy upon JQ1 treatment in either SUM159 or SUM159R cells at Bio-JQ1 regions. $Log_2$ fold changes in BRD4 or H3K27ac were quantified at Bio-JQ1 enriched regions in their respective cell line and shown in FIGS. 4F-4G.

Quantifying changes in BRD4 and H3K27ac as a function of Bio-JQ1 or BRD4 occupancy. Bio-JQ1 enriched regions in SUM159 or BRD4 enriched regions in SUM149 were ranked by increasing levels and then distributed into 10 bins. $Log_2$ fold changes in BRD4 or H3K27ac were quantified in each bin of regions and displayed as a box plot (FIG. 2D and FIG. 9A).

Quantifying changes in BRD4 occupancy upon JQ1 treatment in all TNBC. $Log_2$ fold changes in BRD4 upon JQ1 treatment were quantified at BRD4 enriched regions in each respective cell line FIG. 12C.

All code related to genomic and transcriptome analysis can be found at github.com/BradnerLab/TNBC.

TABLE 1

List of BRD4-associated peptides identified by RIME.

| Sample Name | Factor | Cell line | Treatment | SILAC Heavy label | SILAC Light label | Data type |
|---|---|---|---|---|---|---|
| S1 | BRD4 | Sum159 | JQ1 vs DMSO | DMSO treatment | JQ1 | Unfiltered results |
| S2 | BRD4 | Sum159 vs Sum159-R | No treatment | Sum159 | Sum159-R | Unfiltered results |
| S3 | BRD4 | Sum159-R | JQ1 vs DMSO | DMSO treatment | JQ1 | Unfiltered results |
| S1_Filt | BRD4 | Sum159 | JQ1 vs DMSO | DMSO treatment | JQ1 | Filtered results |
| S2_Filt | BRD4 | Sum159 vs Sum159-R | No treatment | Sum159 | Sum159-R | Filtered results |

TABLE 1-continued

List of BRD4-associated peptides identified by RIME.

| Sample Name | Factor | Cell line | Treatment | SILAC Heavy label | SILAC Light label | Data type |
|---|---|---|---|---|---|---|
| S3_Filt | BRD4 | Sum159-R | JQ1 vs DMSO | DMSO treatment | JQ1 | Filtered results |

TABLE 2

List of siRNA, BDmut, 7A, and 7D primers, and shRNA sequences.

| Sequence Name | Sequence Notes | SEQ ID NO: | Sequence |
|---|---|---|---|
| si_BRD4_short isoform2_Sense | 3UTR | 1 | rGrGrA rCrCrA rArArU rGrGrC rArGrC rCrUrG rArUrU rArCC A |
| si_BRD4_short isoform1_Sense | 3UTR | 2 | rGrCrA rCrCrA rGrCrU rGrGrC rUrGrU rGrGrG rUrCrC rUrGA G |
| si_BRD4_Long isoform2_Sense | 3UTR | 3 | rCrUrG rGrCrA rCrUrG rArCrU rUrUrG rCrCrU rUrGrA rArCA G |
| si_BRD4_Long isoform1_Sense | 3UTR | 4 | rCrCrU rCrCrA rGrArC rArCrA rArUrG rGrCrA rCrUrG rCrUT A |
| siBRD3_1 | | 5 | rCrArGrArUrGrArCrArUrArGrUrGrCrUrArA |
| siBRD3_2 | | 6 | rGrCrUrUrUrGrUrCrArArCrArCrGrCrArUrU |
| siBRD2_1 | | 7 | rCrCrArUrGrUrUrCrArCrCrArArCrUrGrUrU |
| siBRD2_2 | | 8 | rGrCrArArUrGrGrCrArCrGrArArArGrCrUrA |
| siBRD4_1 | | 9 | rGrCrUrCrArArGrArCrArCrUrArUrGrGrArA |
| siBRD4_2 | | 10 | rUrGrArUrCrArCrArArUrCrArArGrUrCrUrA |
| BRD4N140A | BD1 mutant | 11 | CTATGTTTACAAATTGTTACATCT ACGCCAAGCCTGGAGATGACATA GTCTT |
| BRD4N433A | BD2 mutant | 12 | GTTCTCCAACTGCTATAAGTACGC CCCTCCTGACCATGAG |
| shBRD4-1 | | 13 | CCTGGAGATGACATAGTCTTA |
| shBRD4-2 | | 14 | CCAACCAAAGTCAGTTCCTTC |
| BRD4-CK2-4A-5 | 7A mutant first 4A sites | 15 | GCCCCGCCCGCATCCAGCGACGC CAGCAGCGATGCCTCCGCGGACA GTGAC |
| BRD4-CK2-4A-3 | 7A mutant first 4A sites | 16 | GTCACTGTCCGCGGAGGCATCGCT GCTGGCGTCGCTGGATGCGGGCG GGGC |
| BRD4-CK2-3A-5 | 7A mutant the other 3A sites | 17 | TCCGCGGACAGTGACGCTGCGAC TGATGACGCTGAGGAGGAGCGAG CC |
| BRD4-CK2-3A-3 | 7A mutant the other 3A sites | 18 | GGCTCGCTCCTCCTCAGCGTCATC AGTCGCAGCGTCACTGTCCGCGGA |
| BRD4-CK2-4D-5 | 7D mutant first 4D sites | 19 | GCCCCGCCCGATTCCAGCGACGA CAGCAGCGATGACTCCGACGACA GTGAC |

TABLE 2-continued

List of siRNA, BDmut, 7A, and 7D primers, and shRNA sequences.

| Sequence Name | Sequence Notes | SEQ ID NO: | Sequence |
|---|---|---|---|
| BRD4-CK2-4D-3 | 7D mutant first 4D sites | 20 | GTCACTGTCGTCGGAGTCATCGCT GCTGTCGTCGCTGGAATCGGGCG GGGC |
| BRD4-CK2-3D-5 | 7D mutant the other 3D sites | 21 | TCCGACGACAGTGACGATGACAC TGATGACGATGAGGAGGAGCGAG CC |
| BRD4-CK2-3D-3 | 7D mutant the other 3D sites | 22 | GGCTCGCTCCTCCTCATCGTCATC AGTGTCATCGTCACTGTCGTCGGA |
| shPP2A-C | PPA-C knockdown | 23 | CCCATGTTGTTCTTTGTTATT |

REFERENCES

1. Vaz-Luis, I. et al. Outcomes by tumor subtype and treatment pattern in women with small, node-negative breast cancer: a multi-institutional study. *J Clin Oncol* 32, 2142-2150, (2014).
2. Shah, S. P. et al. The clonal and mutational evolution spectrum of primary triple-negative breast cancers. *Nature*, (2012).
3. Lehmann, B. D. et al. Identification of human triple-negative breast cancer subtypes and preclinical models for selection of targeted therapies. *J Clin Invest* 121, (2011).
4. Metzger-Filho, O. et al. Dissecting the heterogeneity of triple-negative breast cancer. *J Clin Oncol* 30, 1879-1887, (2012).
5. Higgins, M. J. & Baselga, J. Targeted therapies for breast cancer. *J Clin Invest* 121, 3797-3803, (2011).
6. Hnisz, D. et al. Super-enhancers in the control of cell identity and disease. *Cell* 155, 934-947, (2013).
7. Smith, E. & Shilatifard, A. Enhancer biology and enhanceropathies. *Nature structural & molecular biology* 21, 210-219, (2014).
8. Delmore, J. E. et al. BET bromodomain inhibition as a therapeutic strategy to target c-Myc. *Cell* 146, 904-917, (2011).
9. Zuber, J. et al. RNAi screen identifies Brd4 as a therapeutic target in acute myeloid leukaemia. *Nature* 478, 524-528, (2011).
10. Belkina, A. C. & Denis, G. V. BET domain co-regulators in obesity, inflammation and cancer. *Nat Rev Cancer* 12, 465-477, (2012).
11. Wu, S. Y. & Chiang, C. M. The double bromodomain-containing chromatin adaptor Brd4 and transcriptional regulation. *J Biol Chem* 282, 13141-13145, (2007).
12. Yang, Z., He, N. & Zhou, Q. Brd4 recruits P-TEFb to chromosomes at late mitosis to promote G1 gene expression and cell cycle progression. *Mol Cell Biol* 28, 967-976, (2008).
13. Yang, Z. et al. Recruitment of P-TEFb for stimulation of transcriptional elongation by the bromodomain protein Brd4. *Mol Cell* 19, 535-545, (2005).
14. Filippakopoulos, P. et al. Selective inhibition of BET bromodomains. *Nature* 468, 1067-1073, (2010).
15. Puissant, A. et al. Targeting MYCN in neuroblastoma by BET bromodomain inhibition. *Cancer Discov* 3, 308-323, (2013).
16. Whyte, W. A. et al. Master transcription factors and mediator establish super-enhancers at key cell identity genes. *Cell* 153, 307-319, (2013).
17. Loven, J. et al. Selective inhibition of tumor oncogenes by disruption of super-enhancers. *Cell* 153, 320-334, (2013).
18. Chapuy, B. et al. Discovery and characterization of super-enhancer-associated dependencies in diffuse large B cell lymphoma. *Cancer Cell* 24, 777-790, (2013).
19. Heiser, L. M. et al. Subtype and pathway specific responses to anticancer compounds in breast cancer. *Proc Natl Acad Sci USA*, (2011).
20. Nagarajan, S. et al. Bromodomain protein BRD4 is required for estrogen receptor-dependent enhancer activation and gene transcription. *Cell reports* 8, 460-469, (2014).
21. Shi, J. et al. Disrupting the interaction of BRD4 with diacetylated Twist suppresses tumorigenesis in basal-like breast cancer. *Cancer Cell* 25, 210-225, (2014).
22. Perou, C. M. et al. Molecular portraits of human breast tumours. *Nature* 406, 747-752., (2000).
23. Dey, A., Nishiyama, A., Karpova, T., McNally, J. & Ozato, K. Brd4 marks select genes on mitotic chromatin and directs postmitotic transcription. *Mol Biol Cell* 20, 4899-4909, (2009).
24. Marotta, L. L. et al. The JAK2/STAT3 signaling pathway is required for growth of CD44CD24 stem cell-like breast cancer cells in human tumors. *J Clin Invest* 121, 2723-2735, (2011).
25. Ott, C. J. et al. BET bromodomain inhibition targets both c-Myc and IL7R in high-risk acute lymphoblastic leukemia. *Blood* 120, 2843-2852, (2012).
26. Brown, J. D. et al. NF-kappaB Directs Dynamic Super Enhancer Formation in Inflammation and Atherogenesis. *Mol Cell* 56, 219-231, (2014).
27. Anders, L. et al. Genome-wide localization of small molecules. *Nat Biotechnol* 32, 92-96, (2014).
28. Hayashi, H. et al. The OCT4 pseudogene POUSF1B is amplified and promotes an aggressive phenotype in gastric cancer. *Oncogene*, (2013).
29. Liu, T. et al. Knockdown of IRX2 inhibits osteosarcoma cell proliferation and invasion by the AKT/MMP9 signaling pathway. *Molecular medicine reports* 10, 169-174, (2014).
30. Choy, S. W. et al. A cascade of irx1a and irx2a controls shh expression during retinogenesis. *Dev Dyn* 239, 3204-3214, (2010).

31 Semenza, G. L. HIF-1 mediates metabolic responses to intratumoral hypoxia and oncogenic mutations. *J Clin Invest* 123, 3664-3671, (2013).
32 Watanabe, Y., Nagai, Y. & Takatsu, K. Activation and regulation of the pattern recognition receptors in obesity-induced adipose tissue inflammation and insulin resistance. *Nutrients* 5, 3757-3778, (2013).
33 Bessarabova, M. et al. Functional synergies yet distinct modulators affected by genetic alterations in common human cancers. *Cancer Res* 71, 3471-3481, (2011).
34 Marotta, L. L. et al. The JAK2/STAT3 signaling pathway is required for growth of CD44(+)CD24(-) stem cell-like breast cancer cells in human tumors. *J Clin Invest* 121, 2723-2735, (2011).
35 Arteaga, C. L. & Engelman, J. A. ERBB receptors: from oncogene discovery to basic science to mechanism-based cancer therapeutics. *Cancer Cell* 25, 282-303, (2014).
36 Engelman, J. A. et al. MET amplification leads to gefitinib resistance in lung cancer by activating ERBB3 signaling. *Science* 316, 1039-1043, (2007).
37 Bernardo, G. M. et al. FOXA1 represses the molecular phenotype of basal breast cancer cells. *Oncogene* 32, 554-563, (2013).
38 Bernardo, G. M. et al. FOXA1 is an essential determinant of ERalpha expression and mammary ductal morphogenesis. *Development* 137, 2045-2054, (2010).
39 Jiang, Y. W. et al. Mammalian mediator of transcriptional regulation and its possible role as an end-point of signal transduction pathways. *Proc Natl Acad Sci USA* 95, 8538-8543, (1998).
40 Rahman, S. et al. The Brd4 extraterminal domain confers transcription activation independent of pTEFb by recruiting multiple proteins, including NSD3. *Mol Cell Biol* 31, 2641-2652, (2011).
41 Schroder, S. et al. Two-pronged binding with bromodomain-containing protein 4 liberates positive transcription elongation factor b from inactive ribonucleoprotein complexes. *J Biol Chem* 287, 1090-1099, (2012).
42 Mohammed, H. et al. Endogenous purification reveals GREB1 as a key estrogen receptor regulatory factor. *Cell reports* 3, 342-349, (2013).
43 Wu, S. Y., Lee, A. Y., Lai, H. T., Zhang, H. & Chiang, C. M. Phosphoswitch triggers Brd4 chromatin binding and activator recruitment for gene-specific targeting. *Mol Cell* 49, 843-857, (2013).
44. Choudhury, S. et al. Molecular Profiling of Human Mammary Gland Links Breast Cancer Risk to a p27(+) Cell Population with Progenitor Characteristics. *Cell stem cell* 13, 117-130 (2013).
45. Mellacheruvu, D. et al. The CRAPome: a contaminant repository for affinity purification-mass spectrometry data. *Nat Methods* 10, 730-736 (2013).
46. Trapnell, C., Pachter, L. & Salzberg, S. L. TopHat: discovering splice junctions with RNA-Seq. *Bioinformatics* 25, 1105-1111 (2009).
47. Trapnell, C. et al. Transcript assembly and quantification by RNA-Seq reveals unannotated transcripts and isoform switching during cell differentiation. *Nat Biotechnol* 28, 511-515 (2010).
48. Langmead, B., Trapnell, C., Pop, M. & Salzberg, S. L. Ultrafast and memory-efficient alignment of short DNA sequences to the human genome. *Genome Biol* 10, R25 (2009).
49. Zhang, Y. et al. Model-based analysis of ChIP-Seq (MACS). *Genome Biol* 9, R137 (2008).
50. Lin, C. Y. et al. Transcriptional amplification in tumor cells with elevated c-Myc. *Cell* 151, 56-67 (2012).
49 Chou, T. C. & Talalay, P. Quantitative analysis of dose-effect relationships: the combined effects of multiple drugs or enzyme inhibitors. *Advances in enzyme regulation* 22, 27-55, (1984).
50 Choudhury, S. et al. Molecular Profiling of Human Mammary Gland Links Breast Cancer Risk to a p27(+) Cell Population with Progenitor Characteristics. *Cell stem cell* 13, 117-130, (2013).
51 Mellacheruvu, D. et al. The CRAPome: a contaminant repository for affinity purification-mass spectrometry data. *Nat Methods* 10, 730-736, (2013).
52 Trapnell, C., Pachter, L. & Salzberg, S. L. TopHat: discovering splice junctions with RNA-Seq. *Bioinformatics* 25, 1105-1111, (2009).
53 Trapnell, C. et al. Transcript assembly and quantification by RNA-Seq reveals unannotated transcripts and isoform switching during cell differentiation. *Nat Biotechnol* 28, 511-515, (2010).
54 Langmead, B., Trapnell, C., Pop, M. & Salzberg, S. L. Ultrafast and memory-efficient alignment of short DNA sequences to the human genome. *Genome Biol* 10, R25, (2009).
55 Zhang, Y. et al. Model-based analysis of ChIP-Seq (MACS). *Genome Biol* 9, R137, (2008).
56. Lin, C. Y. et al. Transcriptional amplification in tumor cells with elevated c-Myc. *Cell* 151, 56-67, (2012).

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A method for treating a cancer, the method comprising: administering to a subject in need thereof a bromodomain and extra terminal (BET) inhibitor and a protein phosphatase 2A (PP2A) activator in an amount effective to treat the cancer, wherein the cancer is resistant to treatment by the BET inhibitor alone.

2. The method of claim 1, wherein the BET inhibitor and the PP2A activator are synergistic in treating the cancer, compared to the BET inhibitor alone or the PP2A activator alone.

3. The method of claim 1, wherein the BET inhibitor is a bromodomain-containing protein 2 (BRD2) inhibitor, bromodomain-containing protein 3 (BRD3) inhibitor, or bromodomain-containing protein 4 (BRD4) inhibitor.

4. The method of claim 3, wherein the BET inhibitor is a small molecule.

5. The method of claim 4, wherein the BET inhibitor is JQ1 or a derivative thereof.

6. The method of claim 1, wherein the PP2A activator is a small molecule.

7. The method of claim 6, wherein the PP2A activator is a phenothiazine compound or FTY720.

8. The method of claim 7, wherein the phenothiazine compound is selected from the group consisting of chlorpromazine, mesoridazine, thioridazine, acetophenazine, fluphenazine, perphenazine, trifluoperazine and pharmaceutically acceptable salts and esters thereof.

9. The method of claim 1, wherein the BET inhibitor and the PP2A activator are administered concurrently or sequentially.

10. The method of claim 5, wherein the PP2A activator is a small molecule.

11. The method of claim 10, wherein the PP2A activator is a phenothiazine compound or FTY720.

12. The method of claim 11, wherein the phenothiazine compound is selected from the group consisting of chlorpromazine, mesoridazine, thioridazine, acetophenazine, fluphenazine, perphenazine, trifluoperazine and pharmaceutically acceptable salts and esters thereof.

13. A method for treating a cancer, the method comprising: administering to a subject in need thereof a bromodomain and extra terminal (BET) inhibitor and a protein phosphatase 2A (PP2A) activator in an amount effective to treat the cancer, wherein the subject is identified as being in need thereof if a ratio of phosphorylated bromodomain-containing protein 4 (pBRD4) to unphosphorylated BRD4 (BRD4) in a tumor sample obtained from the subject is increased as compared to a control ratio of pBRD4 to BRD4.

14. The method of claim 13, wherein the BET inhibitor is JQ1 or a derivative thereof.

15. The method of claim 13, wherein the PP2A activator is a phenothiazine compound or FTY720.

16. The method of claim 14, wherein the PP2A activator is a phenothiazine compound or FTY720.

17. A method for treating a cancer, the method comprising: administering to a subject in need thereof a bromodomain and extra terminal (BET) inhibitor and a protein phosphatase 2A (PP2A) activator in an amount effective to treat the cancer, wherein the subject is identified as being in need thereof if the BRD4 intracellular location of bromodomain-containing protein 4 (BRD4) in a tumor sample obtained from the subject is the nucleus.

18. The method of claim 17, wherein the BET inhibitor is JQ1 or a derivative thereof.

19. The method of claim 17, wherein the PP2A activator is a phenothiazine compound or FTY720.

20. The method of claim 18, wherein the PP2A activator is a phenothiazine compound or FTY720.

\* \* \* \* \*

UNITED STATES PATENT AND TRADEMARK OFFICE
CERTIFICATE OF CORRECTION

| | | |
|---|---|---|
| PATENT NO. | : 11,666,580 B2 | Page 1 of 1 |
| APPLICATION NO. | : 15/751914 | |
| DATED | : June 6, 2023 | |
| INVENTOR(S) | : Polyak et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1223 days.

Signed and Sealed this
Nineteenth Day of August, 2025

Coke Morgan Stewart
*Acting Director of the United States Patent and Trademark Office*